US010835546B2

(12) United States Patent
John et al.

(10) Patent No.: US 10,835,546 B2
(45) Date of Patent: *Nov. 17, 2020

(54) APP SPECIFIC BACE INHIBITORS (ASBIS) AND USES THEREOF

(71) Applicant: BUCK INSTITUTE FOR RESEARCH ON AGING, Novato, CA (US)

(72) Inventors: Varghese John, Los Angeles, CA (US); Dale E. Bredesen, Los Angeles, CA (US)

(73) Assignee: BUCK INSTITUTE FOR RESEARCH ON AGING, Novato, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/433,879

(22) Filed: Jun. 6, 2019

(65) Prior Publication Data

US 2019/0298748 A1  Oct. 3, 2019

Related U.S. Application Data

(63) Continuation of application No. 14/384,641, filed as application No. PCT/US2013/032481 on Mar. 15, 2013, now Pat. No. 10,357,508.

(60) Provisional application No. 61/728,688, filed on Nov. 20, 2012, provisional application No. 61/612,848, filed on Mar. 19, 2012.

(51) Int. Cl.
| | |
|---|---|
| *C07D 311/30* | (2006.01) |
| *A61K 31/352* | (2006.01) |
| *A61K 31/7048* | (2006.01) |
| *C07D 311/24* | (2006.01) |
| *A61K 31/366* | (2006.01) |

(52) U.S. Cl.
CPC ........ *A61K 31/7048* (2013.01); *A61K 31/352* (2013.01); *A61K 31/366* (2013.01); *C07D 311/24* (2013.01); *C07D 311/30* (2013.01)

(58) Field of Classification Search
None
See application file for complete search history.

(56) References Cited

U.S. PATENT DOCUMENTS

| | | | |
|---|---|---|---|
| 6,066,642 | A | 5/2000 | Jacobson et al. |
| 6,103,756 | A | 8/2000 | Gorsek |
| 6,492,377 | B1 | 12/2002 | Blech et al. |
| 8,466,195 | B2 | 6/2013 | Maher et al. |
| 10,357,508 | B2 | 7/2019 | John et al. |
| 2003/0055103 | A1 | 3/2003 | Heinzen et al. |
| 2007/0191330 | A1 | 8/2007 | Castillo et al. |
| 2007/0286911 | A1 | 12/2007 | Xie et al. |

FOREIGN PATENT DOCUMENTS

| | | |
|---|---|---|
| CN | 1649611 A | 8/2005 |
| JP | 2005104850 A | 4/2005 |
| WO | 2003092599 A2 | 11/2003 |
| WO | 2006001665 A1 | 1/2006 |
| WO | 2008011538 A2 | 1/2008 |
| WO | 2010124623 A1 | 11/2010 |
| WO | 2012019435 A2 | 2/2012 |
| WO | 2013142370 A1 | 9/2013 |

OTHER PUBLICATIONS

Natoli et al., "Enzyme-Catalyzed Alcoholysis of Flavone Acetates in Organic Solvent" Tetrahedron Letters vol. 31 No. 50 pp. 7371-7374 (Year: 1990).*
Chavan, J. J., and Robinson, Robert, "99. Anthoxanthins. Part XIV. [omega]-Hydroxyphloracetophenone and Certain Derivatives. Synthesis of Galangin under Milder Conditions than those used heretofore." Journal of Chemical Society, Jan. 1, 1933, pp. 368-370.
Extended European Search Report from corresponding European Patent Application No. 19180690.0 dated Jan. 15, 2020.
Canadian Office Action from correspondening Canadian Application No. 2,867,891 dated Dec. 30, 2019.
Sawasdee, P., et al., "Anticholinesterase Activity of 7-Methoxyflavones Isolated from Kaempferia parviflora," Phytother. Res. 23: 1792-1794 (2009).
Second Office Action from Chinese Application No. 201710107804.5 dated Sep. 9, 2019 (with English translation).
Zhang, B., et al., Pharmacological Basics, p. 136, HeNan Science and Technology Press, published Jul. 2010, first edition.
Huang, Z., et al., Exacts of Clinical Internal Medicine, New Theory, New Knowledge and Development, p. 585, Henan Medical University Press, Nov. 1998, first edition.
Ansari et al., "Protective Effect of Quercetin in Primary Neurons Against Abeta (1-42): Relevance to Alzheimer's Disease" J Nutr Biochem. 20(4):269-275, Apr. 2009.
Australian Patent Examination Report No. 1 dated Dec. 19, 2017 issued in Australian Patent Application No. 2017201599, 7 pages.
Australian Patent Examination Report No. 1 dated Dec. 4, 2015 issued in Australian Patent Application No. 2013235422, 7 pages.

(Continued)

*Primary Examiner* — Eric Olson
(74) *Attorney, Agent, or Firm* — Harness, Dickey & Pierce, P.L.C.

(57) ABSTRACT

In certain embodiments APP-specific BACE inhibitors (ASBIs) are provided as well as uses thereof. In certain embodiments methods of preventing delaying the onset of a pre-Alzheimer's condition and/or cognitive dysfunction, and/or ameliorating one or more symptoms of a pre-Alzheimer's condition and/or cognitive dysfunction, or preventing or delaying the progression of a pre-Alzheimer's condition or cognitive dysfunction to Alzheimer's disease are provided where the method involves administering to a subject in need thereof an APP specific BACE inhibitor (ASBI) in an amount sufficient to prevent or delay the onset of a pre-Alzheimer's cognitive dysfunction, and/or to ameliorate one or more symptoms of a pre-Alzheimer's cognitive dysfunction, and/or to prevent or delay the progression of a pre-Alzheimer's cognitive dysfunction to Alzheimer's disease. In certain embodiments the ASBI is a flavonoid (e.g. galangin) or flavonoid progrug (e.g., galangin prodrug).

16 Claims, 10 Drawing Sheets

(56) References Cited

OTHER PUBLICATIONS

Australian Patent Examination Report No. 2 dated Nov. 11, 2016 issued in Australian Patent Application No. 2013235422, 4 pages.
Australian Patent Examination Report No. 3 dated Nov. 21, 2016 issued in Australian Patent Application No. 2013235422, 4 pages.
Biasutto et al., "Ester-Based Precursors to increase the Bioavailability of Quercetin" Journal of Medicinal Chemistry, 50:241-253 (2007).
Canadian Office Action dated Feb. 28, 2019 issued in Canadian Patent Application No. 2,867,891, 5 pages.
Chen, "Research Progress in the Pathogenesis of Alzheimber's Disease" Chinese Medical Journal, 131(13):1618-1624 (2018).
Chinese Office Action dated Dec. 3, 2018 issued in Chinese Patent Application No. 201710107804.5 (with English translation), 18 pages.
Chinese Second Office Action dated Jul. 8, 2016 issued in Chinese Patent Application No. 201380023606.0 (with English translation), 14 pages.
Cho, Jung Keun et al., "Inhibition and structural reliability of prenylated flavones from the stem bark of Mortise lhou on β-secretase (BACE-1)" Bioorganic & Medicinal Chemistry Letters, 21(10):2945-48 (2011).
Choi et al., "A Flavonol Glycoside, Isolated From Roots of Panax notoginseng, Reduces Amyloid-Beta-Induced Neurotoxicity in Cultured Neurons: Signaling Transduction and Drug Development for Alzheimer's Disease" Journal of Alzheimer's Disease, 19(3):795-811, Jan. 28, 2010.
Compton, Benjamin J., et al., "Use of acyl substituents to favour 2,3-epoxidation of 5,7-dioxygenated flavones with dimethyldioxirane" Tetrahedron, 67:718-726 (2011), 9 pages.
Dai et al., "The genes associated with early-onset Alzheimer's disease" Oncotarget, 9(19):15132-15143 (2018).
Drug package insert, Aricept, Jul. 2009, 20th edition, the Internet, <URL: http://www.drc.toyaku.ac.jp/packins/pdf/170033/170033_1190012C1020_1_16/170033_1190012C1020_1_16.pdf> (with English translation), 32 pages.
Ettmayer, Peter, "Lessons Learned from Marketed and Investigational Prodrugs" Journal of Medicinal Chemistry, 47(10):2394-2404 (2004).
European Extended Search Report dated Feb. 22, 2016 issued in European Patent Application No. 13763620.5, 12 pages.
European Office Action dated Jul. 3, 2018 issued in European Patent Application No. 13763620.5, 4 pages.
European Supplementary Partial Search Report dated Oct. 29, 2015 issued in European Patent Application No. 13763620.5, 8 pages.
Freudenberg-Hua, et al., "The Role of Genetics in Advancing Precision Medicine for Aizheirner's Disease—A Narrative Review" Frontiers in Medicine, 5(108):1-13 (2018).
Greene, Theodora W. et al., "Protective Groups in Organic Synthesis, Third Edition" A Wiley-Interscience Publication (2002), 6 pages.
Gun et al., "Galangin, a flavonol derived from Rhizoma Alpiniae Officinarum, inhibits acetylcholinesterase activity in vitro" Chemico-Biological Interactions, 187(1-3):246-48 (2010).
Hanneken et al., "Flavonoids Protect Human Retinal Pigment Epithelial Cells from Oxidative-Stress-Induced Death" Investagative Ophthamlogy and Visual Science, 47(7):3164-3177 (2006).
Ishige et al., "Flavonoids Protect Neuronal Cells From Oxidative Stress by Three Distinct Mechanisms" Free Radical Biology and Medicine, 30(4):433-446 (2001).

Japanese 2nd Office Action dated Aug. 7, 2017 issued in Japanese Patent Application No. 2015-501819 (with English translation), 7 pages.
Japanese Office Action dated Dec. 3, 2018 issued in Japanese Patent Application No. 2017-233222 (with English translation), 13 pages.
Japanese Office Action dated Jan. 4, 2017 issued in Japanese Patent Application No. 2015-501819 (with English translation), 9 pages.
Japanese Pre-Appeal Report dated Jan. 12, 2018 issued in Japanese Patent Application No. 2015-501819 (with English translation), 7 pages.
Jimenex-Aliaga, Karim, et al., "Quercetin and rutin exhibit antiamyloidogenic and fibril-disaggregationg effects in vitro and potent antioxidant activity in APPswe cells" Life Sciences 89(25-26):939-945 (2011), 7 pages.
Korean Office Action dated Feb. 18, 2019 issued in Korean Patent Application No. 10-2014-7029321 (with English translation), 16 pages.
Paris, Daniel, et al., "Flavonoids lower Alzheimer's Aβ production via an NfkB dependent mechanism" Bioinformation, 6(6):229-236 (2011), 8 pages.
PCT International Preliminary Report on Patentability dated Sep. 23, 2014 issued in PCT/US13/32481, 8 pages.
PCT International Search Report and Written Opinion dated Jun. 14, 2013 issued in PCT/US13/32481, 14 pages.
Sermboonpaisarn, Thiendanai, et al., "Potent and selective butyrylcholinesterase inhibitors from Ficus foveolata" Fitoterapia, 83(4):780-784.
Shimmyo, Yoshiari, et al., "Flavonols and flavones as BACE-1 inhibitors: Structure-activity relationship in cell-free, cell-based and in silico studies reveal novel pharmacophore features" Biochemica et Biophysica Acta, 1780(5):819-825.
Silverman, Richard B., "The Organic Chemistry of Drug Design and Drug Action" Published by Academic Press, pp. 4-47 (1992).
Stella, Valentino J., "Prodrugs as therapeutics" Expert Opinion on Therapeutic Patents, 14:3:277-280 (2004).
Testa, Bernard, et al., "Prodrug Research: futile or fertile?" Biochemical Pharmacology, 68:2097-2106 (2004).
U.S. Final Office Action dated Nov. 20, 2018 issued in U.S. Appl. No. 14/384,641, 10 pages.
U.S. Final Office Action dated Jan. 6, 2017 issued in U.S. Appl. No. 14/384,641, 11 pages.
U.S. Non-final Office Action dated Mar. 20, 2018 issued in U.S. Appl. No. 14/384,641, 10 pages.
U.S. Non-final Office Action dated May 23, 2016 issued in U.S. Appl. No. 14/384,641, 14 pages.
Vassar, Robert, et al., "β-Secretase Cleavage of Alzheimer's Amyloid Precursor Protein by the Transmembrane Aspartic Protease BACE" Science, 286(5440):735-741 (1999), 7 pages.
Wermuth, "The Practice of Medicinal Chemistry" Technomics, Inc., 2:275-277 (with English translation), 16 pages.
Williams, Robert J., et al., "Flavonoids, cognition, and dementia: Actions, mechanisms, and potential therapeutic utility for Alzheimber disease" Free Radical Biology & Medicine, 52(1):35-45 (2012), 11 pages.
Wolff, Manfred E., et al., "Burger's Medicinal Chemistry and Drug Discovery, Fifth Edition" vol. 1, pp. 975-977 (1994).
Zhu et al., "Flavonoids Possess Neuroprotective Effects on Cultured Pheochrornocytorna PC12 Cells: A Comparison of Different Flavonoids in Activating Estrogenic Effect and in Preventing a-Amyloid-Induced Cell Death" J Agric Food Chem 55:2438-2445 (2007).

* cited by examiner

Cas # 548-83-4
Galangin 1

Cas # 1265223-39-9
2

3

4

Cas # 1265223-40-2
5

APP SPECIFIC BACE INHIBITORS (ASBIS) AND USES THEREOF

CROSS-REFERENCE TO RELATED APPLICATIONS

This application claims benefit of and priority to U.S. Ser. No. 61/728,688, filed on Nov. 20, 2012, and to U.S. Ser. No. 61/612,848, filed on Mar. 19, 2012, both of which are incorporated herein by reference in their entirety for all purposes.

STATEMENT OF GOVERNMENTAL SUPPORT

This work was supported in part by Grant No R01 AG034427 from National Institute on Aging of the National Institutes of Health. The Government has certain rights in this invention.

BACKGROUND

Amyloid beta peptide (Aβ) is a primary component of beta amyloid fibrils and plaques, which are regarded as having a role in an increasing number of pathologies. Examples of such pathologies include, but are not limited to, Alzheimer's disease, Down's syndrome, Parkinson's disease, memory loss (including memory loss associated with Alzheimer's disease and Parkinson's disease), attention deficit symptoms (including attention deficit symptoms associated with Alzheimer's disease, Parkinson's disease, and Down's syndrome), dementia (including pre-senile dementia, senile dementia, dementia associated with Alzheimer's disease, Parkinson's disease, and Down's syndrome), progressive supranuclear palsy, cortical basal degeneration, neurodegeneration, olfactory impairment (including olfactory impairment associated with Alzheimer's disease, Parkinson's disease, and Down's syndrome), β-amyloid angiopathy (including cerebral amyloid angiopathy), hereditary cerebral hemorrhage, mild cognitive impairment ("MCI"), glaucoma, amyloidosis, type II diabetes, hemodialysis (β2 microglobulins and complications arising therefrom), neurodegenerative diseases such as scrapie, bovine spongiform encephalitis, Creutzfeld Jakob disease, traumatic brain injury and the like.

Aβ peptides are short peptides that are produced by proteolysis of the transmembrane protein called amyloid precursor protein ("APP"). Aβ peptides are made from the cleavage of APP by β-secretase activity at a position near the N-terminus of Aβ, and by gamma secretase activity at a position near the C-terminus of Aβ. (APP is also cleaved by α-secretase activity, resulting in the secreted, non-amyloidogenic fragment known as soluble APPα). Beta site APP Cleaving Enzyme ("BACE-1") is regarded as the primary aspartyl protease responsible for the production of Aβ by β-secretase activity. The inhibition of BACE-1 has been shown to inhibit the production of Aβ.

Alzheimer's disease (AD) is estimated to afflict more than 20 million people worldwide and is believed to be the most common cause of dementia. As the World population ages, the number of people with Alzheimer's disease (AD, currently approximately 5.4 million in the United States, will continue to rise. Alzheimer's is a neurodegenerative disease associated with progressive dementia and memory loss. Two key characteristics of AD are the accumulation of extracellular deposits containing aggregated Aβ peptide and neuronal synaptic loss in the AD in specific brain regions. Although AD pathogenesis is complex, compelling genetic and biochemical evidence suggest that overproduction of Aβ, or failure to clear this peptide is the earliest event in the amyloid cascade that lead to AD primarily through amyloid deposition, which is presumed to be involved in neurofibrillary tangle formation, neuronal dysfunction and microglia activation, that characterize AD-affected brain tissues.

The accumulation of Aβ is considered to be the earliest event in a complex cascade that leads to neurodegeneration, as discerned from compelling genetic and biochemical evidence. The amyloid cascade hypothesis (Hardy and Allsop (1991) Trends Pharmacol. Sci., 12: 383-388; Selkoe (1996) J. Biol. Chem., 271: 18295-18298; Hardy (1997) Trends Neurosci., 20: 154-159; Hardy and Selkoe (2002) Science, 297: 353-356) states that overproduction of Aβ, or failure to clear this peptide, leads to AD, primarily through amyloid deposition, which is presumed to be involved in neurofibrillary tangle formation, neuronal dysfunction, and microglia activation, that are hallmarks of AD-affected brain tissues (Busciglio et al. (1995) Neuron, 14: 879-888; Gotz et al. (1995) EMBO J., 14: 1304-1313; Lewis et al. (2001) Science, 293: 1487-1491; Hardy et al. (1985) Nat Neurosci., 1: 355-358).

Considering the causative role of Aβ in AD etiology, novel therapeutic strategies that lower Aβ levels or prevent the formation of the neurotoxic Aβ species have been suggested as a method to prevent or slow the progression of the disease. Indeed, the major focus over the last decade has been to inhibit brain Aβ production and aggregation, to increase parenchymal Aβ clearance, and to interfere with Aβ-induced cell death.

The sequential cleavage of APP by membrane-bound proteases β-secretase and γ-secretase results in the formation of Aβ. A competing proteolytic pathway to the β-secretase pathway, the α-secretase pathway, results in cleavage of APP within the Aβ domain, thereby precluding the generation of Aβ (Selkoe (2001) Physiol. Rev., 81: 741-766; Hussain et al. (1999) Mol. Cell. Neurosci., 14: 419-427; Sinha et al. (1999) Nature, 402: 537-540; Vassar et al. (1999) Science, 286: 735-741). The β-Site APP cleavage enzyme-1 (BACE1) was identified as the major β-secretase activity that mediates the first cleavage of APP in the β-amyloidogenic pathway (Id.).

BACE1 is a 501 amino acid protein that bears homology to eukaryotic aspartic proteases, especially from the pepsin family (Yan et al. (1999) Nature, 402: 533-537). Similar to other aspartic proteases, BACE1 is synthesized as a zymogen with a pro-domain that is cleaved by furin to release the mature protein. BACE1 is a type-I transmembrane protein with a luminal active site that cleaves APP to release an ectodomain (sAPPβ) into the extracellular space. The remaining C-terminal fragment (CTF) undergoes further cleavage by γ-secretase, leading to the release of Aβ and the APP intracellular C-terminal domain (AICD).

The presenilins have been proposed to be the major enzymatic component of γ-secretase, whose imprecise cleavage of APP produces a spectrum of Aβ peptides varying in length by a few amino acids at the C-terminus. The majority of Aβ normally ends at amino acid 40 (Aβ40), but the 42-amino acid variant (Aβ42) has been shown to be more susceptible to aggregation, and has been hypothesized to nucleate senile plaque formation. The modulation of the γ-secretase can also lead to increase in the 38-amino acid variant (Aβ38). The competing α-secretase pathway is the result of sequential cleavages by α- and γ-secretase. Three metalloproteases of the disintegrin and metalloprotease family (ADAM 9, 10, and 17) have been proposed as candidates for the α-secretase activity, which cleaves APP at position 16 within the Aβ sequence. Using overexpression experiments, ADAM-10 has been shown to be the likely α-secretase for cleavage of APP (Vassar (2002) *Adv. Drug Deliv. Rev.*, 54: 1589-1602; Buxbaum et al. (1998) *J. Biol. Chem.*, 273: 27765-27767; Koike et al. (1999) *Biochem. J.*, 343(Pt 2): 371-375). This cleavage also releases an ectodomain (sAPPα), which displays neuroprotective functions (Lammich et al. (1999) *Proc. Natl. Acad. Sci. USA*, 96: 3922-3927). Subsequent cleavage of the 83-amino acid CTF (C83) releases p3, which is non-amyloidogenic, and AICD (Furukawa et al. (1996) *J. Neurochem.*, 67: 1882-1896). The functions of these fragments are not fully elucidated, although AICD is hypothesized to mediate intracellular signaling.

Research clarifying the metabolic pathways that regulate the production of Aβ from the Amyloid Precursor Protein (APP) indicates that the secretases that produce Aβ are good therapeutic targets, since inhibition of either β- or γ-secretase limits Aβ production. The fact that β-secretase initiates APP processing, and thus serves as the rate limiting step in production of Aβ, its inhibition has attracted efforts by many research groups. Examples from the patent literature are growing and include, for example, WO2006009653, WO2007005404, WO2007005366, WO2007038271, WO2007016012, US2005/0282826, US2007072925, WO2007149033, WO2007145568, WO2007145569, WO2007145570, WO2007145571, WO2007114771, US20070299087, WO2005/016876, WO2005/014540, WO2005/058311, WO2006/065277, WO2006/014762, WO2006/014944, WO2006/138195, WO2006/138264, WO2006/138192, WO2006/138217, WO2007/050721, WO2007/053506, WO2006/138230, WO2006/138265, WO2006/138266, WO2007/053506, WO2007/146225, WO2008/073365, WO2008/073370, WO2008/103351, US2009/041201, US2009/041202, and WO2010/047372

A limitation of protease inhibitory strategies is the inhibition of cleavage of all substrates of a given targeted protease, such as BACE or the γ-secretase complex. In the case of γ-secretase, substrates other than APP, such as Notch, raise concerns for potential side effects of γ-secretase inhibition, and the recent failure of the γ-secretase inhibitor. Semagacestat, serves to reinforce such concerns.

BACE is a key enzyme involved in processing of APP leading to the production of Aβ42 and the Alzheimer's disease (AD) pathology. BACE-1 (also called BACE) has become a popular research area since its discovery, and has perhaps surpassed γ-secretase as the most promising target for pharmaceutical research. One problem with γ-secretase as a target is its known cleavage of Notch which serves important functions in neuronal development. Presenilin knockout mice demonstrated abnormal somitogenesis and axial skeletal development with shortened body length, as well as cerebral hemorrhages (Shen et al. (1997) *Cell*, 89: 629-639; Wong et al. (1997) *Nature*, 387: 288-292). In contrast, several groups reported that BACE1 knockout mice are healthy and show no signs of adverse effect (Luo et al. (2001) *Nat. Neurosci.*, 4: 231-232; Roberds et al. (2001) *Hum. Mol. Genet.*, 10: 1317-1324), while one group noticed subtle neurochemical deficits and behavioral changes in otherwise viable and fertile mice (Harrison et al. (2003) *Mol. Cell Neurosci.*, 24: 646-655). Although recent studies have shown that BACE1 knockout mice exhibit hypomyelination of peripheral nerves (Willem et al. (2006) *Science*, 314: 664-666), the consequences of BACE1 inhibition in adult animals, where myelination has already taken place, are unclear. Recently BACE1 has been reported to cleave multiple substrates, including ST6Gal I, PSGL-1, subunits of voltage-gated sodium channels, APP-like proteins (APLPs), LDL receptor related protein (LRP) and, most recently, type III neuregulin 1 (NRG1) (Willem et al. (2006) *Science*, 314: 664-666; Hu et al. (2006) *Nat. Neurosci.*, 9: 1520-1525). The consequences of inhibiting BACE1 directly are therefore not yet fully understood.

Molecular modeling (Sauder et al. (2000) *J. Mol. Biol.*, 300: 241-248) and subsequent X-ray crystallography (Hong et al. (2000) *Science*, 290: 150-153; Maillard et al. (2007) *J. Med. Chem.*, 50: 776-781) of the BACE-1 active site complexed with a transition-state inhibitor provided crucial information about BACE-1-substrate interactions. Structurally, the BACE-1 active site is more open and less hydrophobic than other aspartyl proteases, making development of effective in vivo BACE inhibitor candidates difficult. While a there is a large drug discovery effort focused on development of direct BACE inhibitors, none so far have advanced significantly in clinical testing.

A few BACE inhibitors such as LY2811376 and CTS21166 entered clinical testing, but did not go forward beyond Phase-1 due to safety reasons. The discovery of other physiological substrates of BACE raises a major concern in the clinical development of BACE inhibitors or BACE modulators and could be a significant roadblock in advancement of these inhibitors as a therapy for the disease.

SUMMARY

In certain embodiments flavonoid and derivatives or analogues thereof (and prodrugs thereof) are identified that are believed to act as APP-specific (or APP-selective) BACE inhibitors (ASBIs). In various embodiments the flavonoids can be characterized by the formula:

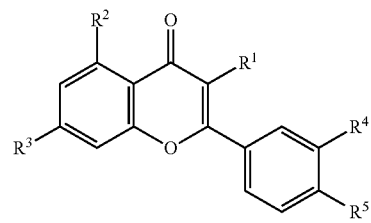

where $R^1$ is selected from the group consisting of OH, O-saccaharide, O-alkyl, O-trifluoromethyl, O-aryl, O-heteroaryl, and carbamate; $R^4$ and $R^5$ are independently selected from the group consisting of H, OH, $NH_2$, O-alkyl, O-trifluoromethyl, S-alkyl, S-aryl, carboxylate, halogen, NH-alkyl, N,N-dialkyl, NHCO-alkyl, and heteroaryl, alkyl urea, and carbamate; and $R^2$ and $R^3$ are independently selected from the group consisting of H, OH, $NH_2$, O-alkyl, O-trifluoromethyl, S-alkyl, S-aryl, carboxylate, halogen, NH-alkyl, N,N-dialkyl, NHCO-alkyl, heteroaryl, alkyl urea, and carbamate. In certain embodiments $R^2$ and/or $R^3$ is OH. In certain embodiments $R^2$ is OH and $R^3$ is OH. In certain embodiments $R^2$ and/or $R^3$ are independently selected from the group consisting of O-alkyl, S-alkyl, NH-alkyl and NHCO-alkyl. In certain embodiments $R^2$ and $R^3$ are independently selected from the group consisting of O-alkyl, S-alkyl, NH-alkyl and NHCO-alkyl (e.g., where the alkyl component of said O-alkyl, S-alkyl, NH-alkyl and NHCO-alkyl is a $C_{1-12}$ alkyl, or a $C_{1-9}$ alkyl, or a $C_{1-6}$ alkyl, or a $C_{1-3}$ alkyl). In certain embodiments $R^2$ and/or $R^3$ is halogen (e.g., Cl, Br, Fl, I, etc.). In certain embodiments $R^2$ is halogen and $R^3$ is halogen. In certain embodiments $R^2$ and/or $R^3$ are independently selected from the group consisting of Cl, Br, Fl, and I. In certain embodiments $R^2$ and/or $R^3$ is selected from the group consisting of S-aryl and heteroaryl. In certain embodiments $R^2$ and $R^3$ are independently selected S-aryl. In certain embodiments $R^2$ and $R^3$ are independently selected heteroaryl. In certain embodiments where $R^4$ and/or $R^5$ is OH. In certain embodiments $R^4$ is H and $R^5$ is OH. In certain embodiments $R^4$ is OH and $R^5$ is H. In certain embodiments $R^4$ is OH and $R^5$ is OH. In certain embodiments $R^4$ and/or $R^5$ is H. In certain embodiments $R^4$ is H and $R^5$ is H. In certain embodiments when $R^4$ and/or $R^5$ is OH, $R^1$ is O-Saccharide. In certain embodiments where $R^4$ and/or $R^5$ are independently selected from the group consisting of O-alkyl, S-alkyl, NH-alkyl and NHCO-alkyl. In certain embodiments $R^4$ and $R^5$ are independently selected from the group consisting of O-alkyl, S-alkyl, NH-alkyl and NHCO-alkyl (e.g., where the alkyl component of said O-alkyl, S-alkyl, NH-alkyl and NHCO-alkyl is a $C_{1-12}$ alkyl, or a $C_{1-9}$ alkyl, or a $C_{1-6}$ alkyl, or a $C_{1-3}$ alkyl). In certain embodiments $R^4$ and/or $R^5$ is halogen. In certain embodiments $R^4$ is halogen and $R^5$ is halogen. In certain embodiments $R^4$ and/or $R^5$ are independently selected from the group consisting of Cl, Br, Fl, and I. In certain embodiments $R^4$ and/or $R^5$ is selected from the group consisting of S-aryl and heteroaryl. In certain embodiments $R^4$ and $R^5$ are independently selected S-aryl. In certain embodiments $R^4$ and $R^5$ are independently selected heteroaryl. In certain embodiments $R^1$ is O-Saccharide (e.g., O-monosaccharide, O-disaccharide, O-trisaccharide). In certain embodiments $R^1$ is O-alkyl, O-trifluoromethyl, O-aryl, or O-heteroaryl. In certain embodiments the APP specific (or selective) BACE inhibitor is galangin or a derivative thereof. In certain embodiments the APP specific BACE inhibitor is galangin. In certain embodiments the APP specific BACE inhibitor is rutin or a derivative thereof. In certain embodiments the APP specific BACE inhibitor is rutin.

In various embodiments ASBI prodrugs are provided. In certain embodiments the prodrug is a galangin prodrug that is processed to glangin when administered to a mammal. Illustrative galangin prodrug(s) include, but are not limited to, a galangin prodrug characterized by the formula:

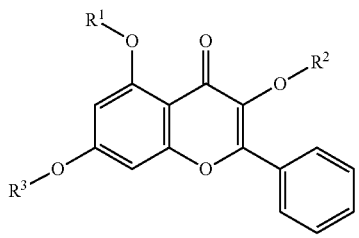

where $R^1$, $R^2$, and $R^3$ are H, or a protecting group that is removed in vivo in a mammal, where at least one of $R^1$, $R^2$, and $R^3$ is not H; and where the prodrug partially or completely inhibits BACE processing of APP when administered to a mammal. In certain embodiments least one of $R^1$, $R^2$, and $R^3$ are independently selected from the group consisting of

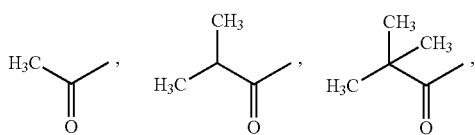

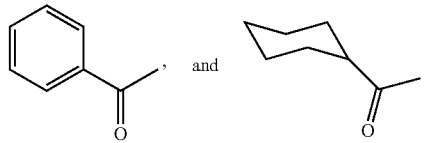

In certain embodiments $R^1$ is H and $R^2$ and $R^3$ are the same or different and comprise any combination of the groups shown above. In certain embodiments the prodrug has a formula shown in FIG. 1 and/or FIG. 2.

In certain embodiments, the ASBI and/or ASBI prodrug is provided as a pharmaceutical formulation where the ASBI and/or ASBI prodrug is the principle active component. In certain embodiments the ASBI and/or ASBI prodrug is the sole pharmaceutically active component (e.g., where the pharmaceutical activity is inhibition of BACE). In certain embodiments the ASBI and/or ASBI prodrug is provided in a pharmaceutical formulation where there is no other component is provided for neuropharmacological or neuropsychiatric activity.

In certain embodiments methods of preventing or delaying the onset of a pre-Alzheimer's condition and/or cognitive dysfunction, and/or ameliorating one or more symptoms of a pre-Alzheimer's condition and/or cognitive dysfunction, or preventing or delaying the progression of a pre-Alzheimer's condition or cognitive dysfunction to Alzheimer's disease, are provided. The methods typically comprise administering (or causing to be administered) to a subject in need thereof an APP specific BACE inhibitor (ASBI) and/or ASBI prodrug in an amount sufficient to prevent or delay the onset of a pre-Alzheimer's cognitive dysfunction, and/or to ameliorate one or more symptoms of a pre-Alzheimer's cognitive dysfunction, and/or to prevent or delay the progression of a pre-Alzheimer's cognitive dysfunction to Alzheimer's disease. In certain embodiments the ASBI and/or ASBI prodrug comprises an ASBI flavonoid and/or an ASBI prodrug as described herein (e.g., as described above). In certain embodiments the ASBI is galangin and/or the ASBI prodrug is a galangin prodrug. In certain embodiments the ASBI and/or ASBI prodrug (e.g., galangin and/or galangin prodrug) is administered in a pharmaceutical formulation wherein the ASBI is the principle active component. In certain embodiments the ASBI and/or ASBI prodrug (e.g., galangin and/or galangin prodrug) is administered in a pharmaceutical formulation where the ASBI and/or the ASBI prodrug is the sole pharmaceutically active component. In certain embodiments the ASBI and/or ASBI prodrug (e.g., galangin and/or galangin prodrug) is administered in a pharmaceutical formulation and no other agent is provided for neuropharmacological or neuropsychiatric activity. In certain embodiments the method is a method of preventing or delaying the transition from a cognitively asymptomatic pre-Alzheimer's condition to a pre-Alzheimer's cognitive dysfunction. In certain embodiments the method is a method of preventing or delaying the onset of a pre-Alzheimer's cognitive dysfunction. In certain embodiments the method comprises ameliorating one or more symptoms of a pre-Alzheimer's cognitive dysfunction. In certain embodiments the method comprises preventing or delaying the progression of a pre-Alzheimer's cognitive dysfunction to Alzheimer's disease. In certain embodiments the subject exhibits biomarker positivity of $A\beta$ in a clinically normal human subject age 50 or older, or 55 or older, or 60 or older, or 65 or older, or 70 or older, or 75 or older, or 80 or older. In certain embodiments the subject exhibits asymptomatic cerebral amyloidosis. In certain embodiments the subject exhibits cerebral amyloidosis in combination with downstream neurodegeneration. In certain embodiments the subject exhibits cerebral amyloidosis in combination with downstream neurodegeneration and subtle cognitive/behavioral decline. In certain embodiments the downstream neurodegeneration is determined by one or more elevated markers of neuronal injury selected from the group consisting of tau, and FDG uptake. In certain embodiments the cerebral amyloidosis is determined by PET, or CSF analysis, and/or structural MRI (sMRI). In certain embodiments the subject is a subject diagnosed with mild cognitive impairment. In certain embodiments the subject shows a clinical dementia rating above zero and below about 1.5. In certain embodiments the subject is human. In certain embodiments the subject is at risk of developing Alzheimer's disease. In certain embodiments the subject has a familial risk for having Alzheimer's disease. In certain embodiments the has a familial Alzheimer's disease (FAD) mutation. In certain embodiments the subject has the APOE 84 allele. In certain embodiments the administration of the ASBI and/or ASBI prodrug delays or prevents the progression of MCI to Alzheimer's disease. In certain embodiments the subject is free of and does not have genetic risk factors of Parkinson's disease or schizophrenia. In certain embodiments the subject is not diagnosed as having or at risk for Parkinson's disease or schizophrenia. In certain embodiments the subject is not diagnosed as at risk for a neurological disease or disorder other than Alzheimer's disease. In certain embodiments the administration produces a reduction in the CSF of levels of one or more components selected from the group consisting of total-Tau (tTau), phospho-Tau (pTau), APPneo, soluble Aβ40, pTau/Aβ42 ratio and tTau/Aβ42 ratio, and/or an increase in the CSF of levels of one or more components selected from the group consisting of Aβ42/Aβ40 ratio, Aβ42/Aβ38 ratio, sAPPα, sAPPα/sAPPβ ratio, sAPPα/Aβ40 ratio, and sAPPα/Aβ42 ratio. In certain embodiments the administration produces a reduction of the plaque load in the brain of the subject. In certain embodiments the administration produces a reduction in the rate of plaque formation in the brain of the subject. In certain embodiments the administration produces an improvement in the cognitive abilities of the subject. In certain embodiments the administration produces an improvement in, a stabilization of, or a reduction in the rate of decline of the clinical dementia rating (CDR) of the subject. In certain embodiments the subject is a human and the administration produces a perceived improvement in quality of life by the human. In certain embodiments the ASBI and/or ASBI prodrug is administered via a route selected from the group consisting of oral delivery, isophoretic delivery, transdermal delivery, parenteral delivery, aerosol administration, administration via inhalation, intravenous administration, topical administration to the eye, intraocular injection, and rectal administration. In certain embodiments the compound is administered orally. In certain embodiments the administering is over a period of at least three weeks, or over a period of at least 6 months, or over a period of at least one year. In certain embodiments the ASBI and/or ASBI prodrug is formulated for administration via a route selected from the group consisting of isophoretic delivery, transdermal delivery, aerosol administration, administration via inhalation, oral administration, intravenous administration, topical delivery to the eye, intraocular injection, and rectal administration. In certain embodiments the an acetylcholinesterase inhibitor (e.g., tacrineipidacrine, galantamine, donepezil, icopezil, zanapezil, rivastigmine, Namenda, huperzine A, phenserine, physostigmine, neostigmine, pyridostigmine, ambenonium, demarcarium, edrophonium, ladostigil and ungeremine, metrifonate, etc.) is not administered in conjunction with the ASBI and/or ASBI prodrug.

In various embodiments methods of ameliorating one or more symptoms of Alzheimer's disease, and/or reversing Alzheimer's disease, and/or reducing the rate of progression of Alzheimer's disease, are provided. The methods typically comprise administering to a subject in need thereof (or causing to be administered) an APP specific BACE inhibitor (ASBI) and/or an ASBI prodrug in an amount sufficient to ameliorate one or more symptoms of Alzheimer's disease, and/or to reverse Alzheimer's disease, and/or to reduce the rate of progression of Alzheimer's disease. In certain embodiments the ASBI and/or ASBI prodrug comprises an ASBI flavonoid and/or an ASBI prodrug as described herein (e.g., as described above). In certain embodiments the ASBI is galangin and/or the ASBI prodrug is a galangin prodrug (e.g., a prodrug shown in FIG. 1 and/or FIG. 2). In certain embodiments the ASBI and/or ASIB prodrug is administered in a pharmaceutical formulation where the ASBI and/or ASBI prodrug is the principle active component. In certain embodiments the ASBI and/or ASBI prodrug is administered in a pharmaceutical formulation where the ASBI and/or ASBI prodrug is the sole pharmaceutically active component. In certain embodiments the ASBI and/or ASBI prodrug is administered in a pharmaceutical formulation no other component is provided for neuropharmacological or neuropsychiatric activity. In certain embodiments the subject is a human (or a non-human mammal). In certain embodiments the subject is a human age 50 or older, or 55 or older, or 60 or older, or 65 or older, or 70 or older, or 75 or older, or 80 or older. In certain embodiments the subject is diagnosed with early stage Alzheimer's disease. In certain embodiments the subject is diagnosed with mid-stage Alzheimer's disease. In certain embodiments the subject is diagnosed with late-stage Alzheimer's disease. In certain embodiments the administering reduces the severity of Alzheimer's disease. In certain embodiments the administering ameliorates one or more symptoms of Alzheimer's disease. In certain embodiments the administering reduces the rate of progression of Alzheimer's disease. In certain embodiments the administering results in a reduction in the CSF of levels of one or more components selected from the group consisting of total-Tau (tTau), phospho-Tau (pTau), APPneo, soluble Aβ40, pTau/Aβ42 ratio and tTau/Aβ42 ratio, and/or an increase in the CSF of levels of one or more components selected from the group consisting of Aβ2/Aβ40 ratio, Aβ42/Aβ38 ratio, sAPPα, sAPPα/sAPPβ ratio, sAPPα/Aβ40 ratio, and sAPPα/Aβ42 ratio. is a method of preventing or delaying the transition from a cognitively asymptomatic pre-Alzheimer's condition to a pre-Alzheimer's cognitive dysfunction. In certain embodiments the administration produces a reduction of the plaque load in the brain of the subject. In certain embodiments the administration produces a reduction in the rate of plaque formation in the brain of the subject. In certain embodiments the administration produces an improvement in the cognitive abilities of the subject. In certain embodiments the administration produces an improvement in, a stabilization of, or a reduction in the rate of decline of the clinical dementia rating (CDR) of the subject. In certain embodiments the subject is a human and said administration produces a perceived improvement in quality of life by the human. In certain embodiments the administering results in reduced cerebral amyloidosis and/or downstream neurodegeneration. In certain embodiments the downstream neurodegeneration is determined by one or more markers of neuronal injury selected from the group consisting of tau, FDG uptake, decrease in sAPPalpha, increase in sAPPbeta, and Abeta. In certain embodiments the cerebral amyloidosis is determined by PET, CSF analysis. and structural MRI (sMRI). In certain embodiments the subject shows a clinical dementia rating indicative of Alzheimer's disease. In certain embodiments the subject has a familial risk for having Alzheimer's disease. In certain embodiments the subject has a familial Alzheimer's disease (FAD) mutation. In certain embodiments the subject has the APOE ε4 allele. In certain embodiments the subject is free of and does not have genetic risk factors of Parkinson's disease or schizophrenia. In certain embodiments the subject is not diagnosed as having or at risk for Parkinson's disease or schizophrenia. In certain embodiments the subject does not have a neurological disease or disorder other than Alzheimer's disease. In certain embodiments the subject is not diagnosed as having or at risk for a neurological disease or disorder other than Alzheimer's disease. In certain embodiments the ASBI and/or ASBI prodrug is administered via a route selected from the group consisting of oral delivery, isophoretic delivery, transdermal delivery, parenteral delivery, aerosol administration, administration via inhalation, intravenous administration, subcutaneous administration, topical administration to the eye, intraocular injection, and rectal administration. In certain embodiments the ASBI and/or ASBI prodrug is formulated for administration via a route selected from the group consisting of oral delivery, isophoretic delivery, transdermal delivery, parenteral delivery, aerosol administration, administration via inhalation, intravenous administration, and rectal administration. In certain embodiments the ASBI and/or ASBI prodrug is administered orally. In certain embodiments the administering is over a period of at least three weeks, or over a period of at least 6 months, or over a period of at least one year. In certain embodiments an acetylcholinesterase inhibitor (e.g., tacrineipidacrine, galantamine, donepezil, icopezil, zanapezil, rivastigmine, Namenda, huperzine A, phenserine, physostigmine, neostigmine, pyridostigmine, ambenonium, demarcarium, edrophonium, ladostigil and ungeremine, metrifonate, and the like) is not administered in conjunction with said ASBI and/or ASBI prodrug. In certain embodiments the ASBI and/or ASBI prodrug is administered via a route selected from the group consisting of oral delivery, isophoretic delivery, transdermal delivery, parenteral delivery, aerosol administration, administration via inhalation, intravenous administration, and rectal administration.

In various embodiments methods of slowing the progression, stopping, or reversing age-related macular degeneration (AMD) and/or glaucoma in a mammal are provided. The methods typically involve administering to the mammal an ASBI and/or an ASBI prodrug in an amount sufficient to slow the progression, to stop, or to reverse, and/or to ameliorate one or more symptoms and/or markers of said AMD and/or glaucoma. In certain embodiments the ASBI and/or ASBI prodrug comprises an ASBI flavonoid and/or an ASBI prodrug as described herein (e.g., as described above). In certain embodiments the ASBI is galangin and/or the ASBI prodrug is a galangin prodrug (e.g., a prodrug shown in FIG. 1 and/or FIG. 2). In certain embodiments the ASBI and/or ASBI prodrug is administered via a route selected from the group consisting of oral delivery, isophoretic delivery, transdermal delivery, parenteral delivery, aerosol administration, administration via inhalation, intravenous administration, subcutaneous administration, topical administration to the eye, intraocular injection, and rectal administration. In certain embodiments the ASBI and/or ASBI prodrug is formulated for administration via a route selected from the group consisting of oral delivery, isophoretic delivery, transdermal delivery, parenteral delivery, aerosol administration, administration via inhalation, intravenous administration, and rectal administration. In certain embodiments the ASBI and/or ASBI prodrug is administered to the eye (e.g., via eye drops, intraocular injection, and the like). In certain embodiments the administering is over a period of at least three weeks, or over a period of at least 6 months, or over a period of at least one year.

Definitions

Generally, reference to a certain element such as hydrogen or H is meant to include all isotopes of that element. For example, if an R group is defined to include hydrogen or H, it also includes deuterium and tritium. Accordingly, isotopically labeled compounds are within the scope of this invention.

In general, "substituted" refers to an organic group as defined below (e.g., an alkyl group) in which one or more bonds to a hydrogen atom contained therein are replaced by a bond to non-hydrogen or non-carbon atoms. Substituted groups also include groups in which one or more bonds to a carbon(s) or hydrogen(s) atom are replaced by one or more bonds, including double or triple bonds, to a heteroatom. Thus, a substituted group will be substituted with one or more substituents, unless otherwise specified. In some embodiments, a substituted group is substituted with 1, 2, 3, 4, 5, or 6 substituents. Examples of substituent groups include: halogens (i.e., F, Cl, Br, and I); hydroxyls; alkoxy, alkenoxy, alkynoxy, aryloxy, aralkyloxy, heterocyclyloxy, and heterocyclylalkoxy groups; carbonyls (oxo); carboxyls; esters; urethanes; oximes; hydroxylamines; alkoxyamines; aralkoxyamines; thiols; sulfides; sulfoxides; sulfones; sulfonyls; sulfonamides; amines; N-oxides; hydrazines; hydrazides; hydrazones; azides; amides; ureas; amidines; guanidines; enamines; imides; isocyanates; isothiocyanates; cyanates; thiocyanates; imines; nitro groups; nitriles (i.e., CN), and the like.

The term "alkyl" refers to and covers any and all groups that are known as normal alkyl, branched-chain alkyl, cycloalkyl and also cycloalkyl-alkyl. Illustrative alkyl groups include, but are not limited to methyl, ethyl, n-propyl, isopropyl, n-butyl, isobutyl, sec-butyl, t-butyl, octyl, and decyl. The term "cycloalkyl" refers to cyclic, including polycyclic, saturated hydrocarbyl groups. Examples include, but are not limited to cyclopentyl, cyclohexyl, dicyclopentyl, norbomyl, octahydronapthyl, and spiro[3.4]octyl. In certain embodiments, alkyl groups contain 1-12 carbon atoms (C1-12 alkyl), or 1-9 carbon atoms ($C_{1-9}$ alkyl), or 1-6 carbon atoms ($C_{1-6}$ alkyl), or 1-5 carbon atoms ($C_{1-5}$ alkyl), or carbon atoms ($C_{1-4}$ alkyl), or 1-3 carbon atoms ($C_{1-3}$ alkyl), or 1-2 carbon atoms ($C_{1-2}$ alkyl).

By way of example, the term "$C_{1-6}$ alkyl group" refers to a straight chain or branched chain alkyl group having 1 to 6 carbon atoms, and may be exemplified by a methyl group, an ethyl group, an n-propyl group, an isopropyl group, an n-butyl group, an isobutyl group, a tert-butyl group, a sec-butyl group, an n-pentyl group, a tert-amyl group, a 3-methylbutyl group, a neopentyl group, and an n-hexyl group.

The term "alkoxy" as used herein means an alkyl group bound through a single, terminal oxygen atom. An "alkoxy" group may be represented as —O-alkyl where alkyl is as defined above. The term "aryloxy" is used in a similar fashion, and may be represented as —O-aryl, with aryl as defined below. The term "hydroxy" refers to —OH.

Similarly, the term "alkylthio" as used herein means an alkyl group bound through a single, terminal sulfur atom. An "alkylthio" group may be represented as —S-alkyl where alkyl is as defined above. The term "arylthio" is used similarly, and may be represented as —S-aryl, with aryl as defined below. The term "mercapto" refers to —SH.

Aryl groups are cyclic aromatic hydrocarbons that do not contain heteroatoms. Aryl groups include monocyclic, bicyclic and polycyclic ring systems. Thus, aryl groups include, but are not limited to, phenyl, azulenyl, heptalenyl, biphenylenyl, indacenyl, fluorenyl, phenanthrenyl, triphenylenyl, pyrenyl, naphthacenyl, chrysenyl, biphenyl, anthracenyl, indenyl, indanyl, pentalenyl, and naphthyl groups. In some embodiments, aryl groups contain 6-14 carbons, and in others from 6 to 12 or even 6-10 carbon atoms in the ring portions of the groups. Although the phrase "aryl groups" includes groups containing fused rings, such as fused aromatic-aliphatic ring systems (e.g., indanyl, tetrahydronaphthyl, and the like), it does not include aryl groups that have other groups, such as alkyl or halo groups, bonded to one of the ring members. Rather, groups such as tolyl are referred to as substituted aryl groups. Representative substituted aryl groups may be mono-substituted or substituted more than once. For example, monosubstituted aryl groups include, but are not limited to, 2-, 3-, 4-, 5-, or 6-substituted phenyl or naphthyl groups, which may be substituted with substituents such as those listed above.

The term "heteroaryl group" refers to a monocyclic or condensed-ring aromatic heterocyclic group containing one or more hetero-atoms selected from 0, S and N. If the aromatic heterocyclic group has a condensed ring, it can include a partially hydrogenated monocyclic group. Examples of such a heteroaryl group include a pyrazolyl group, a thiazolyl group, an isothiazolyl group, a thiadiazolyl group, an imidazolyl group, a furyl group, a thienyl group, an oxazolyl group, an isoxazolyl group, a pyrrolyl group, an imidazolyl group, a (1,2,3)- and (1,2,4)-triazolyl group, a tetrazolyl group, a pyranyl group, a pyridyl group, a pyrimidinyl group, a pyrazinyl group, a pyridazinyl group, a quinolyl group, an isoquinolyl group, a benzofuranyl group, an isobenzofuranyl group, an indolyl group, an isoindolyl group, an indazolyl group, a benzoimidazolyl group, a benzotriazolyl group, a benzoxazolyl group, a benzothiazolyl group, a benzo[b]thiophenyl group, a thieno [2,3-b]thiophenyl group, a (1,2)- and (1,3)-benzoxathiol group, a chromenyl group, a 2-oxochromenyl group, a benzothiadiazolyl group, a quinolizinyl group, a phthalazinyl group, a naphthyridinyl group, a quinoxalinyl group, a quinazolinyl group, a cinnolinyl group, and a carbazolyl group.

A "derivative" of a compound means a chemically modified compound wherein the chemical modification takes place at one or more functional groups of the compound. The derivative however, is expected to retain, or enhance, the pharmacological activity of the compound from which it is derived.

As used herein, "administering" refers to local and systemic administration, e.g., including enteral, parenteral, pulmonary, and topical/transdermal administration. Routes of administration for agents (e.g., ASBIs such as galangin, rutin, and analogues, derivatives, or prodrugs thereof, or tautomer(s) or stereoisomer(s) thereof, or pharmaceutically acceptable salts or solvates of said ASBI(s), said stereoisomer(s), or said tautomer(s), or analogues, derivatives, or prodrugs thereof) that find use in the methods described herein include, e.g., oral (per os (p.o.)) administration, nasal or inhalation administration, administration as a suppository, topical contact, transdermal delivery (e.g., via a transdermal patch), intrathecal (IT) administration, intravenous ("iv") administration, intraperitoneal ("ip") administration, intramuscular ("im") administration, intralesional administration, or subcutaneous ("sc") administration, or the implantation of a slow-release device e.g., a mini-osmotic pump, a depot formulation, etc., to a subject. Administration can be by any route including parenteral and transmucosal (e.g., oral, nasal, vaginal, rectal, or transdermal). Parenteral administration includes, e.g., intravenous, intramuscular, intra-arterial, intradermal, subcutaneous, intraperitoneal, intraventricular, ionophoretic and intracranial. Other modes of delivery include, but are not limited to, the use of liposomal formulations, intravenous infusion, transdermal patches, etc.

The terms "systemic administration" and "systemically administered" refer to a method of administering the agent(s) described herein or composition to a mammal so that the agent(s) or composition is delivered to sites in the body, including the targeted site of pharmaceutical action, via the circulatory system. Systemic administration includes, but is not limited to, oral, intranasal, rectal and parenteral (e.g., other than through the alimentary tract, such as intramuscular, intravenous, intra-arterial, transdermal and subcutaneous) administration.

The term "co-administering" or "concurrent administration" or "administering in conjunction with" when used, for example with respect to the active agent(s) described herein e.g., ASBIs such as galangin, rutin, and analogues, derivatives, or prodrugs thereof) and a second active agent (e.g., a cognition enhancer), refers to administration of the agent(s) and/the second active agent such that both can simultaneously achieve a physiological effect. The two agents, however, need not be administered together. In certain embodiments, administration of one agent can precede administration of the other. Simultaneous physiological effect need not necessarily require presence of both agents in the circulation at the same time. However, in certain embodiments, co-administering typically results in both agents being simultaneously present in the body (e.g., in the plasma) at a significant fraction (e.g., 20% or greater, preferably 30% or 40% or greater, more preferably 50% or 60% or greater, most preferably 70% or 80% or 90% or greater) of their maximum serum concentration for any given dose.

The term "effective amount" or "pharmaceutically effective amount" refer to the amount and/or dosage, and/or dosage regime of one or more agent(s) necessary to bring about the desired result e.g., an amount sufficient to mitigating in a mammal one or more symptoms associated with mild cognitive impairment (MCI), or an amount sufficient to lessen the severity or delay the progression of a disease characterized by amyloid deposits in the brain in a mammal (e.g., therapeutically effective amounts), an amount sufficient to reduce the risk or delaying the onset, and/or reduce the ultimate severity of a disease characterized by amyloid deposits in the brain in a mammal (e.g., prophylactically effective amounts).

The phrase "cause to be administered" refers to the actions taken by a medical professional (e.g., a physician), or a person controlling medical care of a subject, that control and/or permit the administration of the agent(s) at issue to the subject. Causing to be administered can involve diagnosis and/or determination of an appropriate therapeutic or prophylactic regimen, and/or prescribing particular agent(s)

for a subject. Such prescribing can include, for example, drafting a prescription form, annotating a medical record, and the like.

As used herein, the terms "treating" and "treatment" refer to delaying the onset of, retarding or reversing the progress of, reducing the severity of, or alleviating or preventing either the disease or condition to which the term applies, or one or more symptoms of such disease or condition.

The term "mitigating" refers to reduction or elimination of one or more symptoms of that pathology or disease, and/or a reduction in the rate or delay of onset or severity of one or more symptoms of that pathology or disease, and/or the prevention of that pathology or disease. In certain embodiments, the reduction or elimination of one or more symptoms of pathology or disease can include, but is not limited to, reduction or elimination of one or more markers that are characteristic of the pathology or disease (e.g., of total-Tau (tTau), phospho-Tau (pTau), APPneo, soluble Aβ40, pTau/Aβ42 ratio and tTau/Aβ42 ratio, and/or an increase in the CSF of levels of one or more components selected from the group consisting of Aβ42/Aβ40 ratio, Aβ42/Aβ38 ratio, sAPPα, sAPPα/sAPPβ ratio, sAPPα/Aβ40 ratio, sAPPα/Aβ42 ratio, etc.) and/or reduction, stabilization or reversal of one or more diagnostic criteria (e.g., clinical dementia rating (CDR)).

As used herein, the phrase "consisting essentially of" refers to the genera or species of active pharmaceutical agents recited in a method or composition, and further can include other agents that, on their own do not substantial activity for the recited indication or purpose. In some embodiments, the phrase "consisting essentially of" expressly excludes the inclusion of one or more additional agents that have neuropharmacological activity other than the recited agent(s) (e.g., other than ASBIs such as galangin, rutin, and analogues, derivatives, or prodrugs thereof). In some embodiments, the phrase "consisting essentially of" expressly excludes the inclusion of one or more additional active agents other than the active agent(s) described herein (e.g., other than ASBIs such as galangin, rutin, and analogues, derivatives, or prodrugs thereof). In some embodiments, the phrase "consisting essentially of" expressly excludes the inclusion of one or more acetylcholinesterase inhibitors.

The terms "subject," "individual," and "patient" interchangeably refer to a mammal, preferably a human or a non-human primate, but also domesticated mammals (e.g., canine or feline), laboratory mammals (e.g., mouse, rat, rabbit, hamster, guinea pig) and agricultural mammals (e.g., equine, bovine, porcine, ovine). In various embodiments, the subject can be a human (e.g., adult male, adult female, adolescent male, adolescent female, male child, female child) under the care of a physician or other healthworker in a hospital, psychiatric care facility, as an outpatient, or other clinical context. In certain embodiments the subject may not be under the care or prescription of a physician or other healthworker.

The term "formulation" or "drug formulation" or "dosage form" or "pharmaceutical formulation" as used herein refers to a composition containing at least one therapeutic agent or medication for delivery to a subject. In certain embodiments the dosage form comprises a given "formulation" or "drug formulation" and may be administered to a patient in the form of a lozenge, pill, tablet, capsule, suppository, membrane, strip, liquid, patch, film, gel, spray or other form.

The term "mucosal membrane" refers generally to any of the mucus-coated biological membranes in the body. In certain embodiments active agent(s) described herein can be administered herein via any mucous membrane found in the body, including, but not limited to buccal, perlingual, nasal, sublingual, pulmonary, rectal, and vaginal mucosa. Absorption through the mucosal membranes of the oral cavity and those of the gut are of interest. Thus, peroral, buccal, sublingual, gingival and palatal absorption are contemplated herein.

The term "transmucosal" delivery of a drug and the like is meant to encompass all forms of delivery across or through a mucosal membrane.

The term "bioadhesion" as used herein refers to the process of adhesion of the dosage form(s) to a biological surface, e.g., mucosal membranes.

"Controlled drug delivery" refers to release or administration of a drug from a given dosage form in a controlled fashion in order to achieve the desired pharmacokinetic profile in vivo. An aspect of "controlled" drug delivery is the ability to manipulate the formulation and/or dosage form in order to establish the desired kinetics of drug release.

"Sustained drug delivery" refers to release or administration of a drug from a source (e.g., a drug formulation) in a sustained fashion over a protracted yet specific period of time, that may extend from several minutes to a few hours, days, weeks or months. In various embodiments the term "sustained" will be used to refer to delivery of consistent and/or substantially constant levels of drug over a time period ranging from a few minutes to a day, with a profile characterized by the absence of an immediate release phase, such as the one obtained from IV administration.

The term "$T_{max}$" as used herein means the time point of maximum observed plasma concentration.

The term "$C_{max}$" as used herein means the maximum observed plasma concentration.

The term "plasma $t_{1/2}$" as used herein means the observed "plasma half-life" and represents the time required for the drug plasma concentration to reach the 50% of its maximal value ($C_{max}$). This facilitates determination of the mean duration of pharmacological effects. In addition, it facilitates direct and meaningful comparisons of the duration of different test articles after delivery via the same or different routes.

The term "Optimal Therapeutic Targeting Ratio" or "OTTR" represents the average time that the drug is present at therapeutic levels, defined as time within which the drug plasma concentration is maintained above 50% of $C_{max}$ normalized by the drug's elimination half-life multiplied by the ratio of the $C_{max}$ obtained in the dosage form of interest over the $C_{max}$ following IV administration of equivalent doses and it is calculated by the formula:

$$OTTR=(C^{IV}_{max}/C_{max})\times(Dose/Dose^{IV})(\text{Time above } 50\% \text{ of } C_{max})/(\text{Terminal}^{IV} \text{ elimination half-life of the drug}).$$

BRIEF DESCRIPTION OF THE DRAWINGS

FIG. 7A: Potent transactivation of transcription was achieved with APP fused to the Gal4 DNA binding domain when both Mint3 and TAZ were present. This transactivation was inhibited by Galangin and BACE inhibitor IV. FIG. 7B: Potent transactivation of transcription was also achieved with APLP2 fused to the Gal4 DNA binding domain when both Mint3 and TAZ were present. This transactivation was inhibited by Galangin and BACE inhibitor IV. Diagrams exhibit experiments in which cells were co-transfected with a Gal4-luciferase reporter plasmid (to measure transactivation), a β-galactosidase plasmid (to normalize for transfection efficiency), and the test plasmids (Mint3, TAZ and APP-Gal4 or APLP2-Gal4). The normalized luciferase activity is expressed as a percentage of the DMSO treated control (FIGS. 7A, 7B). Error bars indicate SEM. (*, p<0.05; , p<0.01; *, p<0.001; n=3, student t test).

DETAILED DESCRIPTION

In certain embodiments bioflavonoid analogues are identified that that inhibit β-secretase mediated APP processing by a novel mechanism. In particular, it is believed these molecules inhibit the BACE cleavage of the MBP-C125 APP substrate, resulting in the inhibition of the production of C99 but not the β-site peptide substrate (P5-P5'). In addition, various bioflavonoids and analogues thereof identified herein inhibit sAPPβ in neuroblastoma SHSY5Y cells. Further it was demonstrated that the inhibitory activity is associated with binding to the MBP-C125 substrate. Accordingly, these molecules appear to be APP specific BACE inhibitors (ASBIs) and provide a new mechanism to modulate APP processing. These ASBIs can be used in the treatment and/or prophylaxis of pathologies characterized by pathological APP processing (e.g., Alzheimer's disease, pre-Alzheimer's conditions such as MCI or pre-symptomatic MCI, and the like).

The ASBIs are at least selective and appear to be specific for the APP substrate and are believed to show fewer undesired side-effects because the ASBIs are typically not active on other substrates for the enzyme. With respect to inhibitors of γ-secretase, substrates other than APP, such as Notch, raise concerns for potential side effects of γ-secretase inhibition, and the recent failure of the γ-secretase inhibitor, semagacestat, serves to reinforce such concerns. Similarly in the case of BACE, for example, inhibition of non-APP substrates such as PSGL1 or LRP can produce adverse side-effects. Therefore, the optimal BACE inhibitor would be one that would bind not to BACE but rather to APP, leading to APP-specific BACE inhibition (ASBI).

Figure 10:
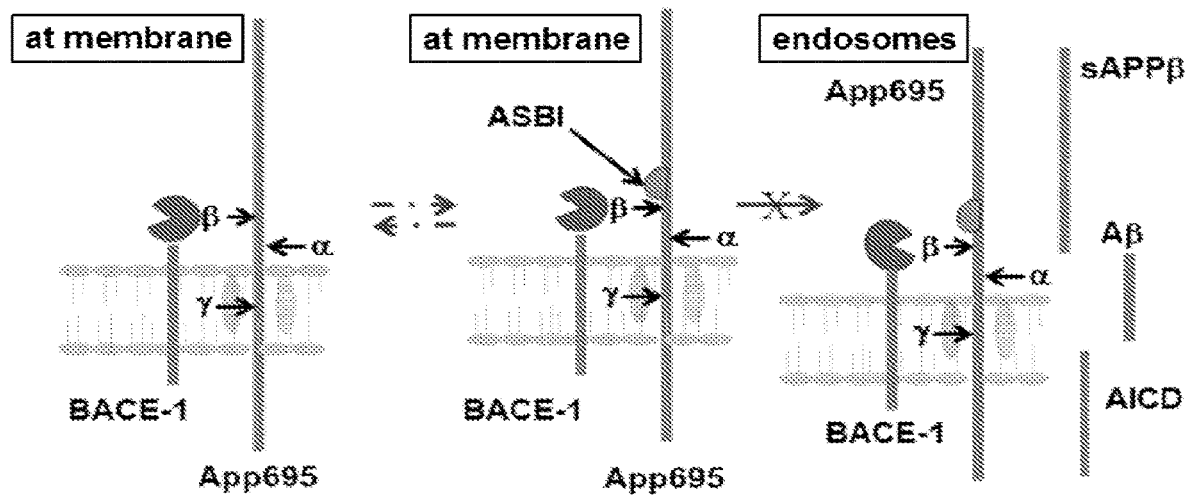
FIG. 10 illustrates a molecular-clamp model for ASBI activity.

Without being bound to a particular theory it is believed that such ASBIs would interact with APP or the APP-BACE complex ("inactive" complex) at the membrane and prevent its transition to the "active" complex in early endosomes, where at pH<5 BACE is fully active (see, e.g., FIG. 10). Some β-site binding antibodies have been shown to block the cleavage of APP by BACE and also work in animal models of AD, however for effective pharmaceutical development small organic molecules are typically preferred to relatively large biomolecules such as antibodies.

The data described herein on the identification of the first ASBIs, demonstrates that such an approach is feasible. APP-Specific-BACE-Inhibitors (ASBIs) inhibit the BACE cleavage of the Amyloid Precursor Protein (APP) but not the proteolytic cleavage of other substrates. Such therapeutics are believed to represent a new class of Alzheimer's disease (or other amyloidogenic disease) therapeutics.

Figure 1:
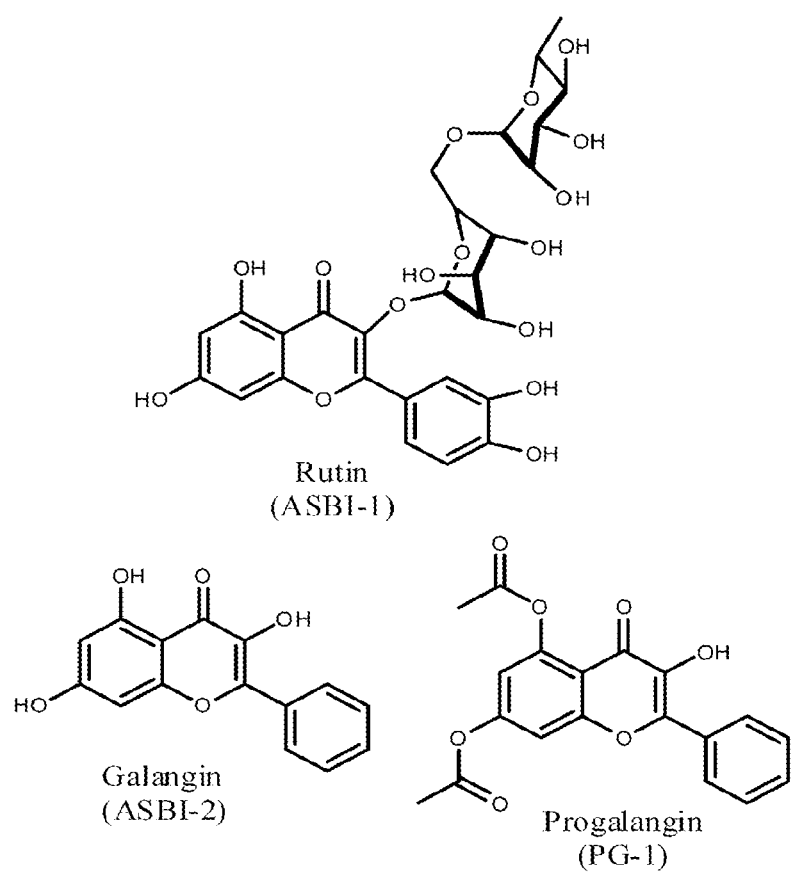
FIG. 1 shows the structure of rutin, galangin and progalangin-1.

Initially a clinical library of 448 compounds was screened and this assay led to the identification of a single bioflavonoid that specifically inhibited the MBP-C125 substrate of BACE while not preventing the cleavage of the P5-P5' substrate. This bioflavonoid Rutin (see, e.g., FIG. 1) is a nutritional supplement was also found to inhibit sAPPβ in cells. A panel of bioflavonoids was then tested in the ASBI and sAPPβ assay in cell culture. This testing identified a second bioflavonoid Galangin (see, e.g., FIG. 1) another nutritional supplement with known human use that was effective in the ASBI assay and in cells in preventing the BACE cleavage of APP. Galangin also has been reported to be an inhibitor of acetylcholine esterase (AChE). Using a simple nitrocellulose filter ligand-binding assay initial binding of various bioflavonoids to the MBP-C125 substrate was demonstrated. A panel of bioflavonoids were screened in the ASBI assay. Rutin and Galangin were identified as effective in modulating sAPPβ levels in cells and shows binding to the APP substrate (see Example 1).

Figure 7A:
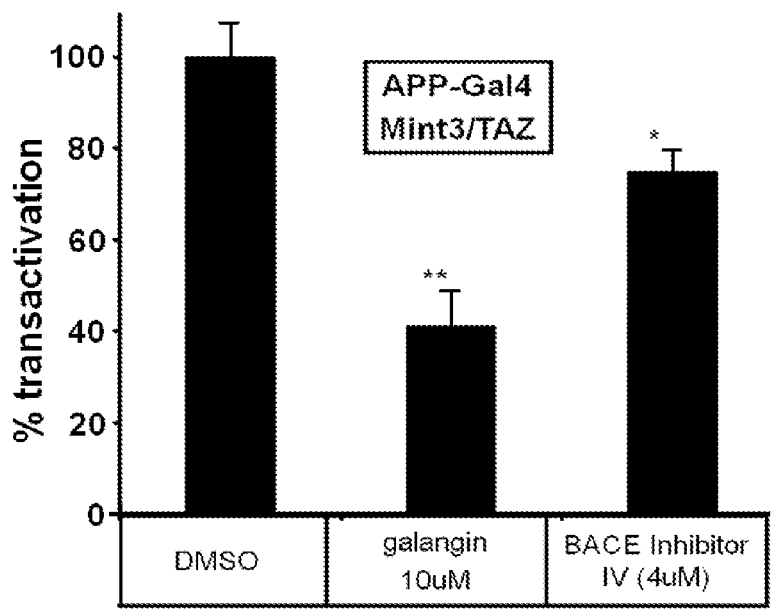
FIGS. 7A and 7B illustrate inhibition of APP-Gal4 and APLP2-Gal4 transactivation by galangin.
Figure 7B:
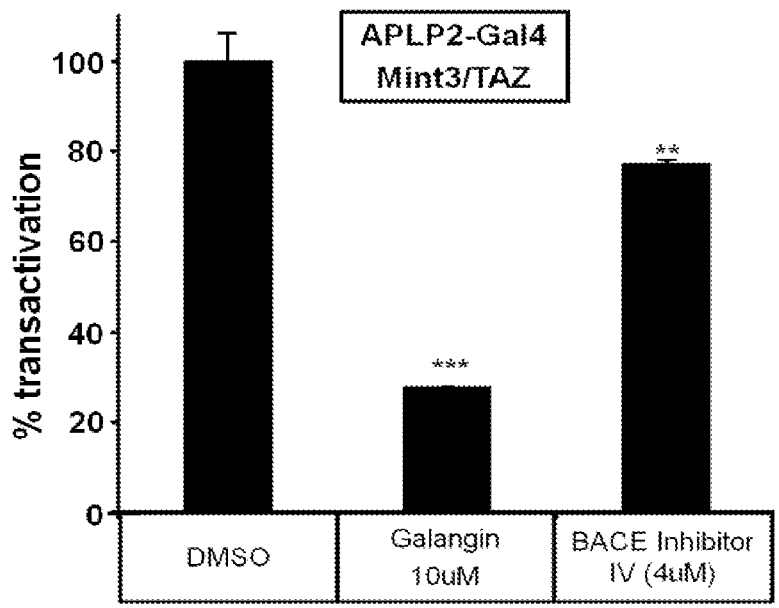

It was demonstrated that the bioflavonoids could inhibit BACE cleavage of APP and APLP2. A HEK-293 assay transfected with APP or APLP2-Gal4 to obtain this data. This assay system is described by Orcholski et al. (2011) *J. Alzheimers Dis.*, 23(4):689-699. Transactivation is achieved upon transfection with Mint3 and Taz. The ASBI was expected to inhibit only the transactivation of APP-Gal4, not that of APLP2-Gal4. For these experiments cells were co-transfected with a Gal4-luciferase reporter plasmid (to measure transactivation), a beta-galactosidase plasmid (to normalize for transfection efficiency), and the test plasmids identified. The normalized luciferase activity was expressed as fold induction over transcription by APP-Gal4 alone (FIG. 7A), or as fold induction over APLP2-Gal4 alone (FIG. 7B). Preliminary testing of galangin at 10 µM in this assay showed that it inhibits APP-Gal4 and APLP2-Ga14.

Initial pharmacokinetic evaluation of these two bioflavonoids in brain uptake assay using NTg mice showed that Rutin does not have any brain levels at 10 mpk after a sc dose, while Galangin did show significant brain levels (40 ng/g at 1 h) thus enabling its evaluation for proof-of-concept studies in the transgenic (Tg) mouse model. Treatment of the Tg mice were done by sc route at 100 mpk over 5 days. Galangin was then evaluated for its effect on sAPPα, and Aβ40 and Aβ42 (see Example 1). The reduction of Aβ levels was very encouraging in this study. Further increase in brain levels of galangin was possible using a prodrug of galangin (see, e.g., FIG. 1).

The examples provided herein indicate that certain bioflavanoids have the ability to bind APP and inhibit the BACE cleavage of APP and APLP2 thus suggest that they are APP specific BACE inhibitors. These molecules represent a new class of therapeutics for Alzheimer's disease that would be devoid of the potential toxicity from direct inhibition of BACE. Galangin was also shown to be effective in reducing Aβ40 and Aβ42 in the AD mouse model.

While Rutin was not effective in the mouse model it is believed this is due to difficulty passing the blood brain barrier. However, this does not mean that rutin and derivatives or analogues thereof are unsuitable for use in the methods described herein. Numerous methods for transporting a molecule through the blood brain barrier and/or for circumventing the blood brain barrier are known to those of skill in the art.

Typically mechanisms for drug targeting in the brain involve going either "through" or "behind" the BBB. In various embodiments modalities for drug delivery through the BBB entail its disruption by osmotic means; biochemically by the use of vasoactive substances such as bradykinin; or even by localized exposure to high-intensity focused ultrasound (HIFU) (see, e.g., McDannold et al. (2008) *Ultrasound in Medicine and Biology,* 34(5): 834-840). Other methods used to get through the BBB may entail the use of endogenous transport systems, including carrier-mediated transporters such as glucose and amino acid carriers; receptor-mediated transcytosis; and the blocking of active efflux transporters such as p-glycoprotein. Methods for drug delivery behind the BBB also include intracerebral implantation (such as with needles) and convection-enhanced distribution. In certain embodiments mMannitol can be used in bypassing the BBB. Nanoparticles can also help in the transfer of drugs across the BBB (see, e.g., Silva, (2008). *BMC Neuroscience,* 9:S4, and the like).

In view of the discovery of ASBI activity in Galangin and Rutin, similar activity is believed to exist in a number of additional bioflavonoid analogues described herein. Particular ASBI activity of any of these analogues can readily be further confirmed using, for example, the assays described above and illustrated in the Examples provided herein.

The sequential cleavage of APP by membrane-bound proteases β-secretase and γ-secretase results in the formation of Aβ. The β-Site APP cleavage enzyme-1 (BACE1) was identified as the major β-secretase activity that mediates the first cleavage of APP in the β-amyloidogenic pathway. In view of the ability of the ASBI compounds described herein to specifically block BACE1 activity at APP, it is believed (and the data presented herein show) that these ASBI compounds can lower Aβ levels or prevent the formation of the neurotoxic Aβ species. Accordingly, these compounds are believed to prevent or slow the progression of the disease and/or to prevent or slow the progression of pre-clinical manifestations of the amyloidogenic disease pathway.

Accordingly it is believed that these agents can be used to prevent or delay the onset of a pre-Alzheimer's cognitive dysfunction, and/or to ameliorate one or more symptoms of a pre-Alzheimer's cognitive dysfunction, and/or to prevent or delay the progression of a pre-Alzheimer's condition or cognitive dysfunction to Alzheimer's disease, and/or to promote the processing of amyloid precursor protein (APP) by the non-amyloidogenic pathway. In certain embodiments these agents can be used in the treatment of Alzheimer's disease (e.g., to lessen the severity of the disease, and/or to ameliorate one or more symptoms of the disease, and/or to slow the progression of the disease).

Therapeutic and Prophylactic Methods.

In various embodiments therapeutic and/or prophylactic methods are provided that utilize the active agent(s) (e.g., ASBIs such as galangin, rutin, and analogues, derivatives, or prodrugs thereof, or tautomer(s) or stereoisomer(s) thereof, or pharmaceutically acceptable salts or solvates of said ASBI(s), said stereoisomer(s), or said tautomer(s), or analogues, derivatives, or prodrugs thereof) are provided. Typically the methods involve administering one or more active agent(s) to a subject (e.g., to a human in need thereof) in an amount sufficient to realize the desired therapeutic or prophylactic result.

Prophylaxis

In certain embodiments active agent(s) (e.g., ASBIs such as galangin, rutin, and analogues, derivatives, or prodrugs thereof, or tautomer(s) or stereoisomer(s) thereof, or pharmaceutically acceptable salts or solvates of said ASBI(s), said stereoisomer(s), or said tautomer(s), or analogues, derivatives, or prodrugs thereof) are utilized in various prophylactic contexts. Thus, for example, ion certain embodiments, the active agent(s) can be used to prevent or delay the onset of a pre-Alzheimer's cognitive dysfunction, and/or to ameliorate one more symptoms of a pre-Alzheimer's condition and/or cognitive dysfunction, and/or to prevent or delaying the progression of a pre-Alzheimer's condition and/or cognitive dysfunction to Alzheimer's disease.

Accordingly in certain embodiments, the prophylactic methods described herein are contemplated for subjects identified as "at risk" and/or as having evidence of early Alzheimer's Disease (AD) pathological changes, but who do not meet clinical criteria for MCI or dementia. Without being bound to a particular theory, it is believed that even this "preclinical" stage of the disease represents a continuum from completely asymptomatic individuals with biomarker evidence suggestive of AD-pathophysiological process(es) (abbreviated as AD-P, see, e.g., Sperling et. al. (2011) *Alzheimer's & Dementia,* 1-13) at risk for progression to AD dementia to biomarker-positive individuals who are already demonstrating very subtle decline but not yet meeting standardized criteria for MCI (see, e.g., Albert et al. (2011) *Alzheimer's and Dementia,* 1-10 (doi:10.1016/j.jalz.2011.03.008).

This latter group of individuals might be classified as "Not normal, not MCI" but would be can be designated "pre-symptomatic" or "pre-clinical or "asymptomatic" or "premanifest"). In various embodiments this continuum of pre-symptomatic AD can also encompass (1) individuals who carry one or more apolipoprotein E (APOE) 84 alleles who are known or believed to have an increased risk of developing AD dementia, at the point they are AD-P biomarker-positive, and (2) carriers of autosomal dominant mutations, who are in the presymptomatic biomarker-positive stage of their illness, and who will almost certainly manifest clinical symptoms and progress to dementia.

A biomarker model has been proposed in which the most widely validated biomarkers of AD-P become abnormal and likewise reach a ceiling in an ordered manner (see, e.g., Jack et al. (2010) *Lancet Neurol.*, 9: 119-128.). This biomarker model parallels proposed pathophysiological sequence of (pre-AD/AD), and is relevant to tracking the preclinical (asymptomatic) stages of AD (see, e.g., FIG. 3 in Sperling et al. (2011) *Alzheimer's & Dementia*, 1-13). Biomarkers of brain amyloidosis include, but are not limited to reductions in CSF $A\beta_{42}$ and increased amyloid tracer retention on positron emission tomography (PET) imaging. Elevated CSF tau is not specific to AD and is thought to be a biomarker of neuronal injury. Decreased fluorodeoxyglucose 18F (FDG) uptake on PET with a temporoparietal pattern of hypometabolism is a biomarker of AD-related synaptic dysfunction. Brain atrophy on structural magnetic resonance imaging (MRI) in a characteristic pattern involving the medial temporal lobes, paralimbic and temporoparietal cortices is a biomarker of AD-related neurodegeneration. Other markers include, but are not limited to volumetric MRI, FDG-PET, or plasma biomarkers (see, e.g., Vemuri et al. (2009) *Neurology*, 73: 294-301; Yaffe et al. (2011) *JAMA* 305: 261-266).

In certain embodiments the subjects suitable for the prophylactic methods contemplated herein include, but are not limited to subject characterized as having asymptomatic cerebral amyloidosis. In various embodiments these individuals have biomarker evidence of $A\beta$ accumulation with elevated tracer retention on PET amyloid imaging and/or low $A\beta42$ in CSF assay, but typically no detectable evidence of additional brain alterations suggestive of neurodegeneration or subtle cognitive and/or behavioral symptomotology.

It is noted that currently available CSF and PET imaging biomarkers of $A\beta$ primarily provide evidence of amyloid accumulation and deposition of fibrillar forms of amyloid. Data suggest that soluble or oligomeric forms of $A\beta$ are likely in equilibrium with plaques, which may serve as reservoirs. In certain embodiments it is contemplated that there is an identifiable preplaque stage in which only soluble forms of $A\beta$ are present. In certain embodiments it is contemplated that oligomeric forms of amyloid may be critical in the pathological cascade, and provide useful markers. In addition, early synaptic changes may be present before evidence of amyloid accumulation.

In certain embodiments the subjects suitable for the prophylactic methods contemplated herein include, but are not limited to, subjects characterized as amyloid positive with evidence of synaptic dysfunction and/or early neurodegeneration. In various embodiments these subjects have evidence of amyloid positivity and presence of one or more markers of "downstream" AD-P-related neuronal injury. Illustrative, but non-limiting markers of neuronal injury include, but are not limited to (1) elevated CSF tau or phospho-tau, (2) hypometabolism in an AD-like pattern (i.e., posterior cingulate, precuneus, and/or temporoparietal cortices) on FDG-PET, and (3) cortical thinning/gray matter loss in a specific anatomic distribution (i.e., lateral and medial parietal, posterior cingulate, and lateral temporal cortices) and/or hippocampal atrophy on volumetric MRI. Other markers include, but are not limited to fMRI measures of default network connectivity. In certain embodiments early synaptic dysfunction, as assessed by functional imaging techniques such as FDG-PET and fMRI, can be detectable before volumetric loss. Without being bound to a particular theory, it is believed that amyloid-positive individuals with evidence of early neurodegeneration may be farther down the trajectory (i.e., in later stages of preclinical (asymptomatic) AD).

In certain embodiments the subjects suitable for the prophylactic methods contemplated herein include, but are not limited to, subjects characterized as amyloid positive with evidence of neurodegeneration and subtle cognitive decline. Without being bound to a particular theory, it is believed that those individuals with biomarker evidence of amyloid accumulation, early neurodegeneration, and evidence of subtle cognitive decline are in the last stage of preclinical (asymptomatic) AD, and are approaching the border zone with clinical criteria for mild cognitive impairment (MCI). These individuals may demonstrate evidence of decline from their own baseline (particularly if proxies of cognitive reserve are taken into consideration), even if they still perform within the "normal" range on standard cognitive measures. Without being bound to a particular theory, it is believed that more sensitive cognitive measures, particularly with challenging episodic memory measures, may detect very subtle cognitive impairment in amyloid-positive individuals. In certain embodiments criteria include, but are not limited to, self-complaint of memory decline or other subtle neurobehavioral changes.

As indicated above, subjects/patients amenable to prophylactic methods described herein include individuals at risk of disease (e.g., a pathology characterized by amyloid plaque formation such as MCI) but not showing symptoms, as well as subjects presently showing certain symptoms or markers. It is known that the risk of MCI and later Alzheimer's disease generally increases with age. Accordingly, in asymptomatic subjects with no other known risk factors, in certain embodiments, prophylactic application is contemplated for subjects over 50 years of age, or subjects over 55 years of age, or subjects over 60 years of age, or subjects over 65 years of age, or subjects over 70 years of age, or subjects over 75 years of age, or subjects over 80 years of age, in particular to prevent or slow the onset or ultimate severity of mild cognitive impairment (MCI), and/or to slow or prevent the progression from MCI to early stage Alzheimer's disease (AD).

In certain embodiments, the methods described herein present methods are especially useful for individuals who do have a known genetic risk of Alzheimer's disease (or other amyloidogenic pathologies), whether they are asymptomatic or showing symptoms of disease. Such individuals include those having relatives who have experienced MCI or AD (e.g., a parent, a grandparent, a sibling), and those whose risk is determined by analysis of genetic or biochemical markers. Genetic markers of risk toward Alzheimer's disease include, for example, mutations in the APP gene, particularly mutations at position 717 and positions 670 and 671 referred to as the Hardy and Swedish mutations respectively (see Hardy (1997) *Trends. Neurosci.*, 20: 154-159). Other markers of risk include mutations in the presenilin genes (PS1 and PS2), family history of AD, having the familial Alzheimer's disease (FAD) mutation, the APOE ε4 allele, hypercholesterolemia or atherosclerosis. Further susceptibility genes for the development of Alzheimer's disease are reviewed, e.g., in Sleegers, et al. (2010) *Trends Genet.* 26(2): 84-93.

In some embodiments, the subject is asymptomatic but has familial and/or genetic risk factors for developing MCI or Alzheimer's disease. In asymptomatic patients, treatment can begin at any age (e.g., 20, 30, 40, 50 years of age).

Usually, however, it is not necessary to begin treatment until a patient reaches at least about 40, 50, 60 or 70 years of age.

In some embodiments, the subject is exhibiting symptoms, for example, of mild cognitive impairment (MCI) or Alzheimer's disease (AD). Individuals presently suffering from Alzheimer's disease can be recognized from characteristic dementia, as well as the presence of risk factors described above. In addition, a number of diagnostic tests are available for identifying individuals who have AD. These include measurement of CSF Tau, phospho-tau (pTau), Aβ42 levels and C-terminally cleaved APP fragment (APPneo). Elevated total-Tau (tTau), phospho-Tau (pTau), APPneo, soluble Aβ40, pTau/Aβ42 ratio and tTau/Aβ42 ratio, and decreased Aβ42 levels, Aβ42/Aβ40 ratio, Aβ42/Aβ38 ratio, sAPPα levels, sAPPα/sAPPβ ratio, sAPPα/Aβ40 ratio, and sAPPα/Aβ42 ratio signify the presence of AD. In some embodiments, the subject or patient is diagnosed as having MCI. Increased levels of neural thread protein (NTP) in urine and/or increased levels of α2-macroglobulin (α2M) and/or complement factor H (CFH) in plasma are also biomarkers of MCI and/or AD (see, e.g., Anoop et al. (2010) Int. Alzheimer's Dis.2010:606802).

In certain embodiments, subjects amenable to treatment may have age-associated memory impairment (AAMI), or mild cognitive impairment (MCI). The methods described herein are particularly well-suited to the prophylaxis and/or treatment of MCI. In such instances, the methods can delay or prevent the onset of MCI, and or reduce one or more symptoms characteristic of MCI and/or delay or prevent the progression from MCI to early-, mid- or late-stage Alzheimer's disease or reduce the ultimate severity of the disease.

Mild Cognitive Impairment (MCI)

Mild cognitive impairment (MCI, also known as incipient dementia, or isolated memory impairment) is a diagnosis given to individuals who have cognitive impairments beyond that expected for their age and education, but that typically do not interfere significantly with their daily activities (see, e.g., Petersen et al. (1999) Arch. Neurol. 56(3): 303-308). It is considered in many instances to be a boundary or transitional stage between normal aging and dementia. Although MCI can present with a variety of symptoms, when memory loss is the predominant symptom it is termed "amnestic MCI" and is frequently seen as a risk factor for Alzheimer's disease (see, e.g., Grundman et al. (2004) Arch. Neurol. 61(1): 59-66; and on the internet at en.wikipedia.org/wiki/Mild_cognitive_impairment-cite note_Grundman-1). When individuals have impairments in domains other than memory it is often classified as non-amnestic single- or multiple-domain MCI and these individuals are believed to be more likely to convert to other dementias (e.g. dementia with Lewy bodies). There is evidence suggesting that while amnestic MCI patients may not meet neuropathologic criteria for Alzheimer's disease, patients may be in a transitional stage of evolving Alzheimer's disease; patients in this hypothesized transitional stage demonstrated diffuse amyloid in the neocortex and frequent neurofibrillary tangles in the medial temporal lobe (see, e.g., Petersen et al. (2006) Arch. Neurol. 63(5): 665-72).

The diagnosis of MCI typically involves a comprehensive clinical assessment including clinical observation, neuroimaging, blood tests and neuropsychological testing. In certain embodiments diagnostic criteria for MIC include, but are not limited to those described by Albert et al. (2011) Alzheimer's & Dementia. 1-10. As described therein, diagnostic criteria include (1) core clinical criteria that could be used by healthcare providers without access to advanced imaging techniques or cerebrospinal fluid analysis, and (2) research criteria that could be used in clinical research settings, including clinical trials. The second set of criteria incorporate the use of biomarkers based on imaging and cerebrospinal fluid measures. The final set of criteria for mild cognitive impairment due to AD has four levels of certainty, depending on the presence and nature of the biomarker findings.

In certain embodiments clinical evaluation/diagnosis of MCI involves: (1) Concern reflecting a change in cognition reported by patient or informant or clinician (i.e., historical or observed evidence of decline over time); (2) Objective evidence of Impairment in one or more cognitive domains, typically including memory (i.e., formal or bedside testing to establish level of cognitive function in multiple domains); (3) Preservation of independence in functional abilities; (4) Not demented; and in certain embodiments, (5) An etiology of MCI consistent with AD pathophysiological processes. Typically vascular, traumatic, medical causes of cognitive decline, are ruled out where possible. In certain embodiments, evidence of longitudinal decline in cognition is identified, when feasible. Diagnosis is reinforced by a history consistent with AD genetic factors, where relevant.

With respect to impairment in cognitive domain(s), there should be evidence of concern about a change in cognition, in comparison with the person's previous level. There should be evidence of lower performance in one or more cognitive domains that is greater than would be expected for the patient's age and educational background. If repeated assessments are available, then a decline in performance should be evident over time. This change can occur in a variety of cognitive domains, including memory, executive function, attention, language, and visuospatial skills. An impairment in episodic memory (i.e., the ability to learn and retain new information) is seen most commonly in MCI patients who subsequently progress to a diagnosis of AD dementia.

With respect to preservation of independence in functional abilities, it is noted that persons with MCI commonly have mild problems performing complex functional tasks which they used to perform shopping. They may take more time, be less efficient, and make more errors at performing such activities than in the past. Nevertheless, they generally maintain their independence of function in daily life, with minimal aids or assistance.

With respect to dementia, the cognitive changes should be sufficiently mild that there is no evidence of a significant impairment in social or occupational functioning. If an individual has only been evaluated once, change will be inferred from the history and/or evidence that cognitive performance is impaired beyond what would have been expected for that individual.

Cognitive testing is optimal for objectively assessing the degree of cognitive impairment for an individual. Scores on cognitive tests for individuals with MCI are typically 1 to 1.5 standard deviations below the mean for their age and education matched peers on culturally appropriate normative data (i.e., for the impaired domain(s), when available).

Episodic memory (i.e., the ability to learn and retain new information) is most commonly seen in MCI patients who subsequently progress to a diagnosis of AD dementia. There are a variety of episodic memory tests that are useful for identifying those MCI patients who have a high likelihood of progressing to AD dementia within a few years. These tests typically assess both immediate and delayed recall, so that it is possible to determine retention over a delay. Many, although not all, of the tests that have proven useful in this regard are wordlist learning tests with multiple trials. Such tests reveal the rate of learning over time, as well as the maximum amount acquired over the course of the learning trials. They are also useful for demonstrating that the individual is, in fact, paying attention to the task on immediate recall, which then can be used as a baseline to assess the relative amount of material retained on delayed recall. Examples of such tests include (but are not limited to: the Free and Cued Selective Reminding Test, the Rey Auditory Verbal Learning Test, and the California Verbal Learning Test. Other episodic memory measures include, but are not limited to: immediate and delayed recall of a paragraph such as the Logical Memory I and II of the Wechsler Memory Scale Revised (or other versions) and immediate and delayed recall of nonverbal materials, such as the Visual Reproduction subtests of the Wechsler Memory Scale-Revised I and II.

Because other cognitive domains can be impaired among individuals with MCI, it is desirable to examine domains in addition to memory. These include, but are not limited to executive functions (e.g., set-shifting, reasoning, problem-solving, planning), language (e.g., naming, fluency, expressive speech, and comprehension), visuospatial skills, and attentional control (e.g., simple and divided attention). Many clinical neuropsychological measures are available to assess these cognitive domains, including (but not limited to the Trail Making Test (executive function), the Boston Naming Test, letter and category fluency (language), figure copying (spatial skills), and digit span forward (attention).

As indicated above, genetic factors can be incorporated into the diagnosis of MCI. If an autosomal dominant form of AD is known to be present (i.e., mutation in APP, PS1, PS2), then the development of MCI is most likely the predursor to AD dementia. The large majority of these cases develop early onset AD (i.e., onset below 65 years of age).

In addition, there are genetic influences on the development of late onset AD dementia. For example, the presence of one or two ε4 alleles in the apolipoprotein E (APOE) gene is a genetic variant broadly accepted as increasing risk for late-onset AD dementia. Evidence suggests that an individual who meets the clinical, cognitive, and etiologic criteria for MCI, and is also APOE ε4 positive, is more likely to progress to AD dementia within a few years than an individual without this genetic characteristic. It is believed that additional genes play an important, but smaller role than APOE and also confer changes in risk for progression to AD dementia (see, e.g., Bertram et al. (2010) *Neuron,* 21: 270-281).

In certain embodiments subjects suitable for the prophylactic methods described herein include, but need not be limited to subjects identified having one or more of the core clinical criteria described above and/or subjects identified with one or more "research criteria" for MCI, e.g., as described below.

"Research criteria" for the identification/prognosis of MCI include, but are not limited to biomarkers that increase the likelihood that MCI syndrome is due to the pathophysiological processes of AD. Without being bound to a particular theory, it is believed that the conjoint application of clinical criteria and biomarkers can result in various levels of certainty that the MCI syndrome is due to AD pathophysiological processes. In certain embodiments, two categories of biomarkers have been the most studied and applied to clinical outcomes are contemplated. These include "Aβ" (which includes CSF Aβ$_{42}$ and/or PET amyloid imaging) and "biomarkers of neuronal injury" (which include, but are not limited to CSF tau/p-tau, hippocampal, or medial temporal lobe atrophy on MRI, and temporoparietal/precuneus hypometabolism or hypoperfusion on PET or SPECT).

Without being bound to a particular theory, it is believed that evidence of both Aβ, and neuronal injury (either an increase in tau/p-tau or imaging biomarkers in a topographical pattern characteristic of AD), together confers the highest probability that the AD pathophysiological process is present. Conversely, if these biomarkers are negative, this may provide information concerning the likelihood of an alternate diagnosis. It is recognized that biomarker findings may be contradictory and accordingly any biomarker combination is indicative (an indicator) used on the context of a differential diagnosis and not itself dispositive. It is recognized that varying severities of an abnormality may confer different likelihoods or prognoses, that are difficult to quantify accurately for broad application.

For those potential MCI subjects whose clinical and cognitive MCI syndrome is consistent with AD as the etiology, the addition of biomarker analysis effects levels of certainty in the diagnosis. In the most typical example in which the clinical and cognitive syndrome of MCI has been established, including evidence of an episodic memory disorder and a presumed degenerative etiology, the most likely cause is the neurodegenerative process of AD. However, the eventual outcome still has variable degrees of certainty. The likelihood of progression to AD dementia will vary with the severity of the cognitive decline and the nature of the evidence suggesting that AD pathophysiology is the underlying cause. Without being bound to a particular theory it is believed that positive biomarkers reflecting neuronal injury increase the likelihood that progression to dementia will occur within a few years and that positive findings reflecting both Ab accumulation and neuronal injury together confer the highest likelihood that the diagnosis is MCI due to AD.

A positive Aβ biomarker and a positive biomarker of neuronal injury provide an indication that the MCI syndrome is due to AD processes and the subject is well suited for the methods described herein.

A positive Aβ biomarker in a situation in which neuronal injury biomarkers have not been or cannot be tested or a positive biomarker of neuronal injury in a situation in which Aβ biomarkers have not been or cannot be tested indicate an intermediate likelihood that the MCI syndrome is due to AD. Such subjects are believed to be is well suited for the methods described herein Negative biomarkers for both Aβ and neuronal injury suggest that the MCI syndrome is not due to AD. In such instances the subjects may not be well suited for the methods described herein.

There is evidence that magnetic resonance imaging can observe deterioration, including progressive loss of gray matter in the brain, from mild cognitive impairment to full-blown Alzheimer disease (see, e.g., Whitwell et al. (2008) *Neurology* 70(7): 512-520). A technique known as PiB PET imaging is used to clearly show the sites and shapes of beta amyloid deposits in living subjects using a C11 tracer that binds selectively to such deposits (see, e.g., Jack et al. (2008) *Brain* 131(Pt 3): 665-680).

In certain embodiments, MCI is typically diagnosed when there is 1) Evidence of memory impairment; 2) Preservation of general cognitive and functional abilities; and 3) Absence of diagnosed dementia.

In certain embodiments MCI and stages of Alzheimer's disease can be identified/categorized, in part by Clinical Dementia Rating (CDR) scores. The CDR is a five point scale used to characterize six domains of cognitive and functional performance applicable to Alzheimer disease and related dementias: Memory, Orientation, Judgment & Problem Solving, Community Affairs, Home & Hobbies, and Personal Care. The necessary information to make each rating is obtained through a semi-structured interview of the patient and a reliable informant or collateral source (e.g., family member).

The CDR table provides descriptive anchors that guide the clinician in making appropriate ratings based on interview data and clinical judgment. In addition to ratings for each domain, an overall CDR score may be calculated through the use of an algorithm. This score is useful for characterizing and tracking a patient's level of impairment/dementia: 0=Normal; 0.5=Very Mild Dementia; 1=Mild Dementia; 2=Moderate Dementia; and 3=Severe Dementia. An illustrative CDR table is shown in Table 1.

TABLE 1

Illustrative clinical dementia rating (CDR) table.

| | Impairment: | | | | |
|---|---|---|---|---|---|
| | None | Questionable | Mild | Moderate | Severe |
| | | | CDR: | | |
| | 0 | 0.5 | 1 | 2 | 3 |
| Memory | No memory loss or slight inconsistent forgetfulness | Consistent slight forgetfulness; partial recollection of events' "benign" forgetfulness | Moderate memory loss; more marked for recent events; defect interferes with everyday activities | Severe memory loss; only highly learned material retained; new material rapidly lost | Severe memory loss; only fragments remain |
| Orientation | Fully oriented | Fully oriented except for slight difficulty with time relationships | Moderate difficulty with time relationships; oriented for place at examination; may have geographic disorientation elsewhere | Severe difficulty with time relationships; usually disoriented to time, often to place. | Oriented to person only |
| Judgment & Problem Solving | Solves everyday problems & handles business & financial affairs well; judgment good in relation to past performance | Slight impairment in solving problems, similarities, and differences | Moderate difficulty in handling problems, similarities and differences; social judgment usually maintained | Severely impaired in handling problems, similarities and differences; social judgment usually impaired | Unable to make judgments or solve problems |
| Community Affairs | Independent function at usual level in job, shopping, volunteer, and social groups | Slight impairment in these activities | Unable to function independently at these activities although may still be engaged in some; appears normal to casual inspection | No pretense of independent function outside of home Appears well enough to be taken to functions outside a family home | Appears too ill to be taken to functions outside a family home. |
| Home and Hobbies | Life at home, hobbies, and intellectual interests well maintained | Life at home, hobbies, and intellectual interests slightly impaired | Mild bit definite impairment of function at home; more difficult chores abandoned; more complicated hobbies and interests abandoned | Only simple chores preserved; very restricted interests, poorly maintained | No significant function in home |

TABLE 1-continued

Illustrative clinical dementia rating (CDR) table.

| | Impairment: | | | | |
|---|---|---|---|---|---|
| | None | Questionable | Mild | Moderate | Severe |
| | | | CDR: | | |
| | 0 | 0.5 | 1 | 2 | 3 |
| Personal Care | Fully capable of self-care | | Needs prompting | Requires assistance in dressing, hygiene, keeping of personal effects | Requires much help with personal care; frequent incontinence |

A CDR rating of ~0.5 or ~0.5 to 1.0 is often considered clinically relevant MCI. Higher CDR ratings can be indicative of progression into Alzheimer's disease.

In certain embodiments administration of one or more agents described herein (e.g., ASBIs such as galangin, rutin, and analogues, derivatives, or prodrugs thereof, or tautomer(s) or stereoisomer(s) thereof, or pharmaceutically acceptable salts or solvates of said ASBI(s), said stereoisomer(s), or said tautomer(s), or analogues, derivatives, or prodrugs thereof) is deemed effective when there is a reduction in the CSF of levels of one or more components selected from the group consisting of Tau, phospho-Tau (pTau), APPnco, soluble Aβ40, soluble Aβ42, and/or Aβ42/Aβ40 ratio, and/or when there is a reduction of the plaque load in the brain of the subject, and/or when there is a reduction in the rate of plaque formation in the brain of the subject, and/or when there is an improvement in the cognitive abilities of the subject, and/or when there is a perceived improvement in quality of life by the subject, and/or when there is a significant reduction in clinical dementia rating (CDR), and/or when the rate of increase in clinical dementia rating is slowed or stopped and/or when the progression from MCI to early stage AD is slowed or stopped.

In some embodiments, a diagnosis of MCI can be determined by considering the results of several clinical tests. For example, Grundman, et al., *Arch Neural* (2004) 61:59-66, report that a diagnosis of MCI can be established with clinical efficiency using a simple memory test (paragraph recall) to establish an objective memory deficit, a measure of general cognition (Mini-Mental State Exam (MMSE), discussed in greater detail below) to exclude a broader cognitive decline beyond memory, and a structured clinical interview (CDR) with patients and caregivers to verify the patient's memory complaint and memory loss and to ensure that the patient was not demented. Patients with MCI perform, on average, less than 1 standard deviation (SD) below normal on nonmemorycognitive measures included in the battery. Tests of learning, attention, perceptual speed, category fluency, and executive function may be impaired in patients with MCI, but these are far less prominent than the memory deficit.

Alzheimer's Disease (AD).

In certain embodiments the active agent(s) (e.g., ASBIs such as galangin, rutin, and analogues, derivatives, or prodrugs thereof, or tautomer(s) or stereoisomer(s) thereof, or pharmaceutically acceptable salts or solvates of said ASBI (s), said stereoisomer(s), or said tautomer(s), or analogues, derivatives, or prodrugs thereof) and/or formulations thereof are contemplated for the treatment of Alzheimer's disease. In such instances the methods described herein are useful in preventing or slowing the onset of Alzheimer's disease (AD), in reducing the severity of AD when the subject has transitioned to clinical AD diagnosis, and/or in mitigating one or more symptoms of Alzheimer's disease.

In particular, where the Alzheimer's disease is early stage, the methods can reduce or eliminate one or more symptoms characteristic of AD and/or delay or prevent the progression from MCI to early or later stage Alzheimer's disease.

Individuals presently suffering from Alzheimer's disease can be recognized from characteristic dementia, as well as the presence of risk factors described above. In addition, a number of diagnostic tests are available for identifying individuals who have AD. Individuals presently suffering from Alzheimer's disease can be recognized from characteristic dementia, as well as the presence of risk factors described above. In addition, a number of diagnostic tests are available for identifying individuals who have AD. These include measurement of CSF Tau, phospho-tau (pTau), sAPPα, sAPPβ, Aβ40, Aβ42 levels and/or C terminally cleaved APP fragment (APPneo). Elevated Tau, pTau, sAPPβ and/or APPneo, and/or decreased sAPPα, soluble Aβ40 and/or soluble Aβ42 levels, particularly in the context of a differential diagnosis, can signify the presence of AD.

In certain embodiments subjects amenable to treatment may have Alzheimer's disease. Individuals suffering from Alzheimer's disease can also be diagnosed by Alzheimer's disease and Related Disorders Association (ADRDA) criteria. The NINCDS-ADRDA Alzheimer's Criteria were proposed in 1984 by the National Institute of Neurological and Communicative Disorders and Stroke and the Alzheimer's Disease and Related Disorders Association (now known as the Alzheimer's Association) and are among the most used in the diagnosis of Alzheimer's disease (AD). McKhann, et al. (1984) *Neurology* 34(7): 939-44. According to these criteria, the presence of cognitive impairment and a suspected dementia syndrome should be confirmed by neuropsychological testing for a clinical diagnosis of possible or probable AD. However, histopathologic confirmation (microscopic examination of brain tissue) is generally used for a dispositive diagnosis. The NINCDS-ADRDA Alzheimer's Criteria specify eight cognitive domains that may be impaired in AD: memory, language, perceptual skills, attention, constructive abilities, orientation, problem solving and functional abilities). These criteria have shown good reliability and validity.

Baseline evaluations of patient function can made using classic psychometric measures, such as the Mini-Mental State Exam (MMSE) (Folstein et al. (1975) *J. Psychiatric Research* 12 (3): 189-198), and the Alzheimer's Disease Assessment Scale (ADAS), which is a comprehensive scale for evaluating patients with Alzheimer's Disease status and function (see, e.g., Rosen, et al. (1984) *Am. J. Psychiatr.*, 141: 1356-1364). These psychometric scales provide a measure of progression of the Alzheimer's condition. Suitable qualitative life scales can also be used to monitor treatment. The extent of disease progression can be determined using a Mini-Mental State Exam (MMSE) (see, e.g., Folstein, et al. supra). Any score greater than or equal to 25 points (out of 30) is effectively normal (intact). Below this, scores can indicate severe (≤9 points), moderate (10-20 points) or mild (21-24 points) Alzheimer's disease.

Alzheimer's disease can be broken down into various stages including:

1) Moderate cognitive decline (Mild or early-stage Alzheimer's disease), 2) Moderately severe cognitive decline (Moderate or mid-stage Alzheimer's disease), 3) Severe cognitive decline (Moderately severe or mid-stage Alzheimer's disease), and 4) Very severe cognitive decline (Severe or late-stage Alzheimer's disease) as shown in Table 2.

TABLE 2

Illustrative stages of Alzheimer's disease.

Moderate Cognitive Decline (Mild or early stage AD)

At this stage, a careful medical interview detects clear-cut deficiencies in the following areas:
Decreased knowledge of recent events.
Impaired ability to perform challenging mental arithmetic. For example, to count backward from 100 by 7s.
Decreased capacity to perform complex tasks, such as marketing, planning dinner for guests, or paying bills and managing finances.
Reduced memory of personal history.
The affected individual may seem subdued and withdrawn, especially in socially or mentally challenging situations.
Moderately severe cognitive decline (Moderate or mid-stage Alzheimer's disease)

Major gaps in memory and deficits in cognitive function emerge. Some assistance with day-to-day activities becomes essential. At this stage, individuals may:
Be unable during a medical interview to recall such important details as their current address, their telephone number, or the name of the college or high school from which they graduated.
Become confused about where they are or about the date, day of the week or season.
Have trouble with less challenging mental arithmetic; for example, counting backward from 40 by 4s or from 20 by 2s.
Need help choosing proper clothing for the season or the occasion.
Usually retain substantial knowledge about themselves and know their own name and the names of their spouse or children.
Usually require no assistance with eating or using the toilet.
Severe cognitive decline (Moderately severe or mid-stage Alzheimer's disease)

Memory difficulties continue to worsen, significant personality changes may emerge, and affected individuals need extensive help with daily activities. At this stage, individuals may:
Lose most awareness of recent experiences and events as well as of their surroundings.
Recollect their personal history imperfectly, although they generally recall their own name.
Occasionally forget the name of their spouse or primary caregiver but generally can distinguish familiar from unfamiliar faces.
Need help getting dressed properly; without supervision, may make such errors as putting pajamas over daytime clothes or shoes on wrong feet.
Experience disruption of their normal sleep/waking cycle.
Need help with handling details of toileting (flushing toilet, wiping and disposing of tissue properly).
Have increasing episodes of urinary or fecal incontinence.
Experience significant personality changes and behavioral symptoms, including suspiciousness and delusions (for example, believing that their TABLE 2-continued Illustrative stages of Alzheimer's disease.

caregiver is an impostor); hallucinations (seeing or hearing things that are not really there); or compulsive, repetitive behaviors such as hand-wringing or tissue shredding.
Tend to wander and become lost.
Very severe cognitive decline (Severe or late-stage Alzheimer's disease)

This is the final stage of the disease when individuals lose the ability to respond to their environment, the ability to speak, and, ultimately, the ability to control movement.
Frequently individuals lose their capacity for recognizable speech, although words or phrases may occasionally be uttered.
Individuals need help with eating and toileting and there is general incontinence.
Individuals lose the ability to walk without assistance, then the ability to sit without support, the ability to smile, and the ability to hold their head up.
Reflexes become abnormal and muscles grow rigid. Swallowing is impaired.

In various embodiments administration of one or more agents described herein to subjects diagnosed with Alzheimer's disease is deemed effective when the there is a reduction in the CSF of levels of one or more components selected from the group consisting of Tau, phospho-Tau (pTau), APPneo, soluble Aβ40, soluble Aβ42, and/or and Aβ42/Aβ40 ratio, and/or when there is a reduction of the plaque load in the brain of the subject, and/or when there is a reduction in the rate of plaque formation in the brain of the subject, and/or when there is an improvement in the cognitive abilities of the subject, and/or when there is a perceived improvement in quality of life by the subject, and/or when there is a significant reduction in clinical dementia rating (CDR) of the subject, and/or when the rate of increase in clinical dementia rating is slowed or stopped and/or when the progression of AD is slowed or stopped (e.g., when the transition from one stage to another as listed in Table 3 is slowed or stopped).

In certain embodiments Subjects amenable to the present methods generally are free of a neurological disease or disorder other than Alzheimer's disease. For example, in certain embodiments, the subject does not have and is not at risk of developing a neurological disease or disorder such as Parkinson's disease, and/or schizophrenia, and/or psychosis.

Active Agent(s).

The methods described herein are based, in part, on the discovery that administration of one or more active agents e.g., ASBIs such as galangin, rutin, and analogues, derivatives, or prodrugs thereof find use in the treatment and/or prophylaxis of diseases characterized by amyloid deposits in the brain, for example, mild cognitive impairment, Alzheimer's disease, macular degeneration, and the like.

Bioflavanoids.

In certain embodiments the active agent(s) used in the methods described herein comprise a flavanoid such as galangin or rutin or a derivative and/or analogue thereof. In certain embodiments the flavonoid is characterized by Formula I:

I where $R^1$ is selected from the group consisting of OH, O-saccaharide, O-alkyl, O-trifluoromethyl, O-aryl, O-heteroaryl; $R^4$ and $R^5$ are independently selected from the group consisting of H, OH, $NH_2$, O-alkyl, O-trifluoromethyl, S-alkyl, S-aryl, carboxylate, halogen, NH-alkyl, N,N-dialkyl, NHCO-alkyl, and heteroaryl, alkyl urea, and carbamate; and $R^2$ and $R^3$ are independently selected from the group consisting of H, OH, $NH_2$, O-alkyl, O-trifluoromethyl, S-alkyl, S-aryl, carboxylate, halogen, NH-alkyl, N,N-dialkyl, NHCO-alkyl, heteroaryl, alkyl urea, and carbamate.

In certain embodiments $R^2$ and/or $R^3$ is OH. In certain embodiments $R^2$ is OH and $R^3$ is OH. In certain embodiments $R^2$ and/or $R^3$ are independently selected from the group consisting of O-alkyl, S-alkyl, NH-alkyl and NHCO-alkyl. In certain embodiments the alkyl component of the O-alkyl, S-alkyl, NH-alkyl and NHCO-alkyl is a $C_{1-12}$ alkyl, or a $C_{1-9}$ alkyl, or a $C_{1-6}$ alkyl, or a $C_{1-3}$ alkyl. In certain embodiments $R^2$ and/or $R^3$ is halogen. In certain embodiments $R^2$ is halogen and $R^3$ is halogen. In certain embodiments $R^2$ and/or $R^3$ are independently selected from the group consisting of Cl, Br, Fl, and I. In certain embodiments $R^2$ and/or $R^3$ is selected from the group consisting of S-aryl and heteroaryl. In certain embodiments $R^2$ and $R^3$ are independently selected S-aryl. In certain embodiments $R^2$ and $R^3$ are independently selected heteroaryl. In certain embodiments $R^4$ and/or $R^5$ is OH. In certain embodiments $R^4$ is H and $R^5$ is OH or $R^4$ is OH and $R^5$ is H. In certain embodiments $R^4$ is OH and $R^5$ is OH. In certain embodiments $R^4$ and/or $R^5$ is H. In certain embodiments $R^4$ is H and $R^5$ is H. In certain embodiments when $R^4$ and/or $R^5$ is OH, $R^1$ is O-Saccharide. In certain embodiments $R^4$ and/or $R^5$ are independently selected from the group consisting of O-alkyl, S-alkyl, NH-alkyl and NHCO-alkyl. In certain embodiments $R^4$ and $R^5$ are independently selected from the group consisting of O-alkyl, S-alkyl, NH-alkyl and NHCO-alkyl. In certain embodiments the alkyl component of said O-alkyl, S-alkyl, NH-alkyl and NHCO-alkyl is a $C_{1-12}$ alkyl, or a $C_{1-9}$ alkyl, or a $C_{1-6}$ alkyl, or a $C_{1-3}$ alkyl. In certain embodiments $R^4$ and/or $R^5$ is halogen. In certain embodiments $R^4$ is halogen and $R^5$ is halogen. In certain embodiments $R^4$ and/or $R^5$ are independently selected from the group consisting of Cl, Br, Fl, and I. In certain embodiments $R^4$ and/or $R^5$ is selected from the group consisting of S-aryl and heter In certain embodiments $R^4$ and $R^5$ are independently selected heteroaryl. In certain embodiments $R^1$ is O-Saccharide (e.g., O-monosaccharide, O-disaccharide, O-trisaccharide, etc.). In certain embodiments $R^1$ is O-alkyl, O-trifluoromethyl, O-aryl, or O-heteroaryl.

In certain embodiments the APP specific BACE inhibitor is galangin or a derivative thereof. In certain embodiments APP specific BACE inhibitor is rutin or a derivative thereof.

Methods of making galangin and/or rutin and/or the various derivatives thereof contemplated herein are known to those of skill in the art. Both galangin and rutin are commercially available as are certain derivatives.

These compounds can be further functionalized to prepare the various derivatives and analogues described herein using methods well known to those of skill in the art. For example the procedure described in example 2 would be used in the synthesis of analogs using various commercially available Dihydroxy-2-phenyl-4H-chromen-4-ones. The cobversion to the acetoxy groups would be done as described in example 2. Treatment with dimethyldioxirane would used to convert to the 3-hydroxyflavone. Further hydrolysis with mild base can be done to remove the acetoxy protecting groups, the crude mixture of the flavone derivatives can be purified by flash chromatography and recrystallisation to obtain the desired flavone analogs.

Flavanoid Prodrugs.

Figure 2:
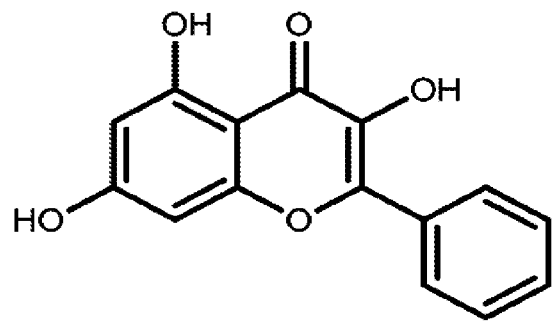
FIG. 2 illustrates galangin and various pro-galantine.
Figure 2:
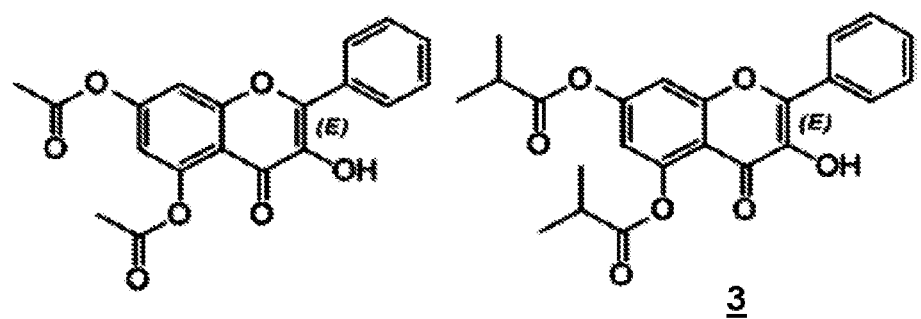
Figure 2:
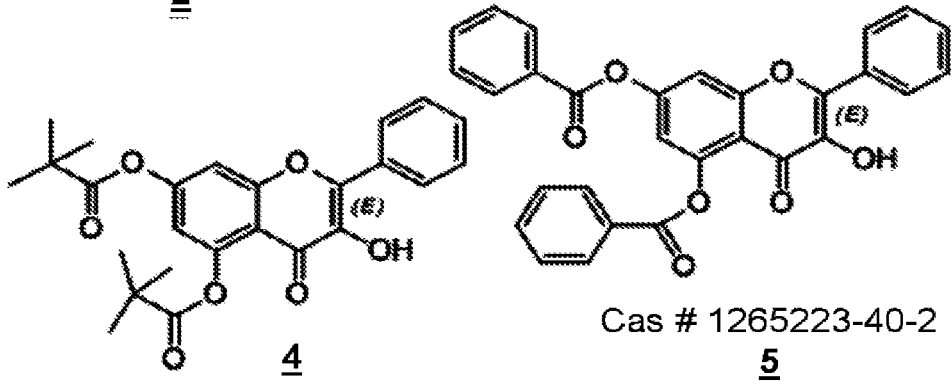

In certain embodiments it is contemplated that the various flavonoids described herein can be provided as flavonoid prodrugs. Illustrative galangin prodrugs are shown in FIG. 2.

In certain embodiments the prodrug is a galangin prodrug is characterized by Formula II:

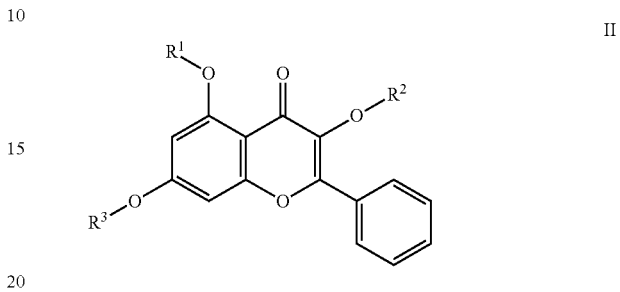

II where $R^1$, $R^2$, and $R^3$ are H, or a protecting group that is removed in vivo in a mammal, wherein at least one of $R^1$, $R^2$, and $R^3$ is not H; and wherein said prodrug partially or completely inhibits BACE processing of APP when administered to a mammal.

In certain embodiments at least one of $R^1$, $R^2$, and $R^3$ are independently selected from the group consisting of least one of $R^1$, $R^2$, and $R^3$ are independently selected from the group consisting of

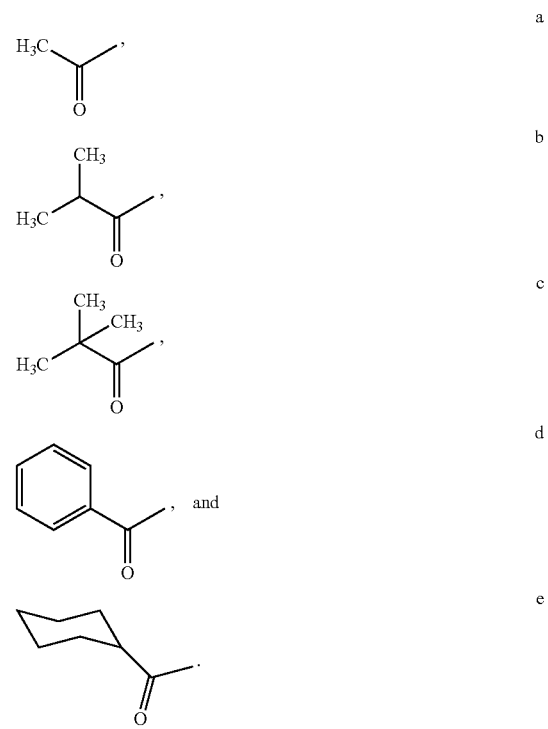

In certain embodiments $R^1$ is H. In certain embodiments $R^2$ is Group a, above and $R^3$ is Group a, b, c, d, or e, above. In certain embodiments $R^3$ is Group a, above and $R^2$ is Group a, b, c, d, or e, above. In certain embodiments, $R^2$ and $R^3$ are both group a above.

In certain embodiments $R^1$ is H. In certain embodiments $R^2$ is Group b, above and $R^3$ is Group a, b, c, d, or e, above.

In certain embodiments $R^3$ is Group b, above and $R^2$ is Group a, b, c, d, or e, above. In certain embodiments, $R^2$ and $R^3$ are both group b above.

In certain embodiments $R^1$ is H. In certain embodiments $R^2$ is Group c, above and $R^3$ is Group a, b, c, d, or e, above. In certain embodiments $R^3$ is Group c, above and $R^2$ is Group a, b, c, d, or e, above. In certain embodiments, $R^2$ and $R^3$ are both group c above.

In certain embodiments $R^1$ is H. In certain embodiments $R^2$ is Group d, above and $R^3$ is Group a, b, c, d, or e, above. In certain embodiments $R^3$ is Group d, above and $R^2$ is Group a, b, c, d, or e, above. In certain embodiments, $R^2$ and $R^3$ are both group d above.

In certain embodiments $R^1$ is H. In certain embodiments $R^2$ is Group e, above and $R^3$ is Group a, b, c, d, or e, above. In certain embodiments $R^3$ is Group e, above and $R^2$ is Group a, b, c, d, or e, above. In certain embodiments, $R^2$ and $R^3$ are both group e above.

Methods of preparing galangin prodrugs such as are described herein are known to those of skill in the art.

Figure 11:
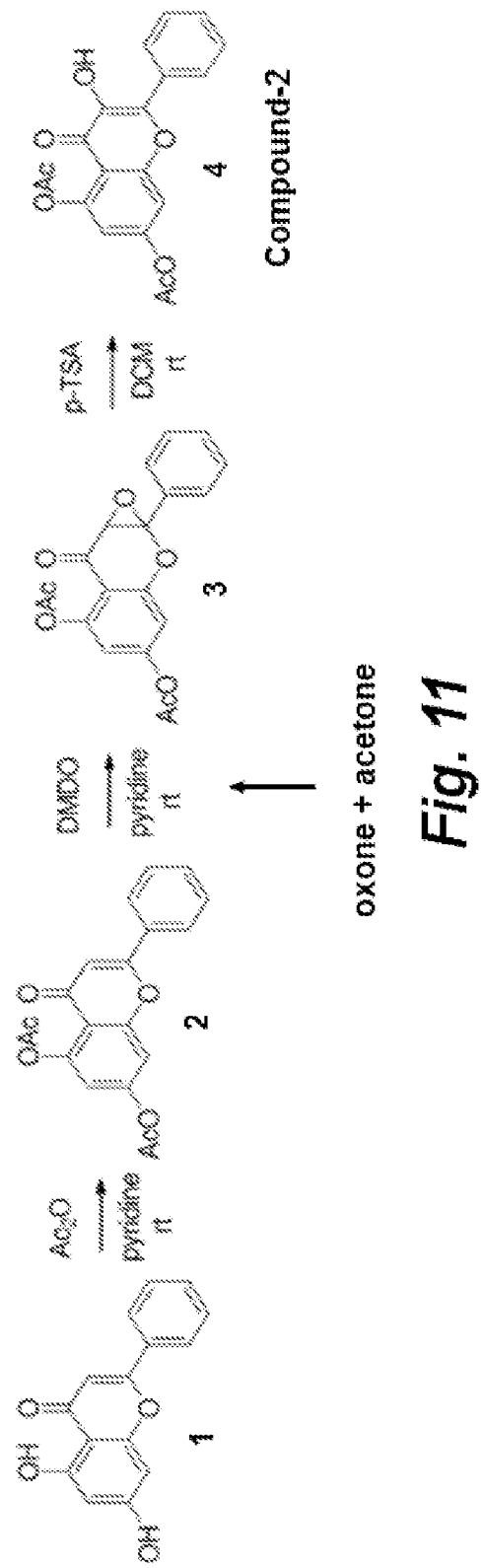
FIG. 11 illustrates a synthesis scheme for progalangin (compound 2).

One such protocol is illustrated in Example 2 (see synthesis scheme in FIG. 11 for the synthesis of compound 2.

The various active agents and synthesis schemes are intended to be illustrative and not limiting. Using the teachings provided herein, numerous other flavonoid, flavonoid derivative, and flavonoid prodrug ASBI compounds can be synthesized and identified by one of skill in the art.

Pharmaceutical Formulations.

In certain embodiments one or more active agents described herein (e.g., ASBIs such as galangin, rutin, and analogues, derivatives, or prodrugs thereof, or tautomer(s) or stereoisomer(s) thereof, or pharmaceutically acceptable salts or solvates of said ASBI(s), said stereoisomer(s), or said tautomer(s), or analogues, derivatives, or prodrugs thereof) are administered to a mammal in need thereof, e.g., to a mammal at risk for or suffering from a pathology characterized by abnormal processing of amyloid precursor proteins, a mammal at risk for progression of MCI to Alzheimer's disease, and so forth. In certain embodiments the active agent(s) are administered to prevent or delay the onset of a pre-Alzheimer's condition and/or cognitive dysfunction, and/or to ameliorate one or more symptoms of a pre-Alzheimer's cognitive dysfunction, and/or to prevent or delay the progression of a pre-Alzheimer's condition or cognitive dysfunction to Alzheimer's disease, and/or to promote the processing of amyloid precursor protein (APP) by a non-amyloidogenic pathway.

The active agent(s) can be administered in the "native" form or, if desired, in the form of salts, esters, amides, prodrugs, derivatives, and the like, provided the salt, ester, amide, prodrug or derivative is suitable pharmacologically, i.e., effective in the present method(s). Salts, esters, amides, prodrugs and other derivatives of the active agents can be prepared using standard procedures known to those skilled in the art of synthetic organic chemistry and described, for example, by March (1992) *Advanced Organic Chemistry; Reactions, Mechanisms and Structure,* 4th Ed. N.Y. Wiley-Interscience, and as described above.

For example, a pharmaceutically acceptable salt can be prepared for any of the agent(s) described herein having a functionality capable of forming a salt. A pharmaceutically acceptable salt is any salt that retains the activity of the parent compound and does not impart any deleterious or untoward effect on the subject to which it is administered and in the context in which it is administered.

In various embodiments pharmaceutically acceptable salts may be derived from organic or inorganic bases. The salt may be a mono or polyvalent ion. Of particular interest are the inorganic ions, lithium, sodium, potassium, calcium, and magnesium. Organic salts may be made with amines, particularly ammonium salts such as mono-, di- and trialkyl amines or ethanol amines. Salts may also be formed with caffeine, tromethamine and similar molecules.

Methods of formulating pharmaceutically active agents as salts, esters, amide, prodrugs, and the like are well known to those of skill in the art. For example, salts can be prepared from the free base using conventional methodology that typically involves reaction with a suitable acid. Generally, the base form of the drug is dissolved in a polar organic solvent such as methanol or ethanol and the acid is added thereto. The resulting salt either precipitates or can be brought out of solution by addition of a less polar solvent. Suitable acids for preparing acid addition salts include, but are not limited to both organic acids, e.g., acetic acid, propionic acid, glycolic acid, pyruvic acid, oxalic acid, malic acid, malonic acid, succinic acid, maleic acid, fumaric acid, tartaric acid, citric acid, benzoic acid, cinnamic acid, mandelic acid, methanesulfonic acid, ethanesulfonic acid, p-toluenesulfonic acid, salicylic acid, and the like, as well as inorganic acids, e.g., hydrochloric acid, hydrobromic acid, sulfuric acid, nitric acid, phosphoric acid, and the like. An acid addition salt can be reconverted to the free base by treatment with a suitable base. Certain particularly preferred acid addition salts of the active agents herein include halide salts, such as may be prepared using hydrochloric or hydrobromic acids. Conversely, preparation of basic salts of the active agents of this invention are prepared in a similar manner using a pharmaceutically acceptable base such as sodium hydroxide, potassium hydroxide, ammonium hydroxide, calcium hydroxide, trimethylamine, or the like. Particularly preferred basic salts include alkali metal salts, e.g., the sodium salt, and copper salts.

For the preparation of salt forms of basic drugs, the pKa of the counterion is preferably at least about 2 pH units lower than the pKa of the drug. Similarly, for the preparation of salt forms of acidic drugs, the pKa of the counterion is preferably at least about 2 pH units higher than the pKa of the drug. This permits the counterion to bring the solution's pH to a level lower than the $pH_{max}$ to reach the salt plateau, at which the solubility of salt prevails over the solubility of free acid or base. The generalized rule of difference in pKa units of the ionizable group in the active pharmaceutical ingredient (API) and in the acid or base is meant to make the proton transfer energetically favorable. When the pKa of the API and counterion are not significantly different, a solid complex may form but may rapidly disproportionate (i.e., break down into the individual entities of drug and counterion) in an aqueous environment.

Preferably, the counterion is a pharmaceutically acceptable counterion. Suitable anionic salt forms include, but are not limited to acetate, benzoate, benzylate, bitartrate, bromide, carbonate, chloride, citrate, edetate, edisylate, estolate, fumarate, gluceptate, gluconate, hydrobromide, hydrochloride, iodide, lactate, lactobionate, malate, maleate, mandelate, mesylate, methyl bromide, methyl sulfate, mucate, napsylate, nitrate, pamoate (embonate), phosphate and diphosphate, salicylate and disalicylate, stearate, succinate, sulfate, tartrate, tosylate, triethiodide, valerate, and the like, while suitable cationic salt forms include, but are not limited to aluminum, benzathine, calcium, ethylene diamine, lysinc, magnesium, meglumine, potassium, procaine, sodium, tromethamine, zinc, and the like.

Preparation of esters typically involves functionalization of hydroxyl and/or carboxyl groups that are present within the molecular structure of the active agent. In certain embodiments, the esters are typically acyl-substituted derivatives of free alcohol groups, i.e., moieties that are derived from carboxylic acids of the formula RCOOH where R is alky, and preferably is lower alkyl. Esters can be reconverted to the free acids, if desired, by using conventional hydrogenolysis or hydrolysis procedures.

Amides can also be prepared using techniques known to those skilled in the art or described in the pertinent literature. For example, amides may be prepared from esters, using suitable amine reactants, or they may be prepared from an anhydride or an acid chloride by reaction with ammonia or a lower alkyl amine.

In various embodiments, the active agents identified herein (e.g., ASBIs such as galangin, rutin, and analogues, derivatives, or prodrugs thereof, or tautomer(s) or stereoisomer(s) thereof, or pharmaceutically acceptable salts or solvates of said ASBI(s), said stereoisomer(s), or said tautomer(s), or analogues, derivatives, or prodrugs thereof) are useful for parenteral administration, topical administration, oral administration, nasal administration (or otherwise inhaled), rectal administration, or local administration, such as by aerosol or transdermally, for prophylactic and/or therapeutic treatment of one or more of the pathologies/indications described herein (e.g., pathologies characterized by excess amyloid plaque formation and/or deposition or undesired amyloid or pre-amyloid processing).

The active agents described herein can also be combined with a pharmaceutically acceptable carrier (excipient) to form a pharmacological composition. Pharmaceutically acceptable carriers can contain one or more physiologically acceptable compound(s) that act, for example, to stabilize the composition or to increase or decrease the absorption of the active agent(s). Physiologically acceptable compounds can include, for example, carbohydrates, such as glucose, sucrose, or dextrans, antioxidants, such as ascorbic acid or glutathione, chelating agents, low molecular weight proteins, protection and uptake enhancers such as lipids, compositions that reduce the clearance or hydrolysis of the active agents, or excipients or other stabilizers and/or buffers.

Other physiologically acceptable compounds, particularly of use in the preparation of tablets, capsules, gel caps, and the like include, but are not limited to binders, diluent/fillers, disentegrants, lubricants, suspending agents, and the like.

In certain embodiments, to manufacture an oral dosage form (e.g., a tablet), an excipient (e.g., lactose, sucrose, starch, mannitol, etc.), an optional disintegrator (e.g. calcium carbonate, carboxymethylcellulose calcium, sodium starch glycollate, crospovidone etc.), a binder (e.g. alpha-starch, gum arabic, microcrystalline cellulose, carboxymethyl cellulose, polyvinylpyrrolidone, hydroxypropyl cellulose, cyclodextrin, etc.), and an optional lubricant (e.g., talc, magnesium stearate, polyethylene glycol 6000, etc.), for instance, are added to the active component or components (e.g., ASBIs such as galangin, rutin, and analogues, derivatives, or prodrugs thereof, or tautomer(s) or stereoisomer(s) thereof, or pharmaceutically acceptable salts or solvates of said ASBI(s), said stereoisomer(s), or said tautomer(s), or analogues, derivatives, or prodrugs thereof) and the resulting composition is compressed. Where necessary the compressed product is coated, e.g., using known methods for masking the taste or for enteric dissolution or sustained release. Suitable coating materials include, but are not limited to ethyl-cellulose, hydroxymethylcellulose, POLYOX®yethylene glycol, cellulose acetate phthalate, hydroxypropylmethylcellulose phthalate, and Eudragit (Rohm & Haas, Germany; methacrylic-acrylic copolymer).

Other physiologically acceptable compounds include wetting agents, emulsifying agents, dispersing agents or preservatives that are particularly useful for preventing the growth or action of microorganisms. Various preservatives are well known and include, for example, phenol and ascorbic acid. One skilled in the art would appreciate that the choice of pharmaceutically acceptable carrier(s), including a physiologically acceptable compound depends, for example, on the route of administration of the active agent(s) and on the particular physio-chemical characteristics of the active agent(s).

In certain embodiments the excipients are sterile and generally free of undesirable matter. These compositions can be sterilized by conventional, well-known sterilization techniques. For various oral dosage form excipients such as tablets and capsules sterility is not required. The USP/NF standard is usually sufficient.

The pharmaceutical compositions can be administered in a variety of unit dosage forms depending upon the method of administration. Suitable unit dosage forms, include, but are not limited to powders, tablets, pills, capsules, lozenges, suppositories, patches, nasal sprays, injectibles, implantable sustained-release formulations, mucoadherent films, topical varnishes, lipid complexes, etc.

Pharmaceutical compositions comprising the active agents described herein (e.g., ASBIs such as galangin, rutin, and analogues, derivatives, or prodrugs thereof, or tautomer(s) or stereoisomer(s) thereof, or pharmaceutically acceptable salts or solvates of said ASBI(s), said stereoisomer(s), or said tautomer(s), or analogues, derivatives, or prodrugs thereof) can be manufactured by means of conventional mixing, dissolving, granulating, dragee-making, levigating, emulsifying, encapsulating, entrapping or lyophilizing processes. Pharmaceutical compositions can be formulated in a conventional manner using one or more physiologically acceptable carriers, diluents, excipients or auxiliaries that facilitate processing of the active agent(s) into preparations that can be used pharmaceutically. Proper formulation is dependent upon the route of administration chosen.

In certain embodiments, the active agents described herein are formulated for oral administration. For oral administration, suitable formulations can be readily formulated by combining the active agent(s) with pharmaceutically acceptable carriers suitable for oral delivery well known in the art. Such carriers enable the active agent(s) described herein to be formulated as tablets, pills, dragees, caplets, lizenges, gelcaps, capsules, liquids, gels, syrups, slurries, suspensions and the like, for oral ingestion by a patient to be treated. For oral solid formulations such as, for example, powders, capsules and tablets, suitable excipients can include fillers such as sugars (e.g., lactose, sucrose, mannitol and sorbitol), cellulose preparations (e.g., maize starch, wheat starch, rice starch, potato starch, gelatin, gum tragacanth, methyl cellulose, hydroxypropylmethyl-cellulose, sodium carboxymethylcellulose), synthetic polymers (e.g., polyvinylpyrrolidone (PVP)), granulating agents; and binding agents. If desired, disintegrating agents may be added, such as the cross-linked polyvinylpyrrolidone, agar, or alginic acid or a salt thereof such as sodium alginate. If desired, solid dosage forms may be sugar-coated or enteric-coated using standard techniques. The preparation of enteric-coated particles is disclosed for example in U.S. Pat. Nos. 4,786,505 and 4,853,230.

For administration by inhalation, the active agent(s) are conveniently delivered in the form of an aerosol spray from pressurized packs or a nebulizer, with the use of a suitable propellant, e.g., dichlorodifluoromethane, trichlorofluoromethane, dichlorotetrafluoroethane, carbon dioxide or other suitable gas. In the case of a pressurized aerosol the dosage unit can be determined by providing a valve to deliver a metered amount. Capsules and cartridges of e.g. gelatin for use in an inhaler or insufflator may be formulated containing a powder mix of the compound and a suitable powder base such as lactose or starch.

In various embodiments the active agent(s) can be formulated in rectal or vaginal compositions such as suppositories or retention enemas, e.g., containing conventional suppository bases such as cocoa butter or other glycerides. Methods of formulating active agents for rectal or vaginal delivery are well known to those of skill in the art (see, e.g., Allen (2007) Suppositories, Pharmaceutical Press) and typically involve combining the active agents with a suitable base (e.g., hydrophilic (PEG), lipophilic materials sue as cocoa butter or Witepsol W45), amphiphilic materials such as Suppocire AP and polyglycolized glyceride, and the like). The base is selected and compounded for a desired melting/delivery profile.

For topical administration the active agent(s) described herein (e.g., ASBIs such as galangin, rutin, and analogues, derivatives, or prodrugs thereof, or tautomer(s) or stereoisomer(s) thereof, or pharmaceutically acceptable salts or solvates of said ASBI(s), said stereoisomer(s), or said tautomer(s), or analogues, derivatives, or prodrugs thereof) can be formulated as solutions, gels, ointments, creams, suspensions, and the like as are well-known in the art.

In certain embodiments the active agents described herein are formulated for systemic administration (e.g., as an injectable) in accordance with standard methods well known to those of skill in the art. Systemic formulations include, but are not limited to, those designed for administration by injection, e.g. subcutaneous, intravenous, intramuscular, intrathecal or intraperitoneal injection, as well as those designed for transdermal, transmucosal oral or pulmonary administration. For injection, the active agents described herein can be formulated in aqueous solutions, preferably in physiologically compatible buffers such as Hanks solution, Ringer's solution, or physiological saline buffer and/or in certain emulsion formulations. The solution(s) can contain formulatory agents such as suspending, stabilizing and/or dispersing agents. In certain embodiments the active agent(s) can be provided in powder form for constitution with a suitable vehicle, e.g., sterile pyrogen-free water, before use. For transmucosal administration, and/or for blood/brain barrier passage, penetrants appropriate to the barrier to be permeated can be used in the formulation. Such penetrants are generally known in the art. Injectable formulations and inhalable formulations are generally provided as a sterile or substantially sterile formulation.

In addition to the formulations described previously, the active agent(s) may also be formulated as a depot preparations. Such long acting formulations can be administered by implantation (for example subcutaneously or intramuscularly) or by intramuscular injection. Thus, for example, the active agent(s) may be formulated with suitable polymeric or hydrophobic materials (for example as an emulsion in an acceptable oil) or ion exchange resins, or as sparingly soluble derivatives, for example, as a sparingly soluble salt.

In certain embodiments the active agent(s) described herein can also be delivered through the skin using conventional transdermal drug delivery systems, i.e., transdermal "patches" wherein the active agent(s) are typically contained within a laminated structure that serves as a drug delivery device to be affixed to the skin. In such a structure, the drug composition is typically contained in a layer, or "reservoir," underlying an upper backing layer. It will be appreciated that the term "reservoir" in this context refers to a quantity of "active ingredient(s)" that is ultimately available for delivery to the surface of the skin. Thus, for example, the "reservoir" may include the active ingredient(s) in an adhesive on a backing layer of the patch, or in any of a variety of different matrix formulations known to those of skill in the art. The patch may contain a single reservoir, or it may contain multiple reservoirs.

In one illustrative embodiment, the reservoir comprises a polymeric matrix of a pharmaceutically acceptable contact adhesive material that serves to affix the system to the skin during drug delivery. Examples of suitable skin contact adhesive materials include, but are not limited to, polyethylenes, polysiloxanes, polyisobutylenes, polyacrylates, polyurethanes, and the like. Alternatively, the drug-containing reservoir and skin contact adhesive are present as separate and distinct layers, with the adhesive underlying the reservoir which, in this case, may be either a polymeric matrix as described above, or it may be a liquid or hydrogel reservoir, or may take some other form. The backing layer in these laminates, which serves as the upper surface of the device, preferably functions as a primary structural element of the "patch" and provides the device with much of its flexibility. The material selected for the backing layer is preferably substantially impermeable to the active agent(s) and any other materials that are present.

Alternatively, other pharmaceutical delivery systems can be employed. For example, liposomes, emulsions, and microemulsions/nanoemulsions are well known examples of delivery vehicles that may be used to protect and deliver pharmaceutically active compounds. Certain organic solvents such as dimethylsulfoxide also can be employed, although usually at the cost of greater toxicity.

In certain embodiments the active agent(s) described herein (e.g., ASBIs such as galangin, rutin, and analogues, derivatives, or prodrugs thereof, or tautomer(s) or stereoisomer(s) thereof, or pharmaceutically acceptable salts or solvates of said ASBI(s), said stereoisomer(s), or said tautomer(s), or analogues, derivatives, or prodrugs thereof) are formulated in a nanoemulsion. Nanoemulsions include, but are not limited to oil in water (O/W) nanoemulsions, and water in oil (W/O) nanoemulsions. Nanoemulsions can be defined as emulsions with mean droplet diameters ranging from about 20 to about 1000 nm. Usually, the average droplet size is between about 20 nm or 50 nm and about 500 nm. The terms sub-micron emulsion (SME) and miniemulsion are used as synonyms.

Illustrative oil in water (O/W) nanocmulsions include, but are not limited to: Surfactant micelles—micelles composed of small molecules surfactants or detergents (e.g., SDS/PBS/2-propanol); Polymer micelles—micelles composed of polymer, copolymer, or block copolymer surfactants (e.g., Pluronic L64/PBS/2-propanol); Blended micelles—micelles in which there is more than one surfactant component or in which one of the liquid phases (generally an alcohol or fatty acid compound) participates in the formation of the micelle (e.g., octanoic acid/PBS/EtOH); Integral micelles—blended micelles in which the active agent(s) serve as an auxiliary surfactant, forming an integral part of the micelle; and Pickering (solid phase) emulsions—emulsions in which the active agent(s) are associated with the exterior of a solid nanoparticle (e.g., polystyrene nanoparticles/PBS/no oil phase).

Illustrative water in oil (W/O) nanoemulsions include, but are not limited to: Surfactant micelles—micelles composed of small molecules surfactants or detergents (e.g., dioctyl sulfosuccinate/PBS/2-propanol, isopropylmyristate/PBS/2-propanol, etc.); Polymer micelles—micelles composed of polymer, copolymer, or block copolymer surfactants (e.g., PLURONIC® L121/PBS/2-propanol); Blended micelles—micelles in which there is more than one surfactant component or in which one of the liquid phases (generally an alcohol or fatty acid compound) participates in the formation of the micelle (e.g., capric/caprylic diglyceride/PBS/EtOH); Integral micelles—blended micelles in which the active agent(s) serve as an auxiliary surfactant, forming an integral part of the micelle (e.g., active agent/PBS/polypropylene glycol); and Pickering (solid phase) emulsions—emulsions in which the active agent(s) are associated with the exterior of a solid nanoparticle (e.g., chitosan nanoparticles/no aqueous phase/mineral oil).

As indicated above, in certain embodiments the nanoemulsions comprise one or more surfactants or detergents. In some embodiments the surfactant is a non-anionic detergent (e.g., a polysorbate surfactant, a polyoxyethylene ether, etc.). Surfactants that find use in the present invention include, but are not limited to surfactants such as the TWEEN®, TRITON®, and TYLOXAPOL® families of compounds.

In certain embodiments the emulsions further comprise one or more cationic halogen containing compounds, including but not limited to, cetylpyridinium chloride. In still further embodiments, the compositions further comprise one or more compounds that increase the interaction ("interaction enhancers") of the composition with microorganisms (e.g., chelating agents like ethylenediaminetetraacetic acid, or ethylenebis(oxyethylenenitrilo)tetraacetic acid in a buffer).

In some embodiments, the nanoemulsion further comprises an emulsifying agent to aid in the formation of the emulsion. Emulsifying agents include compounds that aggregate at the oil/water interface to form a kind of continuous membrane that prevents direct contact between two adjacent droplets. Certain embodiments of the present invention feature oil-in-water emulsion compositions that may readily be diluted with water to a desired concentration without impairing their anti-pathogenic properties.

In addition to discrete oil droplets dispersed in an aqueous phase, certain oil-in-water emulsions can also contain other lipid structures, such as small lipid vesicles (e.g., lipid spheres that often consist of several substantially concentric lipid bilayers separated from each other by layers of aqueous phase), micelles (e.g., amphiphilic molecules in small clusters of 50-200 molecules arranged so that the polar head groups face outward toward the aqueous phase and the apolar tails are sequestered inward away from the aqueous phase), or lamellar phases (lipid dispersions in which each particle consists of parallel amphiphilic bilayers separated by thin films of water).

These lipid structures are formed as a result of hydrophobic forces that drive apolar residues (e.g., long hydrocarbon chains) away from water. The above lipid preparations can generally be described as surfactant lipid preparations (SLPs). SLPs are minimally toxic to mucous membranes and are believed to be metabolized within the small intestine (see e.g., Hamouda et al., (1998) *J. Infect. Disease* 180: 1939).

In certain embodiments the emulsion comprises a discontinuous oil phase distributed in an aqueous phase, a first component comprising an alcohol and/or glycerol, and a second component comprising a surfactant or a halogen-containing compound. The aqueous phase can comprise any type of aqueous phase including, but not limited to, water (e.g., dionized water, distilled water, tap water) and solutions (e.g., phosphate buffered saline solution or other buffer systems). The oil phase can comprise any type of oil including, but not limited to, plant oils (e.g., soybean oil, avocado oil, flaxseed oil, coconut oil, cottonseed oil, squalene oil, olive oil, canola oil, corn oil, rapeseed oil, safflower oil, and sunflower oil), animal oils (e.g., fish oil), flavor oil, water insoluble vitamins, mineral oil, and motor oil. In certain embodiments, the oil phase comprises 30-90 vol % of the oil-in-water emulsion (i.e., constitutes 30-90% of the total volume of the final emulsion), more preferably 50-80%. The formulations need no be limited to particular surfactants, however in certain embodiments, the surfactant is a polysorbate surfactant (e.g., TWEEN 20®, TWEEN 40®, TWEEN 60®, and TWEEN 80®), a pheoxypolyethoxyethanol (e.g., TRITON® X-100, X-301, X-165, X-102, and X-200, and TYLOXAPOL®), or sodium dodecyl sulfate, and the like.

In certain embodiments a halogen-containing component is present. the nature of the halogen-containing compound, in some preferred embodiments the halogen-containing compound comprises a chloride salt (e.g., NaCl, KCl, etc.), a cetylpyridinium halide, a cetyltrimethylammonium halide, a cetyldimethylethylammonium halide, a cetyldimethylbenzylammonium halide, a cetyltributylphosphonium halide, dodecyltrimethylammonium halides, tetradecyltrimethylammonium halides, cetylpyridinium chloride, cetyltrimethylammonium chloride, cetylbenzyldimethylammonium chloride, cetylpyridinium bromide, cetyltrimethylammonium bromide, cetyldimethylethylammonium bromide, cetyltributylphosphonium bromide, dodecyltrimethylammonium bromide, tetradecyltrimethylammonium bromide, and the like In certain embodiments the emulsion comprises a quaternary ammonium compound. Quaternary ammonium compounds include, but are not limited to, N-alkyldimethyl benzyl ammonium saccharinate, 1,3,5-Triazine-1,3,5(2H,4H,6H)-triethanol; 1-Decanaminium, N-decyl-N,N-dimethyl-, chloride (or) Didecyl dimethyl ammonium chloride; 2-(2-(p-(Diisobuyl)cresosxy)ethoxy)ethyl dimethyl benzyl ammonium chloride; 2-(2-(p-(Diisobutyl)phenoxy)ethoxy) ethyl dimethyl benzyl ammonium chloride; alkyl 1 or 3 benzyl-1-(2-hydroxethyl)-2-imidazolinium chloride; alkyl bis(2-hydroxyethyl)benzyl ammonium chloride; alkyl demethyl benzyl ammonium chloride; alkyl dimethyl 3,4-dichlorobenzyl ammonium chloride (100% C12); alkyl dimethyl 3,4-dichlorobenzyl ammonium chloride (50% C14, 40% C12, 10% C16); alkyl dimethyl 3,4-dichlorobenzyl ammonium chloride (55% C14, 23% C12, 20% C16); alkyl dimethyl benzyl ammonium chloride; alkyl dimethyl benzyl ammonium chloride (100% C14); alkyl dimethyl benzyl ammonium chloride (100% C16); alkyl dimethyl benzyl ammonium chloride (41% C14, 28% C12); alkyl dimethyl benzyl ammonium chloride (47% C12, 18% C14); alkyl dimethyl benzyl ammonium chloride (55% C16, 20% C14); alkyl dimethyl benzyl ammonium chloride (58% C14, 28% C16); alkyl dimethyl benzyl ammonium chloride (60% C14, 25% C12); alkyl dimethyl benzyl ammonium chloride (61% C11, 23% C14); alkyl dimethyl benzyl ammonium chloride (61% C12, 23% C14); alkyl dimethyl benzyl ammonium chloride (65% C12, 25% C14); alkyl dimethyl benzyl ammonium chloride (67% C12, 24% C14); alkyl dimethyl benzyl ammonium chloride (67% C12, 25% C14); alkyl dimethyl benzyl ammonium chloride (90% C14, 5% C12); alkyl dimethyl benzyl ammonium chloride (93% C14, 4% C12); alkyl dimethyl benzyl ammonium chloride (95% C16, 5% C18); alkyl dimethyl benzyl ammonium chloride (and) didecyl dimethyl ammonium chloride; alkyl dimethyl benzyl ammonium chloride (as in fatty acids); alkyl dimethyl benzyl ammonium chloride (C12-C16); alkyl dimethyl benzyl ammonium chloride (C12-C18); alkyl dimethyl benzyl and dialkyl dimethyl ammonium chloride; alkyl dimethyl dimethybenzyl ammonium chloride; alkyl dimethyl ethyl ammonium bromide (90% C14, 5% C16, 5% C12); alkyl dimethyl ethyl ammonium bromide (mixed alkyl and alkenyl groups as in the fatty acids of soybean oil); alkyl dimethyl ethylbenzyl ammonium chloride; alkyl dimethyl ethylbenzyl ammonium chloride (60% C14); alkyl dimethyl isoproylbenzyl ammonium chloride (50% C12, 30% C14, 17% C16, 3% C18); alkyl trimethyl ammonium chloride (58% C18, 40% C16, 1% C14, 1% C12); alkyl trimethyl ammonium chloride (90% C18, 10% C16); alkyldimethyl (ethylbenzyl) ammonium chloride (C12-18); Di-(C8-10)-alkyl dimethyl ammonium chlorides; dialkyl dimethyl ammonium chloride; dialkyl dimethyl ammonium chloride; dialkyl dimethyl ammonium chloride; dialkyl methyl benzyl ammonium chloride; didecyl dimethyl ammonium chloride; diisodecyl dimethyl ammonium chloride; dioctyl dimethyl ammonium chloride; dodecyl bis(2-hydroxyethyl) octyl hydrogen ammonium chloride; dodecyl dimethyl benzyl ammonium chloride; dodecylcarbamoyl methyl dimethyl benzyl ammonium chloride; heptadecyl hydroxyethylimidazolinium chloride; hexahydro-1,3,5-thris(2-hydroxyethyl)-s-triazine; myristalkonium chloride (and) Quat RNIUM 14; N,N-Dimethyl-2-hydroxypropylammonium chloride polymer; n-alkyl dimethyl benzyl ammonium chloride; n-alkyl dimethyl ethylbenzyl ammonium chloride; n-tetradecyl dimethyl benzyl ammonium chloride monohydrate; octyl decyl dimethyl ammonium chloride; octyl dodecyl dimethyl ammonium chloride; octyphenoxyethoxyethyl dimethyl benzyl ammonium chloride; oxydiethylenebis (alkyl dimethyl ammonium chloride); quaternary ammonium compounds, dicoco alkyldimethyl, chloride; trimethoxysily propyl dimethyl octadecyl ammonium chloride; trimethoxysilyl quats, trimethyl dodecylbenzyl ammonium chloride; n-dodecyl dimethyl ethylbenzyl ammonium chloride; n-hexadecyl dimethyl benzyl ammonium chloride; n-tetradecyl dimethyl benzyl ammonium chloride; n-tetradecyl dimethyl ethylbenzyl ammonium chloride; and n-octadecyl dimethyl benzyl ammonium chloride.

Nanoemulsion formulations and methods of making such are well known to those of skill in the art and described for example in U.S. Pat. Nos. 7,476,393, 7,468,402, 7,314,624, 6,998,426, 6,902,737, 6,689,371, 6,541,018, 6,464,990, 6,461,625, 6,419,946, 6,413,527, 6,375,960, 6,335,022, 6,274,150, 6,120,778, 6,039,936, 5,925,341, 5,753,241, 5,698,219, an d5,152,923 and in Fanun et al. (2009) Microemulsions: Properties and Applications (Surfactant Science), CRC Press, Boca Ratan Fla.

In certain embodiments, one or more active agents described herein can be provided as a "concentrate", e.g., in a storage container (e.g., in a premeasured volume) ready for dilution, or in a soluble capsule ready for addition to a volume of water, alcohol, hydrogen peroxide, or other diluent.

Extended Release (Sustained Release) Formulations.

In certain embodiments "extended release" formulations of the active agent(s) described herein are contemplated. In various embodiments such extended release formulations are designed to avoid the high peak plasma levels of intravenous and conventional immediate release oral dosage forms.

Illustrative sustained-release formulations include, for example, semipermeable matrices of solid polymers containing the therapeutic agent. Various uses of sustained-release materials have been established and are well known by those skilled in the art. Sustained-release capsules may, depending on their chemical nature, release the compounds for a few weeks up to over 100 days. Depending on the chemical nature and the biological stability of the therapeutic reagent, additional strategies for stabilization can be employed.

In certain embodiments such "extended release" formulations utilize the mucosa and can independently control tablet disintegration (or erosion) and/or drug dissolution and release from the tablet over time to provide a safer delivery profile. In certain embodiments the oral formulations of active agent(s) described herein (e.g., ASBIs such as galangin, rutin, and analogues, derivatives, or prodrugs thereof, or tautomer(s) or stereoisomer(s) thereof, or pharmaceutically acceptable salts or solvates of said ASBI(s), said stereoisomer(s), or said tautomer(s), or analogues, derivatives, or prodrugs thereof) provide individual, repetitive doses that include a defined amount of the active agent that is delivered over a defined amount of time.

One illustrative sustained release formulation is a substantially homogeneous composition that comprises about 0.01% to about 99% w/w, or about 0.1% to about 95%, or about 0.1%, or about 1%, or about 2%, or about 5%, or about 10%, or about 15%, or about 20% to about 80%, or to about 90%, or to about 95%, or to about 97%, or to about 98%, or to about 99%1 of the active ingredient(s) (e.g., ASBIs such as galangin, rutin, and analogues, derivatives, or prodrugs thereof, or tautomer(s) or stereoisomer(s) thereof, or pharmaceutically acceptable salts or solvates of said ASBI(s), said stereoisomer(s), or said tautomer(s), or analogues, derivatives, or prodrugs thereof) and one or more mucoadhesives (also referred to herein as "bioadhesives") that provide for adherence to the targeted mucosa of the subject (patient) and that may further comprise one or more of the following: one or more binders that provide binding of the excipients in a single tablet; one or more hydrogel forming excipients; one or more bulking agents; one or more lubricants; one or more glidants; one or more solubilizers; one or more surfactants; one or more flavors; one or more disintegrants; one or more buffering excipients; one or more coatings; one or more controlled release modifiers; and one or more other excipients and factors that modify and control the drug's dissolution or disintegration time and kinetics or protect the active drug from degradation.

In various embodiments a sustained release pharmaceutical dosage form for oral transmucosal delivery can be solid or non-solid. In one preferred embodiment, the dosage from is a solid that turns into a hydrogel following contact with saliva.

Suitable excipients include, but are not limited to substances added to the formulations that are required to produce a commercial product and can include, but are not limited to: bulking agents, binders, surfactants, bioadhesives, lubricants, disintegrants, stabilizers, solubilizers, glidants, and additives or factors that affect dissolution or disintegration time. Suitable excipients are not limited to those above, and other suitable nontoxic pharmaceutically acceptable carriers for use in oral formulations can be found in Remington's Pharmaceutical Sciences, 17th Edition, 1985.

In certain embodiments extended release formulations of the active agent(s) described herein for oral transmucosal drug delivery include at least one bioadhesive (mucoadhesive) agent or a mixture of several bioadhesives to promote adhesion to the oral mucosa during drug delivery. In addition the bioadhesive agents may also be effective in controlling the dosage form erosion time and/or, the drug dissolution kinetics over time when the dosage form is wetted. Such mucoadhesive drug delivery systems are very beneficial, since they can prolong the residence time of the drug at the site of absorption and increase drug bioavailability. The mucoadhesive polymers forming hydrogels are typically hydrophilic and swellable, containing numerous hydrogen bond-forming groups, like hydroxyl, carboxyl or amine, which favor adhesion. When used in a dry form, they attract water from the mucosal surface and swell, leading to polymer/mucus interaction through hydrogen bonding, electrostatic, hydrophobic or van der Waals interaction.

Illustrative suitable mucoadhesive or bioadhesive materials, include, but are not limited to natural, synthetic or biological polymers, lipids, phospholipids, and the like. Examples of natural and/or synthetic polymers include cellulosic derivatives (such as methylcellulose, carboxymethyl cellulose, hydroxyethyl cellulose, hydroxyethylmethyl cellulose, etc), natural gums (such as guar gum, xanthan gum, locust bean gum, karaya gum, veegum etc.), polyacrylates (such as CARBOPOL®, polycarbophil, etc), alginates, thiol-containing polymers, POLYOX®yethylenes, polyethylene glycols (PEG) of all molecular weights (preferably between 1000 and 40,000 Da, of any chemistry, linear or branched), dextrans of all molecular weights (preferably between 1000 and 40,000 Da of any source), block copolymers, such as those prepared by combinations of lactic and glycolic acid (PLA, PGA, PLGA of various viscosities, molecular weights and lactic-to-glycolic acid ratios) polyethylene glycol-polypropylene glycol block copolymers of any number and combination of repeating units (such as PLURONICS®, TEKTRONIX® or GENAPOL® block copolymers), combination of the above copolymers either physically or chemically linked units (for example PEG-PLA or PEG-PLGA copolymers) mixtures. Preferably the bioadhesive excipient is selected from the group of polyethylene glycols, POLYOX®yethylenes, polyacrylic acid polymers, such as CARBOPOL® (such as CARBOPOL® 71G, 934P, 971P, 974P, and the like) and polycarbophils (such as NOVEON® AA-1, NOVEON® CA-1, NOVEON® CA-2, and the like), cellulose and its derivatives and most preferably it is polyethylene glycol, carbopol, and/or a cellulosic derivative or a combination thereof.

In certain embodiments the mucoadhesive/bioadhesive excipient is typically present at 1-50% w/w, preferably 1-40% w/w or most preferably between 5-30% w/w. A particular formulation may contain one or more different bioadhesives in any combination.

In certain embodiments the formulations for oral transmucosal drug delivery also include a binder or mixture of two or more binders which facilitate binding of the excipients into a single dosage form. Exemplary binders are selected from the group consisting of cellulosic derivatives (such as methylcellulose, carboxymethyl cellulose, hydroxyethyl cellulose, hydroxyethylmethyl cellulose, etc.), polyacrylates (such as CARBOPOL®, polycarbophil, etc.), POVIDONE® (all grades), POLYOX®® of any molecular weight or grade, irradiated or not, starch, polyvinylpyrrolidone (PVP), AVICEL®, and the like. In certain embodiments the binder is typically present at 0.5-60% w/w, preferably 1-30% w/w and most preferably 1.5-15% w/w.

In certain embodiments the formulations also include at least one hydrogel-forming excipient. Exemplary hydrogel forming excipients are selected from the group consisting of polyethylene glycols and other polymers having an ethylene glycol backbone, whether homopolymers or cross linked heteropolymers, block copolymers using ethylene glycol units, such as POLYOX®yethylene homopolymers (such as POLYOX®® N10/MW=100,000 POLYOX®-80/MW=200,000; POLYOX® 1105/MW=900,000; POLY OX®-301/MW=4,000,000; POLYOX®-303/MW=7,000,000, POLYOX® WSR-N-60K, all of which are tradenames of Union Carbide), hydroxypropylmethylcellulose (HPMC) of all molecular weights and grades (such as METOLOSE® 90SH50000, METOLOSE® 90SH30000, all of which are tradenames of Shin-Etsu Chemical company), Poloxamers (such as LUTROL® F-68, LUTROL® F-127, F-105 etc., all tradenames of BASF Chemicals), GENAPOL®, polyethylene glycols (PEG, such as PEG-1500, PEG-3500, PEG-4000, PEG-6000, PEG-8000, PEG-12000, PEG-20,000, etc.), natural gums (xanthan gum, locust bean gum, etc.) and cellulose derivatives (HC, HMC, HMPC, HPC, CP, CMC), polyacrylic acid-based polymers either as free or cross-linked and combinations thereof, biodegradable polymers such as poly lactic acids, polyglycolic acids and any combination thereof, whether a physical blend or cross-linked. In certain embodiments, the hydrogel components may be cross-linked. The hydrogel forming excipient(s) are typically present at 0.1-70% w/w, preferably 1-50% w/w or most preferably 1-30% w/w.

In certain embodiments the formulations may also include at least one controlled release modifier which is a substance that upon hydration of the dosage form will preferentially adhere to the drug molecules and thus reduce the rate of its diffusion from the oral dosage form. Such excipients may also reduce the rate of water uptake by the formulation and thus enable a more prolonged drug dissolution and release from the tablet. In general the selected excipient(s) are lipophilic and capable of naturally complexing to the hydrophobic or lipophilic drugs. The degree of association of the release modifier and the drug can be varied by altering the modifier-to-drug ratio in the formulation. In addition, such interaction may be appropriately enhanced by the appropriate combination of the release modifier with the active drug in the manufacturing process. Alternatively, the controlled release modifier may be a charged polymer either synthetic or biopolymer bearing a net charge, either positive or negative, and which is capable of binding to the active via electrostatic interactions thus modifying both its diffusion through the tablet and/or the kinetics of its permeation through the mucosal surface. Similarly to the other compounds mentioned above, such interaction is reversible and does not involve permanent chemical bonds with the active. In certain embodiments the controlled release modifier may typically be present at 0-80% w/w, preferably 1-20% w/w, most preferably 1-10% w/w.

In various embodiments the extended release formulations may also include other conventional components required for the development of oral dosage forms, which are known to those skilled in the art. These components may include one or more bulking agents (such as lactose USP, Starch 1500, mannitol, sorbitol, malitol or other non-reducing sugars; microcrystalline cellulose (e.g., AVICELO®), dibasic calcium phosphate dehydrate, sucrose, and mixtures thereof), at least one solubilizing agent(s) (such as cyclodextrins, pH adjusters, salts and buffers, surfactants, fatty acids, phospholipids, metals of fatty acids etc.), metal salts and buffers organic (such as acetate, citrate, tartrate, etc.) or inorganic (phosphate, carbonate, bicarbonate, borate, sulfate, sulfite, bisulfite, metabisulfite, chloride, etc.), salts of metals such as sodium, potassium, calcium, magnesium, etc.), at least one lubricant (such as stearic acid and divalent cations of, such as magnesium stearate, calcium stearate, etc., talc, glycerol monostearate and the like), one or more glidants (such as colloidal silicon dioxide, precipitated silicon dioxide, fumed silica (CAB-O-SIL® M-5P, trademark of Cabot Corporation), stearowet and sterotex, silicas (such as SILOID® and SILOX® silicas—trademarks of Grace Davison Products, Aerosil—trademark of Degussa Pharma), higher fatty acids, the metal salts thereof, hydrogenated vegetable oils and the like), flavors or sweeteners and colorants (such as aspartame, mannitol, lactose, sucrose, other artificial sweeteners; ferric oxides and FD&C lakes), additives to help stabilize the drug substance from chemical of physical degradation (such as anti-oxidants, anti-hydrolytic agents, aggregation-blockers etc. Anti-oxidants may include BHT, BHA, vitamins, citric acid, EDTA, sodium bisulfate, sodium metabisulfate, thiourea, methionine, surfactants, amino-acids, such as arginine, glycine, histidine, methionine salts, pH adjusters, chelating agents and buffers in the dry or solution form), one or more excipients that may affect tablet disintegration kinetics and drug release from the tablet, and thus pharmacokinetics (disintegrants such as those known to those skilled in the art and may be selected from a group consisting of starch, carboxy-methylcellulose type or crosslinked polyvinyl pyrrolidone (such as crosspovidone, PVP-XL), alginates, cellulose-based disintegrants (such as purified cellulose, methylcellulose, crosslinked sodium carboxy methylcellulose (Ac-Di-Sol) and carboxy methyl cellulose), low substituted hydroxypropyl ethers of cellulose, microcrystalline cellulose (such as AVICEL®), ion exchange resins (such as AMBRELITE® IPR 88), gums (such as agar, locust bean, karaya, pectin and tragacanth), guar gums, gum karaya, chitin and chitosan, smecta, gellan gum, isapghula husk, polacrillin potassium (Tulsion$^{339}$), gas-evolving disintegrants (such as citric acid and tartaric acid along with the sodium bicarbonate, sodium carbonate, potassium bicarbonate or calcium carbonate), sodium starch glycolate (such as EXPLOTAB® and PRIMOGEL®), starch DC and the likes, at least one biodegradable polymer of any type useful for extended drug release. Exemplary polymer compositions include, but are not limited to, polyanhydrides and co-polymers of lactic acid and glycolic acid, poly(dl-lactide-co-glycolide) (PLGA), poly(lactic acid) (PLA), poly(glycolic acid) (PGA), polyorthoesters, proteins, and polysaccharides.

In certain embodiments, the active agent(s) can be chemically modified to significantly modify the pharmacokinetics in plasma. This may be accomplished for example by conjugation with poly(ethylene glycol) (PEG), including site-specific PEGylation. PEGylation, which may improve drug performance by optimizing pharmacokinetics, decreasing immunogenicity and dosing frequency.

Methods of making a formulation of the active agent(s) described herein (e.g., ASBIs such as galangin, rutin, and analogues, derivatives, or prodrugs thereof) for GI or oral transmucosal delivery are also provided. One method includes the steps of powder grinding, dry powder mixing and tableting via direct compression. Alternatively, a wet granulation process may be used. Such a method (such as high shear granulation process) involves mixing the active ingredient and possibly some excipients in a mixer. The binder may be one of the excipients added in the dry mix state or dissolved in the fluid used for granulating. The granulating solution or suspension is added to the dry powders in the mixer and mixed until the desired characteristics are achieved. This usually produces a granule that will be of suitable characteristics for producing dosage forms with adequate dissolution time, content uniformity, and other physical characteristics. After the wet granulation step, the product is most often dried and/or then milled after drying to get a major percentage of the product within a desired size range. Sometimes, the product is dried after being wet sized using a device such as an oscillating granulator, or a mill. The dry granulation may then processed to get an acceptable size range by first screening with a sieving device, and then milling the oversized particles.

Additionally, the formulation may be manufactured by alternative granulation processes, all known to those skilled in the art, such as spray fluid bed granulation, extrusion and spheronization or fluid bed rotor granulation.

Additionally, the tablet dosage form of the invention may be prepared by coating the primary tablet manufactured as described above with suitable coatings known in the art. Such coatings are meant to protect the active cores against damage (abrasion, breakage, dust formation) against influences to which the cores are exposed during transport and storage (atmospheric humidity, temperature fluctuations), and naturally these film coatings can also be colored. The scaling effect of film coats against water vapor is expressed by the water vapor permeability. Coating may be performed by one of the available processes such as Wurster coating, dry coating, film coating, fluid bed coating, pan coating, etc. Typical coating materials include polyvinyl pyrrolidone (PVP), polyvinyl pyrrolidone vinyl acetate copolymer (PVPVA), polyvinyl alcohol (PVA), polyvinyl alcohol/polyethylene glycol copolymer (PVA/PEG), cellulose acetate phthalate, ethyl cellulose, gellan gum, maltodextrin, methacrylates, methyl cellulose, hydroxyl propyl methyl cellulose (HPMC of all grades and molecular weights), carrageenan, shellac and the like.

In certain embodiments the tablet core comprising the active agent(s) described herein can be coated with a bioadhesive and/or pH resistant material to enable material, such as those defined above, to improve bioadhesion of the tablet in the sublingual cavity.

In certain embodiments, the active agent(s) described herein (e.g., ASBIs such as galangin, rutin, and analogues, derivatives, or prodrugs thereof) are formulated as inclusion complexes. While not limited to cyclodextrin inclusion complexes, it is noted that cyclodextrin is the agent most frequently used to form pharmaceutical inclusion complexes. Cyclodextrins (CD) are cyclic oligomers of glucose, that typically contain 6, 7, or 8 glucose monomers joined by α-1,4 linkages. These oligomers are commonly called α-CD, β-CD, and γ-CD, respectively. Higher oligomers containing up to 12 glucose monomers are known, and contemplated to in the formulations described herein. Functionalized cyclodextrin inclusion complexes are also contemplated. Illustrative, but non-limiting functionalized cyclodextrins include, but are not limited to sulfonates, sulfonates and sulfinates, or disulfonates of hydroxybutenyl cyclodextrin; sulfonates, sulfonates and sulfinates, or disulfonates of mixed ethers of cyclodextrins where at least one of the ether substituents is hydroxybutenyl cyclodextrin. Illustrative cyclodextrins include a polysaccharide ether which comprises at least one 2-hydroxybutenyl substituent, wherein the at least one hydroxybutenyl substituent is sulfonated and sulfinated, or disulfonated, and an alkylpolyglycoside ether which comprises at least one 2-hydroxybutenyl substituent, wherein the at least one hydroxybutenyl substituent is sulfonated and sulfinated, or disulfonated. In various embodiments inclusion complexes formed between sulfonated hydroxybutenyl cyclodextrins and one or more of the active agent(s) described herein are contemplated. Methods of preparing cyclodextrins, and cyclodextrin inclusion complexes are found for example in U.S. Patent Publication No: 2004/0054164 and the references cited therein and in U.S. Patent Publication No: 2011/0218173 and the references cited therein.

Pharmacokinetics (PK) and Formulation Attributes

One advantage of the extended (controlled) release oral (GI or transmucosal) formulations described herein is that they can maintain the plasma drug concentration within a targeted therapeutic window for a longer duration than with immediate-release formulations, whether solid dosage forms or liquid-based dosage forms. The high peak plasma levels typically observed for such conventional immediate release formulations will be blunted by the prolonged release of the drug over 1 to 12 hours or longer. In addition, a rapid decline in plasma levels will be avoided since the drug will continually be crossing from the oral cavity into the bloodstream during the length of time of dissolution of the tablet, thus providing plasma pharmacokinetics with a more stable plateau. In addition, the dosage forms described herein may improve treatment safety by minimizing the potentially deleterious side effects due to the reduction of the peaks and troughs in the plasma drug pharmacokinetics, which compromise treatment safety.

In various embodiments the oral transmucosal formulations of the active agent(s) described herein designed to avoid the high peak plasma levels of intravenous and conventional immediate release oral dosage forms by utilizing the mucosa and by independently controlling both tablet disintegration (or erosion) and drug dissolution and release from the tablet over time to provide a safer delivery profile. The oral formulations described herein provide individual, repetitive doses that include a defined amount of the active agent.

An advantage of the bioadhesive oral transmucosal formulations described herein is that they exhibit highly consistent bioavailability and can maintain the plasma drug concentration within a targeted therapeutic window with significantly lower variability for a longer duration than currently available dosage forms, whether solid dosage forms or IV dosage forms. In addition, a rapid decline in plasma levels is avoided since the drug is continually crossing from the oral cavity or GI tract into the bloodstream during the length of time of dissolution of the tablet or longer, thus providing plasma pharmacokinetics with an extended plateau phase as compared to the conventional immediate release oral dosage forms. Further, the dosage forms described herein can improve treatment safety by minimizing the potentially deleterious side effects due to the relative reduction of the peaks and troughs in the plasma drug pharmacokinetics, which compromise treatment safety and is typical of currently available dosage forms.

In various embodiments bioadhesive formulations described herein can be designed to manipulate and control the pharmacokinetic profile of the active agent(s) described herein. As such, the formulations can be adjusted to achieve 'slow' disintegration times (and erosion kinetic profiles) and slow drug release and thus enable very prolonged pharmacokinetic profiles that provide sustained drug action. Although such formulations may be designed to still provide a fast onset, they are mostly intended to enable the sustained drug PK and effect while maintaining the other performance attributes of the tablet such as bioadhesion, reproducibility of action, blunted $C_{max}$, etc.

The performance and attributes of the bioadhesive transmucosal formulations of this invention are independent of the manufacturing process. A number of conventional, well-established and known in the art processes can be used to manufacture the formulations of the present invention (such as wet and dry granulation, direct compression, etc.) without impacting the dosage form physicochemical properties or in vivo performance.

An illustrative mathematical ratio that demonstrates the prolonged plateau phase of the measured blood plasma levels of the active agent(s) described herein, following administration of the dosage forms of the invention is the term "Optimal Therapeutic Targeting Ratio" or "OTTR", which represents the average time that the drug is present at therapeutic levels, defined as time within which the drug plasma concentration is maintained above 50% of $C_{max}$ normalized by the drug's elimination half-life multiplied by the ratio of the $C_{max}$ obtained in the dosage form of interest over the normalized $C_{max}$ following IV administration of equivalent doses. In certain embodiments the OTTR can be calculated by the formula:

$$\text{OTTR} = (C^{IV}_{max}/C_{max}) \times (\text{Dose}/\text{Dose}^{IV})(\text{Time above } 50\% \text{ of } C_{max})/(\text{Terminal}^{IV} \text{ elimination half-life of the drug}).$$

In certain embodiments the OTTR is greater than about 15, or greater than about 20, or greater than about 25, or greater than about 30, or greater than about 40, or greater than about 50.

Administration

In certain embodiments one or more active agents described herein (e.g., ASBIs such as galangin, rutin, and analogues, derivatives, or prodrugs thereof) are administered to a mammal in need thereof, e.g., to a mammal at risk for or suffering from a pathology characterized by abnormal processing of amyloid precursor proteins, a mammal at risk for progression of MCI to Alzheimer's disease, and so forth. In certain embodiments the active agent(s) are administered to prevent or delay the onset of a pre-Alzheimer's cognitive dysfunction, and/or to ameliorate one or more symptoms of a pre-Alzheimer's cognitive dysfunction, and/or to prevent or delay the progression of a pre-Alzheimer's condition or cognitive dysfunction to Alzheimer's disease, and/or to promote the processing of amyloid precursor protein (APP) by a non-amyloidogenic pathway. In certain embodiments one or more active agent(s) are administered for the treatment of early stage, mid stage, or late-stage Alzheimer's disease, e.g., to reduce the severity of the disease, and/or to ameliorate one or more symptoms of the disease, and/or to slow the progression of the disease.

In various embodiments the active agent(s) described herein (e.g., ASBIs such as galangin, rutin, and analogues, derivatives, or prodrugs thereof) can be administered by any of a number of routes. Thus, for example they can be administered orally, parenterally, (intravenously (IV), intramuscularly (IM), depo-IM, subcutaneously (SQ), and depo-SQ), sublingually, intranasally (inhalation), intrathecally, transdermally (e.g., via transdermal patch), topically, ionophoretically or rectally. Typically the dosage form is selected to facilitate delivery to the brain (e.g., passage through the blood brain barrier). In this context it is noted that the compounds described herein are readily delivered to the brain. Dosage forms known to those of skill in the art are suitable for delivery of the compound.

The active agent(s) are administered in an amount/dosage regimen sufficient to exert a prophylactically and/or therapeutically useful effect in the absence of undesirable side effects on the subject treated. The specific amount/dosage regimen will vary depending on the weight, gender, age and health of the individual; the formulation, the biochemical nature, bioactivity, bioavailability and the side effects of the particular compound.

In certain embodiments the therapeutically or prophylactically effective amount may be determined empirically by testing the agent(s) in known in vitro and in vivo model systems for the treated disorder. A therapeutically or prophylactically effective dose can be determined by first administering a low dose, and then incrementally increasing until a dose is reached that achieves the desired effect with minimal or no undesired side effects.

In certain embodiments, when administered orally, an administered amount of the agent(s) described herein effective to prevent or delay the onset of a pre-Alzheimer's cognitive dysfunction, and/or to ameliorate one or more symptoms of a pre-Alzheimer's cognitive dysfunction, and/or to prevent or delay the progression of a pre-Alzheimer's condition or cognitive dysfunction to Alzheimer's disease, and/or to promote the processing of amyloid precursor protein (APP) by a non-amyloidogenic pathway, and/or to treat or prevent AD ranges from about 0.1 mg/day to about 500 mg/day or about 1,000 mg/day, or from about 0.1 mg/day to about 200 mg/day, for example, from about 1 mg/day to about 100 mg/day, for example, from about 5 mg/day to about 50 mg/day. In some embodiments, the subject is administered the compound at a dose of about 0.05 to about 0.50 mg/kg, for example, about 0.05 mg/kg, 0.10 mg/kg, 0.20 mg/kg, 0.33 mg/kg, 0.50 mg/kg. It is understood that while a patient may be started at one dose, that dose may be varied (increased or decreased, as appropriate) over time as the patient's condition changes. Depending on outcome evaluations, higher doses may be used. For example, in certain embodiments, up to as much as 1000 mg/day can be administered, e.g., 5 mg/day, 10 mg/day, 25 mg/day, 50 mg/day, 100 mg/day, 200 mg/day, 300 mg/day, 400 mg/day, 500 mg/day, 600 mg/day, 700 mg/day, 800 mg/day, 900 mg/day or 1000 mg/day.

In various embodiments, active agent(s) described herein can be administered parenterally, for example, by IV, IM, depo-IM, SC, or depo-SC. When administered parenterally, a therapeutically effective amount of about 0.5 to about 100 mg/day, preferably from about 5 to about 50 mg daily should be delivered. When a depot formulation is used for injection once a month or once every two weeks, the dose should be about 0.5 mg/day to about 50 mg/day, or a monthly dose of from about 15 mg to about 1,500 mg. In part because of the forgetfulness of the patients with Alzheimer's disease, it is preferred that the parenteral dosage form be a depo formulation.

In various embodiments, the active agent(s) described herein can be administered sublingually. When given sublingually, the compounds and/or analogs thereof can be given one to four times daily in the amounts described above for IM administration.

In various embodiments, the active agent(s) described herein can be administered intranasally. When given by this route, the appropriate dosage forms are a nasal spray or dry powder, as is known to those skilled in the art. The dosage of compound and/or analog thereof for intranasal administration is the amount described above for IM administration.

In various embodiments, the active agent(s) described herein can be administered intrathecally. When given by this route the appropriate dosage form can be a parenteral dosage form as is known to those skilled in the art. The dosage of compound and/or analog thereof for intrathecal administration is the amount described above for IM administration.

In certain embodiments, the active agent(s) described herein can be administered topically. When given by this route, the appropriate dosage form is a cream, ointment, or patch. When administered topically, the dosage is from about 1.0 mg/day to about 200 mg/day. Because the amount that can be delivered by a patch is limited, two or more patches may be used. The number and size of the patch is not important, what is important is that a therapeutically effective amount of compound be delivered as is known to those skilled in the art. The compound can be administered rectally by suppository as is known to those skilled in the art. When administered by suppository, the therapeutically effective amount is from about 1.0 mg to about 500 mg.

In various embodiments, the active agent(s) described herein can be administered by implants as is known to those skilled in the art. When administering the compound by implant, the therapeutically effective amount is the amount described above for depot administration.

In various embodiments the dosage forms can be administered to the subject 1, 2, 3, or 4 times daily. It is preferred that the compound be administered either three or fewer times, more preferably once or twice daily. It is preferred that the agent(s) be administered in oral dosage form.

It should be apparent to one skilled in the art that the exact dosage and frequency of administration will depend on the particular condition being treated, the severity of the condition being treated, the age, weight, general physical condition of the particular patient, and other medication the individual may be taking as is well known to administering physicians who are skilled in this art.

While the compositions and methods are described herein with respect to use in humans, they are also suitable for animal, e.g., veterinary use. Thus certain preferred organisms include, but are not limited to humans, non-human primates, canines, equines, felines, porcines, ungulates, largomorphs, and the like.

The foregoing formulations and administration methods are intended to be illustrative and not limiting. It will be appreciated that, using the teaching provided herein, other suitable formulations and modes of administration can be readily devised.

Combination Therapies

In certain embodiments, the active agent(s) described herein (e.g., ASBIs such as galangin, rutin, and analogues, derivatives, or prodrugs thereof) can be used in combination with other therapeutic agents or approaches used to treat or prevent diseases characterized by amyloid deposits in the brain, including MCI and/or AD. Such agents or approaches include: acetylcholinesterase inhibitors (including without limitation, e.g., (-)-phenserine enantiomer, tacrine, ipidacrine, galantamine, donepezil, icopezil, zanapezil, rivastigmine, huperzine A, phenserine, physostigmine, neostigmine, pyridostigmine, ambenonium, demarcarium, edrophonium, ladostigil and ungeremine); NMDA receptor antagonist (including without limitations e.g., Memantine); muscarinic receptor agonists (including without limitation, e.g., Talsaclidine, AF-102B, AF-267B (NGX-267)); nicotinic receptor agonists (including without limitation, e.g., Ispronicline (AZD-3480)); beta-secretase inhibitors (including without limitations e.g., thiazolidinediones, including rosiglitazone and pioglitazone); gamma-secretase inhibitors (including without limitation, e.g., semagacestat (LY-450139), MK-0752, E-2012, BMS-708163, PF-3084014, begacestat (GSI-953), and NICS-15); inhibitors of Aβ aggregation (including without limitation, e.g., Clioquinol (PBT1), PBT2, tramiprosate (homotaurine), Scyllo-inositol (a.k.a., scyllo-cyclohexanehexol, AZD-103 and ELND-005), passive immunotherapy with AP fragments (including without limitations e.g., Bapineuzemab) and Epigallocatechin-3-gallate (EGCg)); anti-inflammatory agents such as cyclooxygenase II inhibitors; anti-oxidants such as Vitamin E and ginkolides; immunological approaches, such as, for example, immunization with Aβ peptide or administration of anti-AP peptide antibodies; statins; and direct or indirect neurotrophic agents such as Cerebrolysin™, AIT-082 (Emilieu (2000) *Arch. Neurol.* 57:454), Netrin (Luorenco (2009) *Cell Death Differ* 16: 655-663), Netrin mimetics, NGF, NGF mimetics, BDNF and other neurotrophic agents of the future, agents that promote neurogenesis e.g. stem cell therapy. Further pharmacologic agents useful in combination with tropisetron, disulfiram, honokiol and/or nimetazepam to treat or prevent diseases characterized by amyloid deposits in the brain, including MCI and/or AD, are described, e.g., in Mangialasche, et al., *Lancet Neurol* (2010) 9:702-716.

In various embodiments, combination therapy with one or more of the active agents described herein expressly excludes administration of these agents in conjunction with an acetylcholinesterase inhibitor.

Use of ASBIs in Age Related Macular Degeneration and Glaucoma.

While in various embodiments, the use of ASBIs are contemplated for the preventing or delaying the onset of a pre-Alzheimer's condition and/or cognitive dysfunction, and/or ameliorating one or more symptoms of a pre-Alzheimer's condition and/or cognitive dysfunction, or preventing or delaying the progression of a pre-Alzheimer's condition or cognitive dysfunction to Alzheimer's disease, and/or for the treatment of Alzheimer's disease, other uses of ASBIs are also contemplated. In particular, in certain embodiments, the use of ASBIs is contemplated for the treatment and/or prophylaxis of age-related macular degeneration and/or glaucoma.

Without being bound to a particular theory, it is believed that abnormal extracellular deposition of proteins may contribute to age-related macular degeneration (AMD) pathogenesis and progression, which is also the case in Alzheimer's disease and atherosclerosis. In both conditions, the protein deposits contain many shared constituents such as apoE, complement, and AP peptides. For instance, in human AMD, Aβ peptide deposition is associated with drusen, where it accumulates and colocalizes with activated complement components (Anderson et al. (2004) *Exp. Eye. Res.,* 78:243-256; Dentchev et al. (2003) *Mol. Vis.,* 9: 184-190; Johnson et al. (2002) *Proc Natl Acad Sci USA* 99: 11830-11835.). Luibl et al. (2006) *J. Clin. Invest.,* 116: 378-385, showed the presence of potentially toxic amyloid oligomers in drusen, sub-RPE basal deposits, and RPE of human donor eyes using an antibody that specifically recognizes the oligomeric form of Aβ. These Aβ oligomers were not detected in control age-matched donor eyes without drusen. Isas et al. (2010) *Invest. Ophthalinol Vis. Sci.,* 51: 1304-1310, also detected soluble as well as mature Aβ fibrils in drusen. Collectively, these findings implicate Aβ in the pathogenesis of AMD. In addition, Aβ peptide has been detected in sub-RPE basal deposits and neovascular lesions in a murine model of AMD (Ding et al. (2008) *Vision Res.,* 48: 339-345; Malek et al. (2005) *Proc Natl Acad Sci USA,* 102: 11900-11905). In this model, aged human APOE4-targeted replacement mice (APOE4 mice) fed a high-fat, cholesterol-enriched (HFC) diet (APOE4-HFC mice) exhibit morphologic hallmarks observed in both dry and wet AMD. These hallmarks include thick diffuse sub-RPE deposits, lipid- and protein-containing focal drusen-like deposits, thickening of Bruch's membrane, patchy regions of RPE atrophy opposed to areas of photoreceptor degeneration, and CNV (Malek et al. (2005) *Proc Natl Acad Sci USA,* 102: 11900-11905). It is believed that, in the APOE4-HFC mouse model of AMD, Aβ accumulation provokes damage at the level of the RPE/choroid and has previously been shown that systemic administration of anti-Aβ40-specific antibodies can partially attenuate the decline in visual function exhibited in this model (Ding et al. (2008) *Vision Res.,* 48: 339-345). It has also been demonstrated that anti-Aβ immunotherapy simultaneously targeting both Aβ40 and Aβ42 blocks histopathologic changes and completely protects visual function in APOE4-HFC mice (Ding et al. (2011) *Proc. Nat'l. Acad. Sci. U.S.A.,* 108(28): E279-E287).

Without being bound by a particular theory, it is believed that APP processing to Aβ in the eye occurs by the activities of BACE and γ-secretase in the retina and retinal pigmented epithelial (RPE) cell layers and that sAPPα and Aβ are secreted into the vitreous humor (see, e.g., (Prakasam et al. (2008) *J. Alzh. Dis.,* 20: 1243-1253). Aβ is further transported into the aqueous humor where it is readily measured.

In view of these findings, it is believe that ASBIs, e.g., as described herein, can find use in the treatment or prophylaxis of age-related macular degeneration (AMD) and/or glaucoma. Accordingly, it is believed that ASBIs can be administered to a subject to slow or prevent the appearance of AMD (and/or glaucoma), and/or to reduce one or more symptoms of AMD, and/or to slow, stop, or reverse progression of the disease. In various embodiments one or more ASBIs (e.g., any one or more of the active agent(s) described herein) are administered to a subject (e.g., a human, a non-human mammal) for these purposes. As described above, in various embodiments, the ASBI is administered via a route selected from the group consisting of oral delivery, isophoretic delivery, transdermal delivery, parenteral delivery, aerosol administration, administration via inhalation, intravenous administration, and rectal administration.

In certain embodiments, the administration is directly to the eye. Thus for example, in certain embodiments, the agent(s) can be administered to the eye in the form of eye drops, via intraocular injection, and the like.

Typically the ASBIs are administered in an effective amount for the treatment and/or prophylaxis of AMD or glaucoma, where the effective amount will vary by the modality of administration. In certain embodiments effective amount is an amount sufficient to mitigating in a mammal one or more symptoms associated with age-related macular degeneration (AMD). In certain embodiments the effective amount is an amount, an amount sufficient to reduce the risk or delaying the onset, and/or reduce the ultimate severity of a AMD disease (or glaucoma) characterized by reduction of Aβ in the vitreous and/or aqueous humor and/or the amyloid deposits on the retina and/or the RPE cell layer.

Assay Systems to Evaluate APP Processing

Without being bound to a particular theory, it is believed that the active agent(s) described herein (e.g., ASBIs such as galangin, rutin, and analogues, derivatives, or prodrugs thereof) promote processing of APP by the nonamyloidogenic pathway and/or reduce or inhibits processing of APP by the amyloidogenic pathway. In the nonamyloidogeic pathway, APP is first cleaved by α-secretase within the Aβ sequence, releasing the APPsα ectodomain ("sAPPα"). In contrast, the amyloidogenic pathway is initiated when β-secretase cleaves APP at the amino terminus of the Aβ, thereby releasing the APPsβ ectodomain ("sAPPβ"). APP processing by the nonamyloidogenic and amyloidogenic pathways is known in the art and reviewed, e.g., by Xu (2009) *J Alzheimers Dis.*, 16(2): 211-224, and De Strooper, et al. (2010 *Nat Rev Neural* 6(2): 99-107.

One method to evaluate the efficacy of the active agent(s) is to determine a reduction or elimination in the level of APP processing by the amyloidogenic pathway, e.g., a reduction or elimination in the level of APP processing by β-secretase cleavage in response to the administration of the agent(s) of interest. Assays for determining the extent of APP cleavage at the β-secretase cleavage site are well known in the art. Illustrative assays are described, for example, in U.S. Pat. Nos. 5,744,346 and 5,942,400. Kits for determining the presence and levels in a biological sample of sAPPα and sAPPβ, as well as APPneo and Aβ commercially available, e.g., from PerkinElmer.

ASBI Assay.

ASBI activity of any of the compounds described herein can readily be verified using, for example, assays illustrated in the examples provided herein. Basically, in certain embodiments a pair of assays are utilized to identify compounds that inhibit BACE cleavage of the MBP-C125 APP substrate, resulting in the inhibition of the production of C99 but not the β-site peptide substrate (P5-P5').

As illustrated in the Examples, in one embodiment, an MBP-C125 APP695wt fusion protein can be used as one of the substrates. The second substrate can be the commercially available P5-P5' fluorescence substrate. Each of these substrates is incubated with recombinant BACE (R&D (cat #931-AS-050) in, for example, a 96 well plate format. For the MBP-C125 substrate the C-99 product from the BACE cleavage can be measured using an AlphaLisa assay as a readout. For the P5-5' substrate the loss of fluorescence upon BACE cleavage can be used as the readout. An ASBI would inhibit the BACE cleavage of the MBP-C125 substrate while not being inhibitory of the fluorescence substrate.

Other Cell Free Assays

Illustrative assays that can be used to demonstrate the inhibitory activity of the active agent(s) are described, for example, in WO 00/17369, WO 00/03819, and U.S. Pat. Nos. 5,942,400 and 5,744,346. Such assays can be performed in cell-free incubations or in cellular incubations using cells expressing an alpha-secretase and/or beta-secretase and an APP substrate having a alpha-secretase and beta-secretase cleavage sites.

In one illustrative embodiment, the agent(s) of interest are contacted with an APP substrate containing alpha-secretase and beta-secretase cleavage sites of APP, for example, a complete APP or variant, an APP fragment, or a recombinant or synthetic APP substrate containing the amino acid sequence: KM-DA or NL-DA (APP-SW), is incubated in the presence of an alpha-secretase and/or beta-secretase enzyme, a fragment thereof, or a synthetic or recombinant polypeptide variant having alpha-secretase or beta-secretase activity and effective to cleave the alpha-secretase or beta-secretase cleavage sites of APP, under incubation conditions suitable for the cleavage activity of the enzyme. agent(s) having the desired activity reduce or prevent cleavage of the APP substrate. Suitable substrates optionally include derivatives that may be fusion proteins or peptides that contain the substrate peptide and a modification useful to facilitate the purification or detection of the peptide or its alpha-secretase and/or beta-secretase cleavage products. Useful modifications include the insertion of a known antigenic epitope for antibody binding; the linking of a label or detectable moiety, the linking of a binding substrate, and the like.

Suitable incubation conditions for a cell-free in vitro assay include, for example: approximately 200 nanomolar to 10 micromolar substrate, approximately 10 to 200 picomolar enzyme, and approximately 0.1 nanomolar to 10 micromolar of the agent(s), in aqueous solution, at an approximate pH of 4-7, at approximately 37° C., for a time period of approximately 10 minutes to 3 hours. These incubation conditions are exemplary only, and can be varied as required for the particular assay components and/or desired measurement system. Optimization of the incubation conditions for the particular assay components should account for the specific alpha-secretase and/or beta-secretase enzyme used and its pH optimum, any additional enzymes and/or markers that might be used in the assay, and the like. Such optimization is routine and will not require undue experimentation.

Another illustrative assay utilizes a fusion peptide having maltose binding protein (MBP) fused to the C-terminal 125 amino acids of APP-SW. The MBP portion is captured on an assay substrate by anti-MBP capture antibody. Incubation of the captured fusion protein in the presence of alpha-secretase and/or beta-secretase results in cleavage of the substrate at the alpha-secretase and/or beta-secretase cleavage sites, respectively. This system can be used to screen for the inhibitory activity of the agent(s) of interest. Analysis of the cleavage activity can be, for example, by immunoassay of cleavage products. One such immunoassay detects a unique epitope exposed at the carboxy terminus of the cleaved fusion protein, for example, using the antibody SW192. This assay is described, for example, in U.S. Pat. No. 5,942,400.

Cellular Assays

Numerous cell-based assays can be used to evaluate the activity of agent(s) of interest on relative alpha-secretase activity to beta-secretase activity and/or processing of APP to release amyloidogenic versus non-amyloidogenic Aβ oligomers. Contact of an APP substrate with an alpha-secretase and/or beta-secretase enzyme within the cell and in the presence or absence of the agent(s) can be used to demonstrate alpha-secretase promoting and/or beta-secretase inhibitory activity of the agent( ). Preferably, the assay in the presence of the agent(s) provides at least about 30%, most preferably at least about 50% inhibition of the enzymatic activity, as compared with a non-inhibited control.

In one embodiment, cells that naturally express alpha-secretase and/or beta-secretase are used. Alternatively, cells are modified to express a recombinant alpha-secretase and/or beta-secretase or synthetic variant enzymes, as discussed above. The APP substrate may be added to the culture medium and is preferably expressed in the cells. Cells that naturally express APP, variant or mutant forms of APP, or cells transformed to express an isoform of APP, mutant or variant APP, recombinant or synthetic APP, APP fragment, or synthetic APP peptide or fusion protein containing the alpha-secretase and/or beta-secretase APP cleavage sites can be used, provided that the expressed APP is permitted to contact the enzyme and enzymatic cleavage activity can be analyzed.

Human cell lines that normally process AP from APP provide a useful means to assay inhibitory activities of the agent(s). Production and release of Aβ and/or other cleavage products into the culture medium can be measured, for example by immunoassay, such as Western blot or enzyme-linked immunoassay (EIA) such as by ELISA.

Cells expressing an APP substrate and an active alpha-secretase and/or beta-secretase can be incubated in the presence of the agents to demonstrate relative enzymatic activity of the alpha-secretase and/or beta-secretase as compared with a control. Relative activity of the alpha-secretase to the beta-secretase can be measured by analysis of one or more cleavage products of the APP substrate. For example, inhibition of beta-secretase activity against the substrate APP would be expected to decrease release of specific beta-secretase induced APP cleavage products such as Aβ, sAPPβ and APPneo. Promotion or enhancement of alpha-secretase activity against the substrate APP would be expected to increase release of specific alpha-secretase induced APP cleavage products such as sAPPα and p3 peptide.

Although both neural and non-neural cells process and release Aβ, levels of endogenous beta-secretase activity are low and often difficult to detect by EIA. The use of cell types known to have enhanced beta-secretase activity, enhanced processing of APP to Aβ, and/or enhanced production of Aβ are therefore preferred. For example, transfection of cells with the Swedish Mutant form of APP (APP-SW); with the Indiana Mutant form (APP-IN); or with APP-SW-IN provides cells having enhanced beta-secretase activity and producing amounts of Aβ that can be readily measured.

In such assays, for example, the cells expressing APP, alpha-secretase and/or beta-secretase are incubated in a culture medium under conditions suitable for alpha-secretase and/or beta-secretase enzymatic activity at its cleavage site on the APP substrate. On exposure of the cells to the agent(s), the amount of AP released into the medium and/or the amount of CTF99 fragments of APP in the cell lysates is reduced as compared with the control. The cleavage products of APP can be analyzed, for example, by immune reactions with specific antibodies, as discussed above.

Preferred cells for analysis of alpha-secretase and/or beta-secretase activity include primary human neuronal cells, primary transgenic animal neuronal cells where the transgene is APP, and other cells such as those of a stable 293 cell line expressing APP, for example, APP-SW.

In vivo Assays: Animal Models

Various animal models can be used to analyze the activity of agent(s) of interest on relative alpha-secretase and/or beta-secretase activity and/or processing of APP to release Aβ. For example, transgenic animals expressing APP substrate, alpha-secretase and/or beta-secretase enzyme can be used to demonstrate inhibitory activity of the agent(s). Certain transgenic animal models have been described, for example, in U.S. Pat. Nos. 5,877,399; 5,612,486; 5,387,742; 5,720,936; 5,850,003; 5,877,015, and 5,811,633, and in Ganes et al., 1995, Nature 373:523. Preferred are animals that exhibit characteristics associated with the pathophysiology of AD. Administration of the agent(s) to the transgenic mice described herein provides an alternative method for demonstrating the inhibitory activity of the agent(s). Administration of the agent(s) in a pharmaceutically effective carrier and via an administrative route that reaches the target tissue in an appropriate therapeutic amount is also preferred.

Inhibition of beta-secretase mediated cleavage of APP at the beta-secretase cleavage site and of Aβ release can be analyzed in these animals by measure of cleavage fragments in the animal's body fluids such as cerebral fluid or tissues. Likewise, promotion or enhancement of alpha-secretase mediated cleavage of APP at the alpha-secretase cleavage site and of release of sAPPα can be analyzed in these animals by measure of cleavage fragments in the animal's body fluids such as cerebral fluid or tissues. In certain embodiments, analysis of brain tissues for Aβ deposits or plaques is preferred.

On contacting an APP substrate with an alpha-secretase and/or beta-secretase enzyme in the presence of the agent(s) under conditions sufficient to permit enzymatic mediated cleavage of APP and/or release of Aβ from the substrate, desirable agent(s) are effective to reduce beta-secretase-mediated cleavage of APP at the beta-secretase cleavage site and/or effective to reduce released amounts of Aβ. The agent(s) are also preferably effective to enhance alpha-secretase-mediated cleavage of APP at the alpha-secretase cleavage site and to increase released amounts of sAPPα. Where such contacting is the administration of the agent(s) to an animal model, for example, as described above, the agent(s) is effective to reduce Aβ deposition in brain tissues of the animal, and to reduce the number and/or size of beta amyloid plaques. Where such administration is to a human subject, the agent(s) is effective to inhibit or slow the progression of disease characterized by enhanced amounts of Aβ, to slow the progression of AD in the, and/or to prevent onset or development of AD in a patient at risk for the disease.

Methods of Monitoring Clinical Efficacy

In various embodiments, the effectiveness of treatment can be determined by comparing a baseline measure of a parameter of disease before administration of the agent(s) (e.g., ASBIs such as galangin, rutin, and analogues, derivatives, or prodrugs thereof) is commenced to the same parameter one or more time points after the agent(s) or analog has been administered. One illustrative parameter that can be measured is a biomarker (e.g., a peptide oligomer) of APP processing. Such biomarkers include, but are not limited to increased levels of sAPPα, p3 (Aβ17-42 or Aβ17-40), sAPPβ, soluble Aβ40, and/or soluble Aβ42 in the blood, plasma, serum, urine, mucous or cerebrospinal fluid (CSF). Detection of increased levels of sAPPα and/or p3, and decreased levels of sAPPβ and/or APPneo is an indicator that the treatment is effective. Conversely, detection of decreased levels of sAPPα and/or p3, and/or increased levels of sAPPβ, APPneo, Tau or phospho-Tau (pTau) is an indicator that the treatment is not effective.

Another parameter to determine effectiveness of treatment is the level of amyloid plaque deposits in the brain. Amyloid plaques can be determined using any method known in the art, e.g., as determined by CT, PET, PIB-PET and/or MRI. Administration of the agent(s) (e.g., ASBIs such as galangin, rutin, and analogues, derivatives, or prodrugs thereof) can result in a reduction in the rate of plaque formation, and even a retraction or reduction of plaque deposits in the brain. Effectiveness of treatment can also be determined by observing a stabilization and/or improvement of cognitive abilities of the subject. Cognitive abilities can be evaluated using any art-accepted method, including for example, Clinical Dementia Rating (CDR), the mini-mental state examination (MMSE) or Folstein test, evaluative criteria listed in the DSM-IV (Diagnostic and Statistical Manual of Mental Disorders, Fourth Edition) or DSM-V, and the like.

Clinical efficacy can be monitored using any method known in the art. Measurable biomarkers to monitor efficacy include, but are not limited to, monitoring blood, plasma, serum, urine, mucous or cerebrospinal fluid (CSF) levels of sAPPα, sAPPβ, Aβ42, Aβ40, APPneo and p3 (e.g., Aβ17-42 or Aβ17-40). Detection of increased levels of sAPPα and/or p3, and decreased levels of sAPPβ and/or APPneo are indicators that the treatment or prevention regime is efficacious. Conversely, detection of decreased levels of sAPPα and/or p3, and increased levels of sAPPβ and/or APPneo are indicators that the treatment or prevention regime is not efficacious. Other biomarkers include Tau and phospho-Tau (pTau). Detection of decreased levels of Tau and pTau are indicators that the treatment or prevention regime is efficacious.

Efficacy can also be determined by measuring amyloid plaque load in the brain. The treatment or prevention regime is considered efficacious when the amyloid plaque load in the brain does not increase or is reduced. Conversely, the treatment or prevention regime is considered inefficacious when the amyloid plaque load in the brain increases. Amyloid plaque load can be determined using any method known in the art, e.g., including CT, PET, PIS-PET and/or MR1.

Efficacy can also be determined by measuring the cognitive abilities of the subject. Cognitive abilities can be measured using any method known in the art. Illustrative tests include assigning a Clinical Dementia Rating (CDR) score or applying the mini mental state examination (MMSE) (Folstein, et al., *Journal of Psychiatric Research* 12 (3): 189-98). Subjects who maintain the same score or who achieve an improved score, e.g., when applying the CDR or MMSE, indicate that the treatment or prevention regime is efficacious. Conversely, subjects who receive a score indicating diminished cognitive abilities, e.g., when applying the CDR or MMSE, indicate that the treatment or prevention regime has not been efficacious.

In certain embodiments, the monitoring methods can entail determining a baseline value of a measurable biomarker or parameter (e.g., amyloid plaque load or cognitive abilities) in a subject before administering a dosage of the agent(s), and comparing this with a value for the same measurable biomarker or parameter after treatment.

In other methods, a control value (e.g., a mean and standard deviation) of the measurable biomarker or parameter is determined for a control population. In certain embodiments, the individuals in the control population have not received prior treatment and do not have AD, MCI, nor are at risk of developing AD or MCI. In such cases, if the value of the measurable biomarker or clinical parameter approaches the control value, then treatment is considered efficacious. In other embodiments, the individuals in the control population have not received prior treatment and have been diagnosed with AD or MCI. In such cases, if the value of the measurable biomarker or clinical parameter approaches the control value, then treatment is considered inefficacious.

In other methods, a subject who is not presently receiving treatment but has undergone a previous course of treatment is monitored for one or more of the biomarkers or clinical parameters to determine whether a resumption of treatment is required. The measured value of one or more of the biomarkers or clinical parameters in the subject can be compared with a value previously achieved in the subject after a previous course of treatment. Alternatively, the value measured in the subject can be compared with a control value (mean plus standard deviation/ANOVA) determined in population of subjects after undergoing a course of treatment. Alternatively, the measured value in the subject can be compared with a control value in populations of prophylactically treated subjects who remain free of symptoms of disease, or populations of therapeutically treated subjects who show amelioration of disease characteristics. In such cases, if the value of the measurable biomarker or clinical parameter approaches the control value, then treatment is considered efficacious and need not be resumed. In all of these cases, a significant difference relative to the control level (e.g., more than a standard deviation) is an indicator that treatment should be resumed in the subject.

In certain embodiments the tissue sample for analysis is typically blood, plasma, serum, urine, mucous or cerebrospinal fluid from the subject.

Kits.

In various embodiments, the active agent(s) (e.g., APP specific BACE inhibitor (ASBI) such as galangin, rutin, and analogues, derivatives, a tautomer or stereoisomer thereof, or prodrug thereof as described herein) can be enclosed in multiple or single dose containers. The enclosed agent(s) can be provided in kits, for example, including component parts that can be assembled for use. For example, an active agent in lyophilized form and a suitable diluent may be provided as separated components for combination prior to use. A kit may include an active agent and a second therapeutic agent for co-administration. The active agent and second therapeutic agent may be provided as separate component parts. A kit may include a plurality of containers, each container holding one or more unit dose of the compounds. The containers are preferably adapted for the desired mode of administration, including, but not limited to tablets, gel capsules, sustained-release capsules, and the like for oral administration; depot products, pre-filled syringes, ampules, vials, and the like for parenteral administration; and patches, medipads, creams, and the like for topical administration, e.g., as described herein.

In certain embodiments, a kit is provided where the kit comprises: one or more ASBI compounds described herein, or prodrug, a tautomer or stereoisomer thereof, or pharmaceutically acceptable salt or solvate of said compound, said stereoisomer, or said tautomer or prodrug preferably provided as a pharmaceutical composition and in a suitable container or containers and/or with suitable packaging; optionally one or more additional active agents, which if present are preferably provided as a pharmaceutical composition and in a suitable container or containers and/or with suitable packaging; and optionally instructions for use, for example written instructions on how to administer the compound or compositions.

In another embodiment, a kit is provided that comprises a single container or multiple containers: (a) a pharmaceutically acceptable composition comprising one or more ASBI compounds described and/or claimed herein, or a tautomer or stereoisomer thereof, or pharmaceutically acceptable salt or solvate of said compound, said stereoisomer, or said tautomer, optionally a pharmaceutically acceptable composition comprising one or more additional therapeutic agents; and optionally instructions for use their use. The kit may optionally comprise labeling (e.g., instructional materials) appropriate to the intended use or uses.

As with any pharmaceutical product, the packaging material(s) and/or container(s) are designed to protect the stability of the product during storage and shipment. In addition, the kits can include instructions for use or other informational material that can advise the user such as, for example, a physician, technician or patient, regarding how to properly administer the composition(s) as prophylactic, therapeutic, or ameliorative treatment of the disease of concern. In some embodiments, instructions can indicate or suggest a dosing regimen that includes, but is not limited to, actual doses and monitoring procedures.

In some embodiments, the instructions can include informational material indicating that the administering of the compositions can result in adverse reactions including but not limited to allergic reactions such as, for example, anaphylaxis. The informational material can indicate that allergic reactions may exhibit only as mild pruritic rashes or may be severe and include erythroderma, vasculitis, anaphylaxis, Steven-Johnson syndrome, and the like. In certain embodiments the informational material(s) may indicate that anaphylaxis can be fatal and may occur when any foreign protein is introduced into the body. In certain embodiments the informational material may indicate that these allergic reactions can manifest themselves as urticaria or a rash and develop into lethal systemic reactions and can occur soon after exposure such as, for example, within 10 minutes. The informational material can further indicate that an allergic reaction may cause a subject to experience paresthesia, hypotension, laryngeal edema, mental status changes, facial or pharyngeal angioedema, airway obstruction, bronchospasm, urticaria and pruritus, serum sickness, arthritis, allergic nephritis, glomerulonephritis, temporal arthritis, eosinophilia, or a combination thereof.

While the instructional materials typically comprise written or printed materials they are not limited to such. Any medium capable of storing such instructions and communicating them to an end user is contemplated by this invention. Such media include, but are not limited to electronic storage media (e.g., magnetic discs, tapes, cartridges, chips), optical media (e.g., CD ROM), and the like. Such media may include addresses to internet sites that provide such instructional materials.

In some embodiments, the kits can comprise one or more packaging materials such as, for example, a box, bottle, tube, vial, container, sprayer, insufflator, intravenous (I.V.) bag, envelope, and the like; and at least one unit dosage form of an agent comprising active agent(s) described herein and a packaging material. In some embodiments, the kits also include instructions for using the composition as prophylactic, therapeutic, or ameliorative treatment for the disease of concern.

In some embodiments, the kits can comprise one or more packaging materials such as, for example, a box, bottle, tube, vial, container, sprayer, insufflator, intravenous (I.V.) bag, envelope, and the like; and a first composition comprising at least one unit dosage form of an agent comprising one or more active agent(s) (e.g., APP specific BACE inhibitor (ASBI) such as galangin, rutin, and analogues, derivatives, a tautomer or stereoisomer thereof, or prodrug thereof as described herein) within the packaging material, along with a second composition comprising a second agent such as, for example, an agent used in the treatment and/or prophylaxis of Alzheimer's disease (e.g., as described herein), or any prodrugs, codrugs, metabolites, analogs, homologues, congeners, derivatives, salts and combinations thereof. In some embodiments, the kits may also include instructions for using the composition as a prophylactic, therapeutic, or ameliorative treatment for the disease of concern.

In certain embodiments the instructions/instructional materials when present teach dosages and/or treatment regimen(s) and/or counter-indictions for the active agents contained in the kit. While the instructional materials, when present, typically comprise written or printed materials they are not limited to such. Any medium capable of storing such instructions and communicating them to an end user is contemplated by this invention. Such media include, but are not limited to electronic storage media (e.g., magnetic discs, tapes, cartridges, chips), optical media (e.g., CD ROM), and the like. Such media may include addresses to internet sites that provide such instructional materials.

EXAMPLES

The following examples are offered to illustrate, but not to limit the claimed invention.

Example 1

APP-Specific BACE Inhibitors (ASBI)

A Novel Class of Therapeutic Agents for Alzheimer's Disease

A critical limitation of protease inhibitory strategies (e.g., BACE inhibitors) in the treatment of various pathologies is the promiscuity of substrate target effects, i.e., the inhibition of cleavage of all substrates of a given targeted protease, such as BACE or the γ-secretase complex. In the case of γ-secretase, substrates other than APP, such as Notch, raise concerns for potential side effects of γ-secretase inhibition, and the recent failure of the γ-secretase inhibitor, Semagacestat, serves to reinforce such concerns. In the case of BACE, inhibition of non-APP substrates such as PSGL1 or LRP raises similar concerns.

Therefore, the optimal BACE inhibitor would be one that would bind not to BACE but rather to APP, leading to APP-specific BACE inhibition (ASBI). Such a therapeutic would represent a new class of Alzheimer's disease therapeutics: ASBIs.

The data reported in this example on the identification of the first ASBIs demonstrate that such an approach is feasible. APP-specific BACE inhibitors (ASBIs) inhibit the BACE cleavage of the amyloid precursor protein (APP) but not the proteolytic cleavage of other substrates. Through screening of a small library of 448 clinical compounds (NCC 3364) in the ASBI assays a bioflavonoid was identified—rutin, a citrus flavonoid glycoside—that was effective as an ASBI at a dose of 1 µM. Further analysis of a group of bioflavonoids revealed a second molecule, galangin, a bioflavonoid from the galangal rhizome, that similarly acts as an ASBI at a dose of 50 µM. These bioflavonoids represent the first members of what believed to be new class of disease-modifying therapeutic agents for AD.

It is believed, the systematic application of the approach outlined herein to identify APP-specific BACE inhibitors, and evaluate their in vivo ability to modulate APP processing specifically, has not been previously reported. A bioflavonoid nutritional supplement is identified that provides molecular lead compound that acts as an ASBI in cell models. It has been shown that increasing brain levels of this bioflavonoid through a prodrug approach leads to reduction of Aβ42 upon in the AD mouse model. Thus ASBIs represent a novel class of therapeutic agents for AD.

Materials and Methods

Compounds.

Rutin (ASBI-1) was obtained from Sigma (cat # R5143, St. Louis, Mo.), Galangin (ASBI-2) was obtained from Sigma (cat #282200, St. Louis, Mo.) and progalangin (PG-1) was synthesized.

ASBI Assay.

Consist of two parts a) evaluation of a compound for inhibition of the BACE cleavage of the MBP-C125 substrate and b) evaluation of the candidate for BACE inhibition of the P5-P5' substrate.

a) MBP-C125 Cleavage Assay.

A protein construct of Maltose-Binding-Protein carrying the 125 C-terminal residues of APP (1 uL of 1 mM in water) was incubated with a flavonoid (100 uM) for 15 minutes.

The mix was then submitted to cleavage by BACE (Sigma # B9059, 5 µl of 3 unit/ml in BACE buffer) for 30 minutes. After 0, 10, 20 and 30 minutes, 2 uL the reaction mixture were frozen and the different time points were quantified simultaneously for the amount of APP-C99 created. The quantification was done by using a Perkin Elmer ALPHALisa Amyloid Amyloid Beta kit (AL275C) modified by replacing the anti-Abeta acceptor beads (AL275AC) with anti-APP acceptor beads (AL275AC) and making the antibody mix with 2×ALPHALisa buffer.

b) P5-P5' cleavage assay.

The inhibition of BACE cleavage of the fluorescence substrate P5-P5' by the flavonoids at 100 uM was measured using the β-Secretase (BACE1) Activity Detection Kit from Sigma-Aldrich (CS0010) and the standard protocol.

Plasmids.

The pAPtag5-NRG1-β1 construct was kindly provided by Dr. Carl Blobel (Horiuchi et al. (2005) *Dev. Biol.* 283: 459-471). The BACE1 construct was a gift from Dr. Michael Willem and Dr. Christian Haass (Willem et al. (2006) *Science* 314: 664-666). Constructs pCMV5-Mint3, pMst-AβPP, pG5E1B-luc, and pCMV-LacZ were generously provided by Dr. Thomas Südhof, Dr. Patrick Mehlen, and Dr. Veronique Corset (Cao (2001) *Science* 293: 115-120. Construct pEF-N-FLAG-TAZ was kindly provided by Dr. Michael Yaffe and Dr. Iain Farrance. Construct pcDNA3.1-APLP2-Gal4 was described previously (Orcholski et al. (2011) *J. Alzheimers Dis.* 23: 689-699).

Cell culture and Western Blot.

The Chinese Hamster Ovary (CHO) cell line over-expressing human AβPP (7W) was kindly provided by Dr. Edward Koo. Plasmid constructs were transiently transfected into HEK293T or 7W cells with Lipofectamine 2000 (Invitrogen). Western Blot analysis was performed as previously described (Swistowski et al. (2009) *J. Neurosci.*, 29: 15703-15712). Briefly, 48 hr after transfection, cells were harvested and lysed in NP-40 Cell Lysis Buffer (50 mM TrisHCl, pH 8.0, 150 mM NaCl and 1% NP-40). Cell lysates were mixed with 1×LDS loading buffer (Invitrogen) and 50 mM DTT, and boiled at 100° C. for 10 min. After SDS-PAGE and electrotransfer, Western blotting was performed using anti-APP antibodies (CT15, a kind gift from Dr. Edward Koo, for β-CTF; 6E10 (Covance) for full length APP and sAPPα). Thirty minutes of TBS-Tween wash were followed by incubation with secondary antibodies.

Neuregulin1 Shedding Assay.

A cDNA construct encoding a human placental secreted alkaline phosphatase (SEAP)-NRG1 (pAPtag5-NRG1-β1) fusion protein was transfected in HEK293 cells in a 6-well format with or without full-length wild-type BACE1 using Lipofectamine 2000 (Invitrogen) as described previously (Vassar et al. (1999) *Science,* 286: 735-741). After transfection the medium was replaced with DMEM containing 10% heat-inactivated Fetal Bovine Serum and incubated for 24 hr. SEAP activity was measured in the conditioned medium. For alkaline phosphatase activity measurements, 200 µl of reaction solution (0.1 M glycine, pH 10.4, 1 mM $MgCl_2$, 1 mM $ZnCl_2$ containing 1 mg/ml 4-nitrophenyl phosphate disodium salt hexahydrate, Sigma) were added to 20 µl of the conditioned medium. The absorbance was read at 405 nm. Statistical analyses were performed using a two tailed Student's t-test.

Transactivation Assay.

HEK293T cells were co-transfected with five plasmids: (1) pG5E1B-luc, 0.3 µg; (2) pCMV-LacZ, 0.1 µg; (3) pMst-APP (APP-Gal4) or pcDNA3.1-APLP2-Gal4, 0.3 µg; (4) pCMV5-Mint3, 1.0 µg; (5) pEF-N-FLAG-TAZ, 1.0 µg.

Cells were harvested 48 hr after transfection in 0.2 ml per well Cell Culture Lysis Buffer (Promega), and their luciferase and β-galactosidase activities were determined with the Promega luciferase assay kit and the Promega β-galactosidase assay kit, respectively. The luciferase activity was standardized by the β-galactosidase activity to control for transfection efficiency and general effects on transcription. Transfections were performed at 80-90% confluency in six-well plates using Lipofectamine 2000 (Invitrogen).

Surface Plamon Resonance (SPR) Testing.

The surfaces of four flow cells (FC1, FC2, FC3, FC4) of a carboxymethylated-dextran (CM-5) chip were washed sequentially with 50 mM NaOH, 1 mM HCl, 0.05% $H_3PO_4$ and 20 mM sodium phosphate pH 7.4, 125 mM sodium chloride in parallel using a flow rate of 30 µd/min for 1 min using a Biacore T-100 (GE Healthcare). Three fusion proteins were immobilized via amine coupling using 20 mM phosphate, 125 mM sodium chloride pH 7.4. The three proteins were MBP-eAPP$_{230-624}$—a fusion protein containing maltose binding protein (MBP) and residues 230-624 of the ectodomain of APP (90-kDa) (FC4), eAPP$_{230-624}$—a protein that contains only residues 230-624 (45-kDa)(FC2), and TRX-eAPP$_{575-624}$—a fusion protein containing thioredoxin (TRX) and residues 575-624 of the ectodomain (20-kDa) (FC3). The proteins were produced as described in Libeu, et al. (2011) *J. Alzheimers Dis.,* 25(3): 547-566 Libeu et al (2011). The flow cell FC1 was used as a control. Galangin was diluted from 10 mM solutions in DMSO to 50 µM in 1% DMSO, 20 mM sodium phosphate pH 7.4, 125 mM sodium chloride, 0.05% Tween and then serially diluted by 1.5 for 10 steps. Binding traces were recorded for each dilution with a binding phase of 60 seconds and a dissociation phase of 240 seconds. Each cycle was performed at 20° C. with a constant flow rate of 20 µl/min. An additional 240 seconds of buffer flow at 60 µl per min across the cells was applied as a regeneration phase to facilitate complete dissociation of the compound from the protein. The sensograms were obtained by subtraction of the reference and buffer signals using the Biacore T100 Evaluation software. The binding curves were modeled with the PRISM (Graphpad Inc).

Pharmacokinetic (PK) Analysis.

The brain penetrance of galangin and progalangin were assessed in a standard PK comprising subcutaneous (Sub-Q) injection of 5 adult non-transgenic mice with 50 ul of a 5 mg/ml stock of compound in dimethylsulfoxide (DMSO) or a dose of 10 mg/kg for a 25 g mouse. Injected mice were anesthetized with ketamine/xylazine at 1, 2, 4, 6, and 8 hours and blood collected by cardiac puncture. The mice were then perfused with saline and brain tissue dissected and snap frozen on dry ice. Blood was centrifuged at 3000 rpm for 10 minutes and the plasma supernatant collected. Both plasma and the right hemibrain were sent to Integrated Analytical Solutions (IAS, Berkeley, Calif.) with a reference sample of compound for compound level analysis in tissue and plasma. The compound levels were determined using a LC-MS/MS approach.

Pilot Efficacy Testing.

Galangin and progalangin (PG-1) were dissolved in 10% solutol/15% DMSO/75% polyethylene glycol (PEG). Stock solutions were prepared at 10 mg/ml for each compound and 100 ul was injected subcutaneously daily for 14 days at a dose of 40 mkd. There were 5 PDAPP AD model J20 mice in both the galangin and progalangin groups, and 9 vehicle-only treated J20 controls. Mice were anesthetized, blood collected for plasma, and brain tissue collected as described above 2 hours after injection on the last day of treatment. The right hemibrain was further microdissected to isolate hippocampus and entorhinal cortex and this combined tissue was used for biochemical analysis. The remaining tissue and plasma was sent to 1AS for compound level analysis.
Biochemistry.

Aβ1-42 and Aβ1-40 levels were determined using the hippocampal/entorhinal cortical tissue. Briefly, frozen tissue samples were weighed, and a 20% w/v sonicate prepared in 5 M guandine-HCl/50 mM Tris, pH8. Sonication was performed with sample tubes in ice water, 4×5 seconds at 60 Hz, then 3×5 seconds at 80 Hz. Samples were then rotated at room temperature for 3 hours and frozen at −20° C. until assay. Invitrogen ELISA kits were used for Aβ1-40 and Aβ1-42 according to the manufacturer's instructions.
Results
Identification of APP-Specific BACE Inhibitors (ASBIs)

Figure 3A:
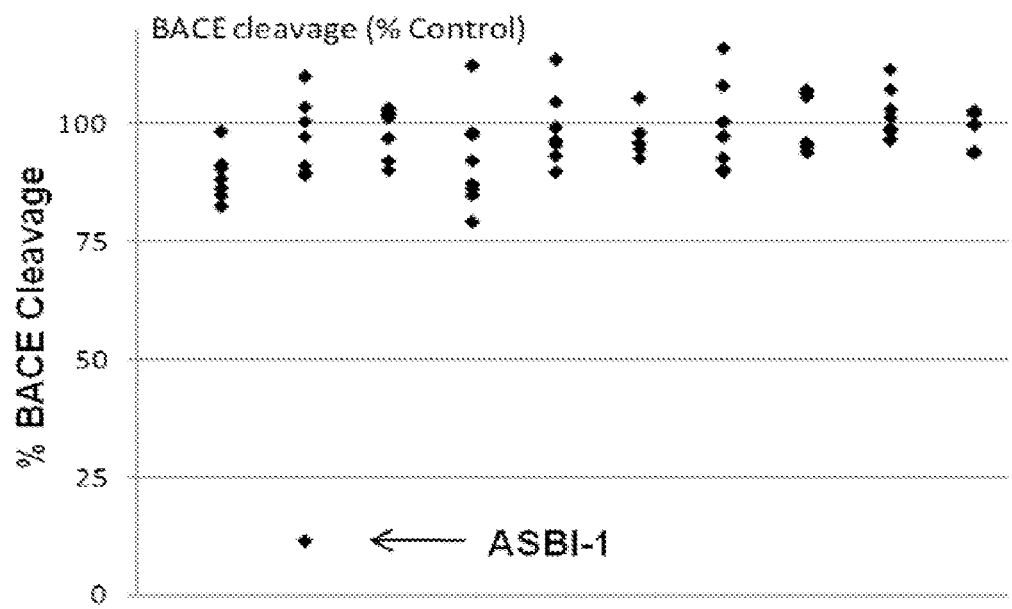
FIG. 3A illustrates the identification of Rutin in the AlphaLisa assay as shown in the scattergraph from screening of a small clinical library.
Figure 3B:
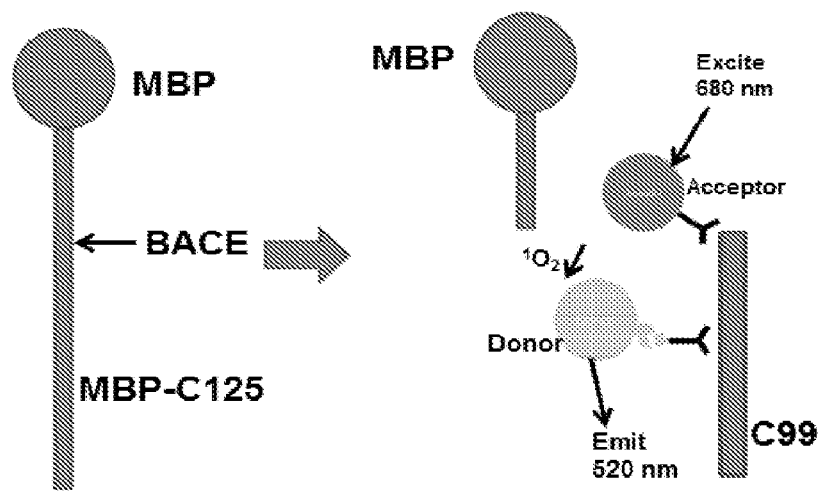
FIG. 3B schematically illustrates the primary AlphaLisa assay used for detection of the BACE cleavage of MBP-C125.

A primary high-throughput screening (HTS) assay was set up for identification of ASBIs using a dual-substrate testing paradigm (FIGS. 3A & 3B). The previously reported (Sinha et al. (1999) *Nature*, 402: 537-540) BACE substrate the MBP-C125 APP$_{695}$ wt fusion protein consisting of maltose binding protein fused to the carboxyterminal 125 amino acids of wild type APP, was used as the primary substrate; and the commercially available P5-P5' fluorescence substrate, derived from the P5-P5' residues of the BACE cleavage site of APP, was used as the secondary substrate. Each of these substrates was incubated with recombinant BACE (R&D (cat #931-AS-050) in a 96-well plate format. For the MBP-C125 substrate, the C-99 product from the BACE cleavage was measured using an AlphaLISA assay as a readout (FIG. 3B). For the P5-5' substrate, the loss of fluorescence following BACE cleavage was used as the readout. An ASBI would be predicted to inhibit the BACE cleavage of the MBP-C125 substrate, while not necessarily inhibiting cleavage of the fluorescence substrate, depending on where the ASB1 bound the APP substrate.

Figure 4:
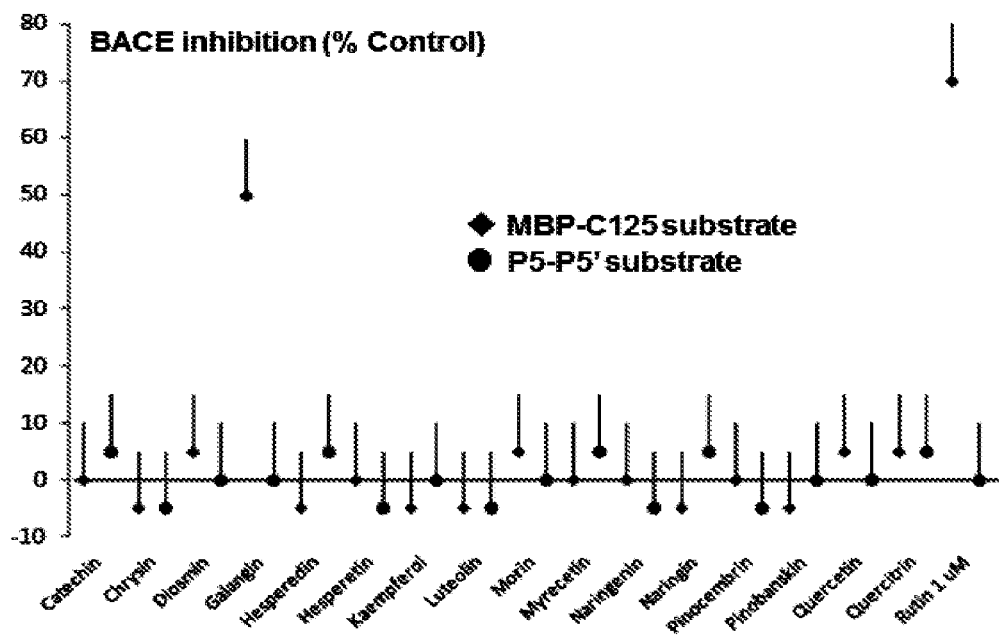
FIG. 4 shows the results of screening a family of Bioflavonoids in the MBP-C125 & P5-P5' cleavage by BACE to identify ASBIs.

Based on the preliminary screening of a clinical compound library of 448 compounds, the hit-rate was anticipated to be very low, since only one compound was identified in the initial screen. Dose response curves of potential 'hits' were next be done to identify validated 'hits' for further development. The HTS screening was performed at an initial concentration of 10 uM for each candidate. An initial screen of a small clinical compound library of 448 commercially available clinical compounds was completed. The screen yielded a single hit (FIG. 3A), identified as the bioflavonoid rutin (ASBI-1, also referred to as rutoside), which is derived from the citrus flavonoid glycoside found in buckwheat. This bioflavonoid decreased sAPPβ in SH-SY5Y cells, and was shown to be specific for APP, supporting the notion that rutin acts specifically on the BACE cleavage of APP. Next a panel of bioflavonoids (FIG. 4) was tested, first for their abilities to inhibit sAPPβ in the cells. Another bioflavonoid, galangin, was identified that also behaved as an ASBI, inhibiting the cleavage of the MBP substrate by BACE (FIG. 4, diamonds) while showing no inhibition of the P5-P5' substrate (FIG. 4, circles). Galangin (ASBI-2) is a flavanol found in galangal rhizome, and is commonly used as a nutritional supplement.
Effect of Bioflavonoid ASBIs on sAPPβ and APP Processing in Cells.

Figure 5A:
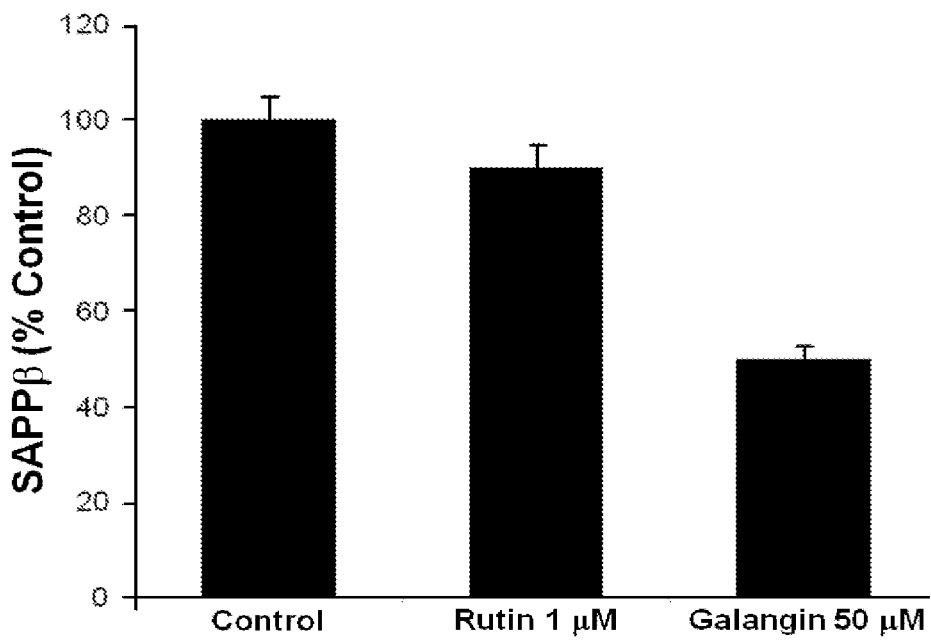
FIG. 5A shows inhibition of sAPPβ in SH-SY5Y by rutin & galangin. 5B shows binding of galangin to APP fragments by surface plasmon resonance (SPR).

APP is processed through two major pathways: the non-amyloidogenic pathway involves α-secretase cleavage, proteolyzing APP into sAPPα and α-CTF (C83), while the amyloidogenic pathway starts with β-secretase cleavage, cleaving APP into sAPPβ and β-CTF (C99). The β-CTF is then cleaved by the γ-secretase, which produces Aβ and AICD. The ability of the ASBIs to inhibit the β-secretase processing of APP was tested in SH-SY5Y neuroblastoma cells that express APP. The sAPPβ fragment formed from the BACE cleavage product was measured using an AlphaLisa assay from Perkin-Elmer (Cat # A2132). Following the discovery of rutin in the initial screen, it was demonstrated that at 1 µM it slightly inhibited the production of sAPPβ by SH-SY5Y cells (FIG. 5A). Testing of a panel of bioflavonoids led to the identification of galangin as an ASBI. Treatment of SH-SY5Y cells with galangin similarly decreased sAPPβ levels at 50 µM. No effect on APP levels was detected.
Bioflavonoid A SBIs Inhibit APP-Gal4 and APLP2-Gal4 Transactivation While the APP-C31 cleavage is associated with cell death, the APP intracellular domain (AICD) created following the γ-secretase cleavage has been implicated in various signaling pathways, and has been shown to modulate the expression of many genes including KAI1, neprilysin, and APP itself (Hong et al. (2000) *Science*, 290: 150-153). An APP-Gal4/Mint3/TAZ transactivation assay (Maillard et al. (2007) *J. Med. Chem.*, 50: 776-781; Hardy et al. (1991) *Trends Pharmacol. Sci.*, 12: 383-388) was established, and using this assay, it was found that ASBIs inhibited APP-Gal4 transactivation (FIG. 7). To confirm this effect, the APP-Gal4/Fe65 transactivation assay was employed. The effect of the ASBIs in the APLP2-Gal4 transactivation was examined (FIG. 7). These results indicate that rutin (ASBI-1) and galangin (ASBI-2) inhibit both APP and related family member APLP2-Gal4 transactivation.
Interaction of ASBIs with APP To explore the interaction of ASBIs with APP a ligand blot technique was used, where MBP-C125 APP was dot blotted on a nitrocellulose blot and binding to the protein was detected upon treatment with the bioflavonoids. A nitrocellulose filter-binding assay with bovine serum albumin (BSA) was used as a control. The binding of bioflavonoids was determined using both UV and MALDI mass spectrometric analysis. This is a qualitative measure of protein small molecule interaction but does show that the ASBI bound to APP.

Figure 5B:
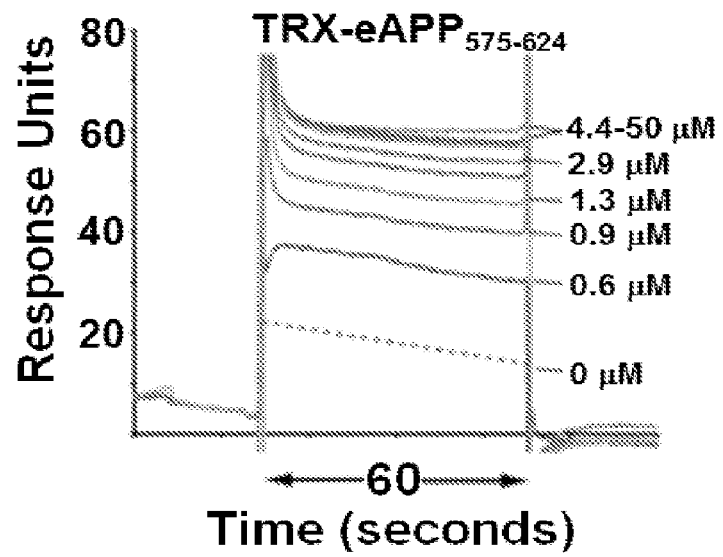
Figure 8:
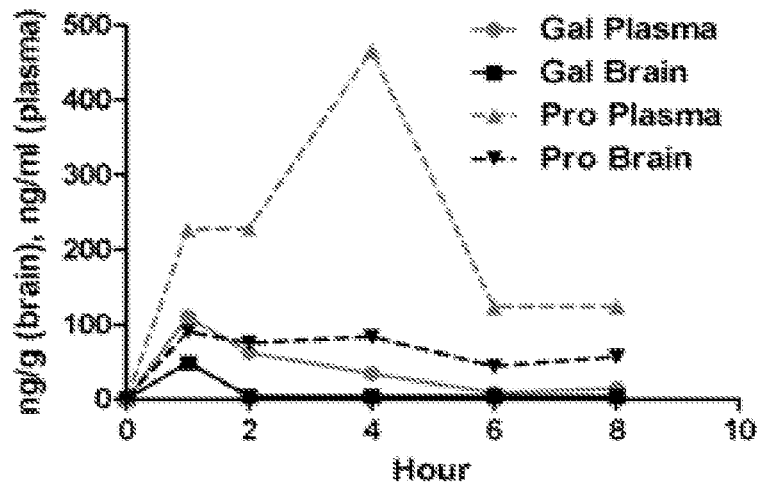
FIG. 8 illustrates the pharmacokinetics for galangin and progalangin (PG-1). Plasma levels were greater than brain tissue levels for both galangin and PG-1, but galangin levels were much higher after PG-1 injection than galangin itself.
Figure 9:
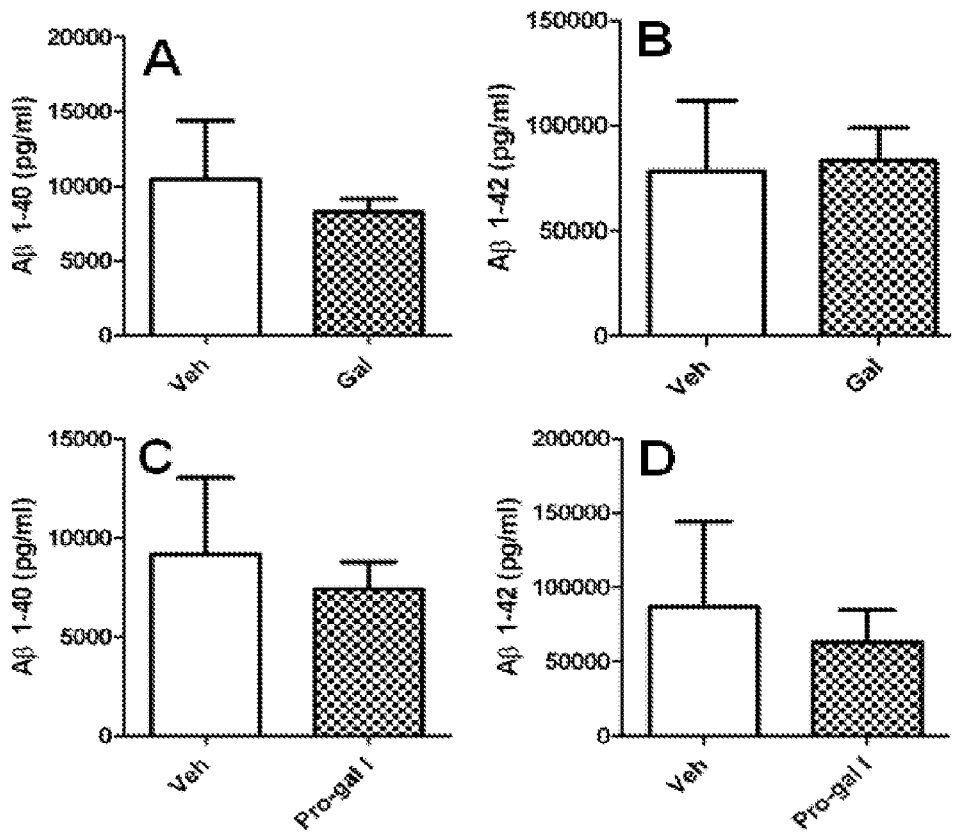
FIG. 9, panels A-D, show Aβ1-40 and Aβ1-42 levels. Aβ1-40 levels were slightly lower in the brains of galangin-treated mice (panel A) and Aβ1-42 was unchanged. Both Aβ1-40 and Aβ1-42 were slightly lowered in brains of pro-galangin 1-treated mice. Aβ1-40 (panel A) goes down slightly and Aβ1-42 (panel B) stays the same. Both Aβ1-40 (panel C) and Aβ1-42 (panel D) go down with pro-galangin-1. For siblings only all N=3.

Surface plasmon resonance (SPR) was then used to demonstrate binding to APP and to determine the affinity of galangin for APP.
Surface Plasmon Resonance (SPR) Screening:

The binding affinity of the compounds for the ectodomain of APP was determined using SPR. A technique for measuring the affinity of compounds to fragments of the ectodomain of APP was developed. For the galangin binding experiments TRX-eAPP575-624 was used. The eAPP was crosslinked linked to the CMS Biacore chips (GE Healthcare). Galangin at various concentrations were used in the flow through over the chip and the plasmon resonance signal was determined using a Biacore T100 (FIG. 5B).
Bioflavonoid ASBI Treatment Reduces Aβ in an AD Transgenic Mouse Model The brain permeability of the bioflavonoids rutin and galangin in mice was evaluated and it was found that after a 10 mpk sc administration no rutin was detectable in the brain, while low levels of galangin (Cmax~50 ng/g at 1 h) could be detected in the brain (FIG. 8). The brain to plasma ratio was 1:10. In order to see if the brain levels of galangin could be enhanced, the prodrug (PG-1) was tested and it resulted in increased delivery of galangin to the brain (Cmax~100 ng/g at 1 h). Based on these pharmacokinetic analysis it was decided to test galangin and progalangin (PG-1) in an AD mouse model, the PDAPP (J20) mice.

Treatment of J20 mice at 40 mpk with galangin shows some reduction of Aβ40 while Aβ42 was unchanged in the hippocampus and the cortex. However, treatment with progalangin shows both reduction of Aβ40 and Aβ42 consistent with the increased brain levels of galangin seen upon treatment with the prodrug. These results, taken together, indicate that the bioflavonoid galangin interacts directly with APP, inhibits BACE cleavage of APP but not neuregulin or a BACE-target peptide, inhibits BACE-dependent APP nuclear signaling, and reduces Aβ31-42 in a transgenic mouse model of AD.

Discussion

Two bioflavonoid analogs that are used as nutritional supplements and that inhibit the β-secretase mediated APP processing by a novel mechanism were identified. These molecules inhibit the BACE cleavage of the MBP-C125 APP substrate, resulting in the inhibition of the production of C99, but do not inhibit cleavage of the β-site peptide substrate (P5-P5'). In addition, these bioflavonoids reduce sAPPβ in neuroblastoma SH-SY5Y cells, whereas galangin fails to reduce neuregulin BACE-dependent shedding. Further, it was demonstrated that the activity is associated with binding to the MBP-C125 substrate. These findings define a new mechanism to modulate APP processing.

The approach described herein addresses a critical limitation of the protease inhibitory strategies for Alzheimer's disease (AD), providing a mechanism by which the inhibition of cleavage of all substrates of a given targeted protease, such as BACE or the γ-secretase complex, is avoided. The γ-secretase substrates other than APP, such as Notch, raise concerns for potential side effects of γ-secretase inhibition, and the recent failure of the γ-secretase inhibitor, Semagacestat, serves to reinforce such concerns. In the case of BACE, non-APP substrates such as PSGL1 and LRP raise similar concerns. Therefore, the optimal BACE inhibitor would be one that would bind to APP rather than to BACE, leading to APP-specific BACE inhibition (ASBI). Such a therapeutic, as described herein, represents a new class of Alzheimer's disease therapeutics.

Two known BACE substrates are likely to be important in immunological function: the P-selectin glycoprotein ligand-1 (Lichtenthaler et al. (2003) *J. Biol. Chem.* 278: 48713-48719), which mediates leukocyte adhesion, and the sialyl-transferase ST6Gal I (Kitazume et al. (2003) *J. Biol. Chem.*, 278: 14865-14871), an enzyme that is secreted after cleavage and is involved in regulating immune responses. The interaction of a sialyl-alpha-2,6 galactose residue, which is synthesized solely by ST6Gal I, with a B-cell-specific lectin, CD22/Siglec-2, is important for B-cell function (Id.). It is notable that mice deficient in some glycosylation enzymes appear to grow normally but show subtle neurological abnormalities with increasing age; glycosphingolipid-deficient mice show lethal audiogenic seizures induced by a sound stimulus. In this regard, it is important to note that no reports have yet appeared on the response of BACE1 null mice to immune challenge. BACE1 has also been shown to process the APP homologue, APLP2; this homologue has a different sequence specificity than that of APP around the putative BACE1 cleavage site, yet galangin also inhibited cleavage of APLP2 by BACE. The levels of APLP2 proteolytic products were decreased in BACE1 deficient mice and increased in BACE1 overexpressing mice (Pastorino et al. (2004) *Mol. Cell Neurosci.*, 25: 642-649). Given the great need for disease modifying therapies in AD, this approach of developing a APP substrate-specific BACE inhibitor is novel and could lead to clinical candidates that are effective against the disease.

Figure 5B:
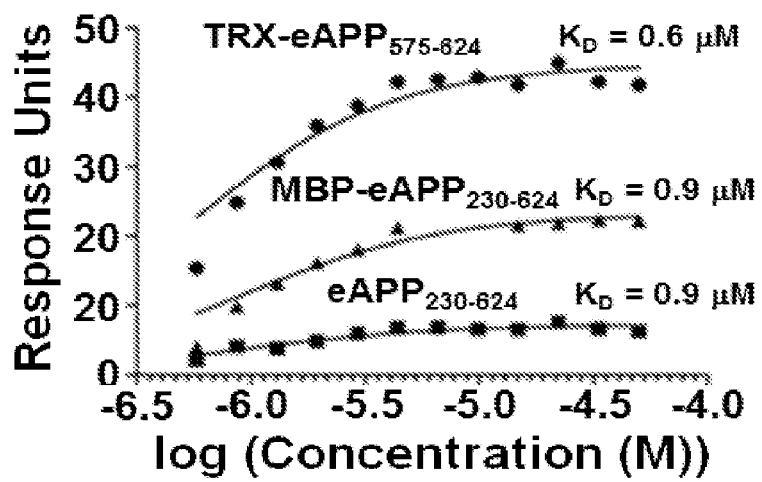
Figure 6A:
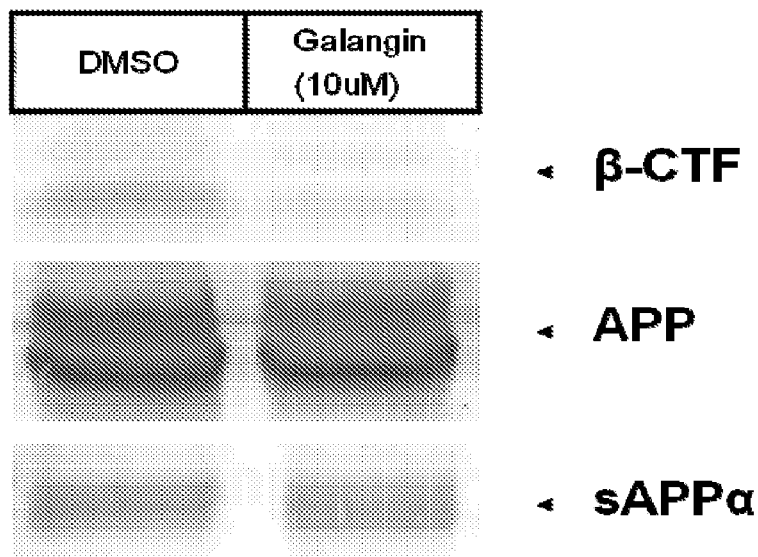
FIG. 6A shows that galangin inhibits β-CTF production. Chinese Hamster Ovary (CHO) cells stably over-expressing human APP were treated with 10 μM Galangin or DMSO for 24 hr, then the cell lysates and conditioned media were collected. The levels of full length APP and β-CTF in the cell lysates and the levels of sAPPα in the conditioned media were detected by western blot.
Figure 6B:
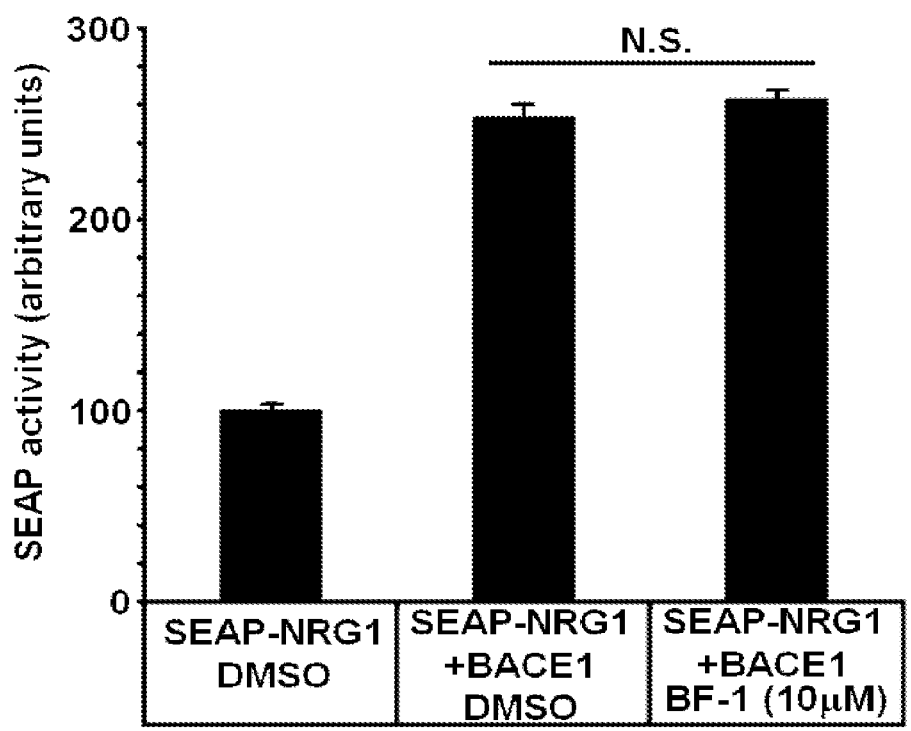
FIG. 6B shows that galangin does not inhibit BACE1 cleavage of neuregulin1. BACE1-dependent cleavage of SEAP-NRG1-β1 was evaluated by SEAP assays with supernatants of control human embryonic kidney 293 (HEK293) cells (SEAP-NRG1-β1) or HEK293 cells co-expressing BACE1 (SEAP-NRG1-β1+BACE1), treated with DMSO or Galangin (10 μM). An increase in shedding of the SEAP-NRG1-b1 fusion protein was measured upon BACE1 co-expression. Shedding in co-expressing cells was not suppressed by Galangin. Error bars indicate SEM. (N. S., p>0.05; n=4, student t test).

An HTS assay to identify ASBIs was set up. Initial screening of a clinical library of 448 compounds in this assay led to the identification of a bioflavonoid that specifically inhibited the MBP-C125 substrate of BACE while not preventing the cleavage of the P5-P5' substrate. This bioflavonoid, rutin, is a nutritional supplement that was also found to inhibit sAPPβ production in cells. A panel of bioflavonoids was then tested in the ASBI and sAPPβ assays in cell culture. From this testing another bioflavonoid, galangin, was identified. Galangin is another nutritional supplement that was effective in the ASBI assay, as well as in cells, in preventing the BACE cleavage of APP. Using a simple nitrocellulose filter ligand-binding assay initial binding of various bioflavonoids to the MBP-C125 substrate was demonstrated. A panel of bioflavonoids was screened in the ASBI assay. However, only rutin and galangin were effective as ASBIs (FIG. 4). Galangin modulates sAPPβ levels in cells and demonstrated binding to the APP substrate (FIG. 5). Interestingly, galangin also has been reported to be an inhibitor of acetylcholine esterase (AChE) (Guo et al. (2010) *Chemico-Biol. Interaction,* 187: 246-248) and to induce autophagy (Wen et al. (2012) *Pharmacology,* 89: 247-255).

It was demonstrated that the bioflavonoids inhibit BACE cleavage of APP and APLP2, using a HEK-293 assay transfected with APP or APLP2-Gal4 (see, e.g., Orcholski et al. (2011) *J. Alzheinzers Dis.*, 23(4):689-99 for a description of the assay). Transactivation is achieved upon transfection with Mint3 and Taz. The ASBI as expected to inhibit only the transactivation of APP-Gal4, not that of APLP2-Gal4. However, galangin inhibited both APP-Gal4 and APLP2-Gal4. Thus galangin exhibits APP-family specificity rather than APP specificity; however, given the demonstration of Aβ-like fragments derived from APLP2, the ability to inhibit BACE cleavage of both APP and APLP2 may be more desirable than inhibiting the cleavage of APP alone (Eggert et al. (2004) *J. Biol. Chem.* 279(18): 18146-18156).

Initial pharmacokinetic evaluation of these two bioflavonoids in brain uptake assays using NTg mice showed that rutin does not cross the blood-brain barrier, whereas galangin did show some brain penetration, thus enabling its evaluation for proof-of-concept studies in the transgenic (Tg) mouse model. Galangin was then evaluated for its in vivo effect on Aβ40 and Aβ42 (FIG. 7). The reduction of Aβ levels is very encouraging in this study. Further increase in brain levels of galangin is possible using a prodrug of galangin (PG-1), and it was demonstrated that PG-1 is more effective in vivo than galangin to reduce Aβ40 and Aβ42.

In conclusion, this current study indicates that certain bioflavonoids have the ability to bind APP and inhibit the BACE cleavage of APP and APLP2 thus suggesting that they function as APP specific BACE inhibitors. These represent a new class of therapeutics for Alzheimer's disease that would be devoid of the potential toxicity from direct inhibition of BACE. Galangin as its prodrug analog, progalangin-1 was also shown to be effective in reducing A1340 and Aβ42 in the AD mouse model.

Example 2

Progalangin as an ASBI

CNS exposure studies were performed and consisted of a time-course design to collect heparinized plasma and brains. Following sc administration of the galangin or progalangin (compound-2) at 10 mg/kg, plasma and brain levels of the compounds were determined by quantitative LC/MS/MS methodology. Plasma samples were precipitated with acetonitrile:methanol (1:1) cocktail containing an internal standard. The brain samples were homogenized directly in ethylacetate or extracted from 5M guanidine homogenates with the liquid-liquid method. The resulting supernatant was evaporated to dryness and subjected to the LC/MS/MS analysis. For each compound 5 mice were used for the analysis. The brain-to-plasma ratios and plasma/brain Cmax levels were then determined (see, e.g., FIG. 8).

Experimental Procedures—Compound Synthesis.

5,7-Diacetoxyflavone:

5,7-Dihydroxy-2-phenyl-4H-chromen-4-one (5.00 g, 19.67 mmol) was added to a solution of acetic anhydride in pyridine (1:5, 42 mL) and the reaction mixture was stirred for 60 hours at ambient temperature. The reaction mixture was diluted with diethyl ether (100 mL) and filtered. The solids were washed with additional diethyl ether (3×50 mL) and dried under high vacuum to afford 4-oxo-2-phenyl-4H-chromene-5,7-diyl diacetate (6.40 g, 18.92 mmol, 96%) as a white crystalline solid.

$^1$H NMR (400 MHz, CDCl$_3$) δ 2.36 (s, 3H, CH$_3$COO), 2.45 (s, 3H, CH$_3$COO), 6.67 (s, 1H, H-3), 6.85 (d, J=2 Hz, 1H, H-6), 7.36 (d, J=2 Hz, 1H, H-8), 7.50 (m, 3H, H-3', 5', H-4'), 7.84 (dd, J=8 Hz, 2H, H-2', 6');

$^{13}$C NMR (100 MHz, CDCl$_3$) δ 21.2 (q, CH$_3$COO), 21.3 (q, CH$_3$—C=O), 108.7 (d, C-3), 109.1 (d, C-8), 113.7 (d, C-6), 115.1 (s, C-4a), 126.3 (2×d, C-2', 6'), 129.2(2×d, C-3', 5'), 131.2 (d, C-4'), 131.9 (s, C-1'), 150.3 (s, C-5), 154.0 (s, C-7), 157.8 (s, C-8a), 162.6 (s, C-2), 168.1 (s, CH$_3$—C=O), 169.5 (s, CH$_3$COO), 176.5 (s, C-4).

Preparation of DMDO:

A 3 L, three-necked, round-bottomed reaction flask was equipped with an efficient mechanical stirrer, an addition funnel for solids, and a condenser (30 cm), set for downward displacement, attached to a two necked receiving flask, the latter cooled at −78° C. by means of a dry ice/acetone bath. The reaction flask was charged with a mixture of water (254 mL), acetone (192 mL), and NaHCO3 (58 g) and cooled at 5-10° C. with the help of an ice/water bath. While vigorously stirring and cooling, solid OXONE® (120 g, 0.195 mol) was added in five portions at 3 minute intervals. After 3 min of the last addition, the addition funnel was replaced with a stopper, and a moderate vacuum (80-100 mmHg) was applied to the flask. The cooling bath (5-10° C.) was removed from the reaction flask, and while vigorously stirring the DMDO/acetone solution was distilled and collected in the cooled (−78° C.) receiving flask over a period of 90 minutes. The receiving flask was warmed to −20° C. and dried for 3 hours over K$_2$CO$_3$. The DMDO solution was filtered into a dry flask and kept at −20° C. until used. Approximately 130 ml of DMDO solution was collected. The concentration of DMDO was determined by NMR by dissolving a 0.2 mL aliquot of the dried DMDO solution in CDCl$_3$ and comparing the height of the methyl proton signal of the dimethyldioxirane (at δ 1.65) with that of the $^{13}$C satellite peak to the right of acetone (0.5%), resulting in a 0.05 M DMDO solution. This analysis must be done without delay!

5,7-Diacetoxy-3-hydroxyflavone:

4-Oxo-2-phenyl-4H-chromene-5,7-diyl diacetate (1.80 g, 5.32 mmol) was added to a suspension of dried powdered 4 Å molecular sieves (1.80 g) in DCM (32 ml) and cooled to 0° C. DMDO solution (120 ml, 7.02 mmol, 1.32 equiv.) was added dropwise. The resulting solution was stirred at 0° C. for 3 hours and allowed to warm to ambient temperature and stirred at that temperature for 48 hours. The reaction mixture was filtered through a layer of anhydrous sodium sulfate on a bed of CELITE® and the volatiles were removed in vacuo at ambient temperature to afford crude 7-oxo-1a-phenyl-7,7a-dihydro-1aH-oxireno[2,3-b]chromene-4,6-diyl diacetate (ca. 1.90 g) as an oil. This oil was carried through to the next stage.

Crude reaction mixture (ca. 1.90 g) was stirred in DCM (32 ml) containing 15 mg of p-TSA. The reaction mixture solidified almost immediately. The reaction mixture was diluted with DCM (20 ml) and stirred for 2 days where TLC analysis indicated consumption of 7-oxo-1α-phenyl-7,7α-dihydro-1αH-oxireno[2,3-b]chromene-4,6-diyl diacetate. The reaction mixture was adsorbed onto silica gel and repeated flash column chromatography (Chloroform as eluent) afford impure 3-hydroxy-4-oxo-2-phenyl-4H-chromene-5,7-diyl diacetate (800 mg). Further purification was achieved by recrystallization from acetone/diethyl ether mixtures to afford 3-hydroxy-4-oxo-2-phenyl-4H-chromene-5,7-diyl diacetate (660 mg, 1.86 mmol, 35% over 2 steps) as a cream solid. The material was isolated as a hydrate. In addition, trace diethyl ether could not be removed under vacuum even after extended drying under vacuum.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

What is claimed is:

1. An APP specific BACE inhibitor (ASBI), wherein said APP specific BACE inhibitor is a galangin prodrug that is processed to galangin when administered to a mammal, wherein said galangin prodrug is characterized by the formula:

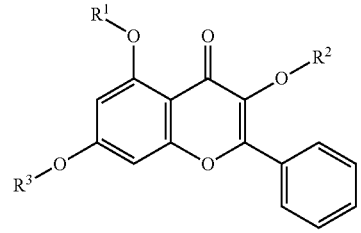

wherein:

R$^1$ and R$^3$ are each H,

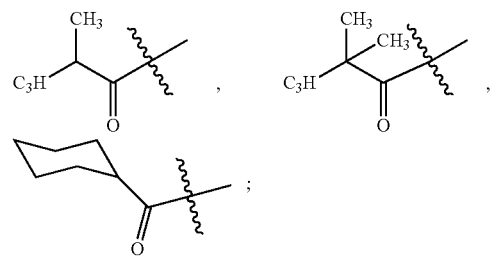

$R^2$ is H,

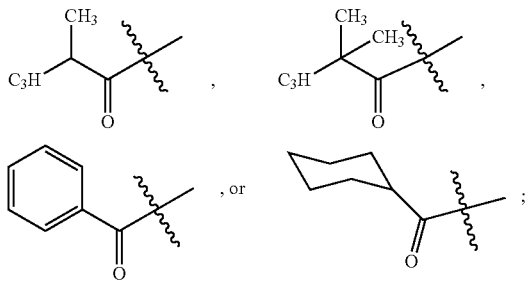

wherein at least one of $R^1$, $R^2$, and $R^3$ is not H; and wherein said prodrug partially or completely inhibits BACE processing of APP when administered to a mammal.

2. The APP specific BACE inhibitor (ASBI) according to claim 1, wherein $R^1$ and/or $R^2$ is H.

3. The APP specific BACE inhibitor (ASBI) according to claim 1, wherein $R^1$ and/or $R^3$ is

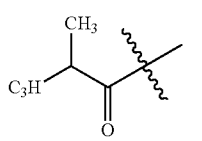

4. The APP specific BACE inhibitor (ASBI) of claim 3, wherein $R^1$ and $R^3$ are both

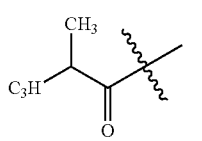

5. The APP specific BACE inhibitor (ASBI) according to claim 1, wherein
$R^2$ and/or $R^3$ are

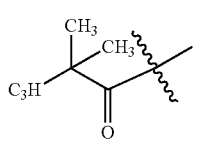

6. The APP specific BACE inhibitor (ASBI) of claim 5, wherein $R^2$ and $R^3$ are both

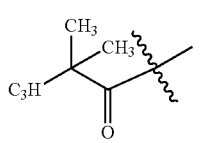

7. The APP specific BACE inhibitor (ASBI) according to claim 1, wherein $R^2$ and/or $R^3$ is

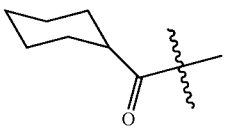

8. The APP specific BACE inhibitor (ASBI) of claim 7, wherein $R^2$ and $R^3$ are both

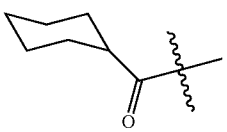

9. The APP specific BACE inhibitor (ABI) according to claim 1, wherein:
$R^1$ and $R^3$ are each

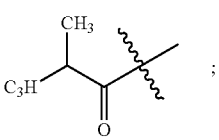

and
$R^2$ is H.

10. A pharmaceutical composition comprising an APP specific BACE inhibitor (ASBI) of claim 1 and a pharmaceutically acceptable carrier.

11. The pharmaceutical composition of claim 10, wherein the composition is formulated for oral, rectal, topical, injectable, transdermal, oral transmucosal or pulmonary administration.

12. The pharmaceutical composition of claim 10, wherein the composition in a unit dosage form comprising a powder, tablet, pill, capsule, lozenge, gel, syrup, liquid, slurry, suspension, dragee, gelcap, suppository, patch, nasal spray, injectable, implantable sustained-release formulation, mucoadherent film, topical varnish, or lipid complex.

13. The pharmaceutical composition of claim 10, wherein the composition is an emulsion or a nanoemulsion.

14. The pharmaceutical composition of claim 10, wherein the composition is an oil-in-water emulsion composition that may be diluted with water to a desired concentration.

15. The pharmaceutical composition of claim 10, wherein the composition is a sustained release formulation that comprises about 0.01% to about 99% w/w of the APP specific BACE inhibitor (ASBI) of claim 1 and one or more mucoadhesives and one or more of the following: one or more binders; one or more hydrogel forming excipients; one or more bulking agents; one or more lubricants; one or more glidants; one or more solubilizers; one or more surfactants; one or more flavors; one or more disintegrants; one or more buffering excipients; one or more coatings; one or more controlled release modifiers; and one or more other excipients and factors that modify and control the drug's dissolution or disintegration time and kinetics or protect the active drug from degradation.

16. The pharmaceutical composition of claim 15, wherein the composition comprises about 20% to about 80% w/w of the APP specific BACE inhibitor (ASBI).

* * * * *